US008466132B2

(12) United States Patent
Abato et al.

(10) Patent No.: US 8,466,132 B2
(45) Date of Patent: Jun. 18, 2013

(54) SUBSTITUTED TETRACYCLINE COMPOUNDS

(75) Inventors: Paul Abato, Providence, RI (US); Haregewein Assefa, Braintree, MA (US); Joel Berniac, Stoneham, MA (US); Beena Bhatia, Mansfield, MA (US); Todd Bowser, Charlton, MA (US); Jackson Chen, East Amherst, NY (US); Mark Grier, Watertown, MA (US); Laura Honeyman, Roslindale, MA (US); Mohamed Y. Ismail, Bedford, MA (US); Mark L. Nelson, Norfolk, MA (US); Kwasi Ohemeng, Norwood, MA (US); Jingwen Pan, North Grafton, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 1162 days.

(21) Appl. No.: 11/258,622

(22) Filed: Oct. 25, 2005

(65) Prior Publication Data
US 2006/0166945 A1 Jul. 27, 2006

Related U.S. Application Data

(60) Provisional application No. 60/622,027, filed on Oct. 25, 2004, provisional application No. 60/622,749, filed on Oct. 27, 2004.

(51) Int. Cl.
*A61K 31/65* (2006.01)
*C07C 237/26* (2006.01)

(52) U.S. Cl.
USPC .......................................... 514/152; 552/205

(58) Field of Classification Search
USPC ........................................ 552/205; 514/152
See application file for complete search history.

(56) References Cited

U.S. PATENT DOCUMENTS

| | | | |
|---|---|---|---|
| 2,980,584 A | 4/1961 | Hammer | 167/65 |
| 2,990,331 A | 6/1961 | Neumann et al. | 167/65 |
| 3,062,717 A | 11/1962 | Hammer | 167/65 |
| 3,165,531 A | 1/1965 | Blackwood et al. | 260/330.5 |
| 3,226,436 A | 12/1965 | Petisi et al. | |
| RE26,253 E | 8/1967 | Petisi et al. | |
| 3,338,963 A | 8/1967 | Petisi et al. | |
| RE26,271 E | 9/1967 | Boothe et al. | |
| 3,341,585 A | 9/1967 | Bitha et al. | |
| 3,345,379 A | 10/1967 | Martell et al. | |
| 3,345,410 A | 10/1967 | Winterbottom et al. | |
| 3,360,561 A | 12/1967 | Zambrano | |
| 3,373,196 A | 3/1968 | Bitha et al. | |
| 3,397,230 A | 8/1968 | Winterbottom et al. | |
| 3,403,179 A | 9/1968 | Zambrano | |
| 3,454,697 A | 7/1969 | Joyner et al. | 424/227 |
| 3,518,316 A | 6/1970 | Martell | |
| 3,557,280 A | 1/1971 | Weber et al. | 424/80 |
| 3,579,579 A | 5/1971 | Hlavka et al. | |
| 3,674,859 A | 7/1972 | Beutel et al. | 424/80 |
| 3,957,980 A | 5/1976 | Noseworthy | 424/227 |
| 4,018,889 A | 4/1977 | Armstrong | 424/80 |
| 4,024,272 A | 5/1977 | Rogalski et al. | 424/275 |
| 4,126,680 A | 11/1978 | Armstrong | 424/80 |
| 4,806,372 A | 2/1989 | Strumskis | 426/129 |
| 5,021,407 A | 6/1991 | Levy | 514/154 |
| 5,248,797 A | 9/1993 | Sum | |
| 5,258,372 A | 11/1993 | Levy | 514/154 |
| 5,281,628 A | 1/1994 | Hlavka et al. | |
| 5,284,963 A | 2/1994 | Sum et al. | |
| 5,326,759 A | 7/1994 | Hlavka et al. | |
| 5,328,902 A | 7/1994 | Sum et al. | |
| 5,371,076 A | 12/1994 | Lee et al. | |
| 5,380,888 A | 1/1995 | Sum et al. | |
| 5,386,041 A | 1/1995 | Sum et al. | |
| 5,401,729 A | 3/1995 | Sum et al. | |
| 5,401,863 A | 3/1995 | Hlavka et al. | |
| 5,420,272 A | 5/1995 | Sum et al. | |
| 5,430,162 A | 7/1995 | Sum et al. | |
| 5,442,059 A | 8/1995 | Sum et al. | |
| 5,457,096 A | 10/1995 | Sum et al. | |
| 5,466,684 A | 11/1995 | Sum et al. | |
| 5,494,903 A | 2/1996 | Hlavka et al. | |
| 5,495,018 A | 2/1996 | Sum et al. | |
| 5,495,030 A | 2/1996 | Sum et al. | |

(Continued)

FOREIGN PATENT DOCUMENTS

ES 302929 12/1964
WO WO-99/37306 A1 7/1999

(Continued)

OTHER PUBLICATIONS

Nelson et al., "Versatile and facile synthesis of diverse semisynthetic tetracycline derivatives via Pd-catalyzed reactions.", J. Org. Chem., vol. 68, pp. 5838-5851, 2003.*
Boothe, James H. et al, "6-Deoxytetracyclines. I. Chemical Modificaiton by Electrophilic Substitutions," *J. Am. Chem. Soc.*, vol. 82:1253-1254 (1960).
Koza, Darrell J., "Synthesis of 7-Substituted Tetracycline Derivatives," *Organic Letters*, vol. 2(6):815-817 (2000).
Koza, Darrell J. et al, "Palladium Catalyzed C—N Bond Formation in the Synthesis of 7-Amino-Substituted Tetracyclines," *J. Org. Chem.*, vol. 67:5025-5027 (2002).
Koza, Darrell J. et al, "Synthesis and Biological Evaluation of 9-Substituted Tetracycline Derivatives," *Bioorganic & Medicinal Chemistry Letters*, vol. 12:2163-2165 (2002).

(Continued)

*Primary Examiner* — Barbara P Badio
(74) *Attorney, Agent, or Firm* — Mintz Levin Cohn Ferris Glovsky and Popeo, P.C.; Heidi A. Erlacher; Yongjun Zhang

(57) ABSTRACT

The present invention pertains, at least in part, to novel substituted tetracycline compounds. These tetracycline compounds can be used to treat numerous tetracycline compound-responsive states, such as bacterial infections and neoplasms, as well as other known applications for tetracycline compounds such as blocking tetracycline efflux and modulation of gene expression.

14 Claims, No Drawings

U.S. PATENT DOCUMENTS

| | | | |
|---|---|---|---|
| 5,495,031 A | 2/1996 | Sum et al. | |
| 5,512,553 A | 4/1996 | Sum et al. | |
| 5,529,990 A | 6/1996 | Hlavka et al. | |
| 5,530,117 A | 6/1996 | Hlavka et al. | |
| 5,567,692 A | 10/1996 | Sum et al. | |
| 5,567,693 A | 10/1996 | Backer et al. | |
| 5,589,470 A | 12/1996 | Levy | 514/154 |
| 5,675,030 A | 10/1997 | Krishnan et al. | |
| 5,811,412 A | 9/1998 | Levy | 514/154 |
| 5,843,925 A | 12/1998 | Backer et al. | |
| 5,856,315 A | 1/1999 | Backer et al. | |
| 5,886,175 A | 3/1999 | Sum et al. | |
| 6,256,365 B1 | 7/2001 | Lai | 378/4 |
| 6,500,812 B2 | 12/2002 | Nelson et al. | |
| 6,617,318 B1 | 9/2003 | Nelson et al. | |
| 6,624,168 B2 | 9/2003 | Nelson et al. | |
| 6,642,270 B2 | 11/2003 | Nelson et al. | |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,833,365 B2 | 12/2004 | Levy et al. | |
| 6,841,546 B2 | 1/2005 | Draper et al. | |
| 6,846,939 B2 | 1/2005 | Nelson et al. | |
| 6,849,615 B2 | 2/2005 | Nelson et al. | |
| 7,001,918 B2 | 2/2006 | Huss et al. | |
| 7,045,507 B2 | 5/2006 | Draper et al. | |
| 7,056,902 B2 | 6/2006 | Nelson et al. | |
| 7,067,681 B2 | 6/2006 | Nelson et al. | |
| 7,094,806 B2 | 8/2006 | Nelson et al. | |
| 7,202,235 B2 | 4/2007 | Levy et al. | 514/152 |
| 7,208,482 B2 | 4/2007 | Garcia-Luzon et al. | 514/152 |
| 7,323,492 B2 | 1/2008 | Huss et al. | 514/429 |
| 7,326,696 B2 | 2/2008 | Nelson et al. | 514/512 |
| 7,361,674 B2 | 4/2008 | Nelson et al. | 514/357 |
| 7,414,041 B2 | 8/2008 | Levy | 514/154 |
| 7,521,437 B2 | 4/2009 | Nelson et al. | 514/152 |
| 7,553,828 B2 | 6/2009 | Nelson et al. | 514/152 |
| 2002/0128237 A1 | 9/2002 | Nelson et al. | |
| 2002/0128238 A1 | 9/2002 | Nelson et al. | |
| 2002/0132798 A1 | 9/2002 | Nelson et al. | |
| 2003/0069721 A1 | 4/2003 | Podlegar | 703/11 |
| 2004/0048835 A1 | 3/2004 | Nelson et al. | |
| 2004/0063674 A1 | 4/2004 | Levy et al. | |
| 2004/0092490 A1 | 5/2004 | Draper et al. | |
| 2004/0138183 A1 | 7/2004 | Nelson et al. | |
| 2004/0176334 A1 | 9/2004 | Nelson et al. | |
| 2004/0214800 A1 | 10/2004 | Levy et al. | |
| 2004/0214801 A1 | 10/2004 | Nelson et al. | |
| 2004/0242548 A1 | 12/2004 | Draper et al. | |
| 2004/0266740 A1 | 12/2004 | Huss et al. | |
| 2005/0020545 A1 | 1/2005 | Draper et al. | |
| 2005/0026875 A1 | 2/2005 | Nelson et al. | |
| 2005/0026876 A1 | 2/2005 | Nelson et al. | |
| 2005/0038002 A1 | 2/2005 | Nelson et al. | |
| 2005/0070510 A1 | 3/2005 | Draper et al. | |
| 2005/0119235 A1 | 6/2005 | Nelson et al. | |
| 2005/0137174 A1 | 6/2005 | Ohemeng et al. | |
| 2005/0143352 A1 | 6/2005 | Nelson et al. | |
| 2005/0143353 A1 | 6/2005 | Nelson et al. | |
| 2005/0148551 A1 | 7/2005 | Nelson et al. | |
| 2005/0187198 A1 | 8/2005 | Nelson et al. | |
| 2005/0215532 A1 | 9/2005 | Levy et al. | |
| 2005/0250744 A1 | 11/2005 | Levy et al. | |
| 2005/0282787 A1 | 12/2005 | Myers et al. | |
| 2005/0288262 A1 | 12/2005 | Bandarage et al. | |
| 2006/0003971 A1 | 1/2006 | Nelson | |
| 2006/0084634 A1 | 4/2006 | Huss et al. | |
| 2006/0089336 A1 | 4/2006 | Nelson et al. | |
| 2006/0148765 A1 | 7/2006 | Nelson | |
| 2006/0166944 A1 | 7/2006 | Berniac et al. | 514/152 |
| 2006/0166945 A1 | 7/2006 | Abato et al. | 514/152 |
| 2006/0166946 A1 | 7/2006 | Nelson et al. | |
| 2006/0194773 A1 | 8/2006 | Levy et al. | 514/152 |
| 2006/0281717 A1 | 12/2006 | Berniac et al. | 514/152 |
| 2006/0287283 A1 | 12/2006 | Amoo et al. | 514/152 |
| 2007/0072834 A1 | 3/2007 | Nelson et al. | 514/152 |
| 2007/0093455 A1 | 4/2007 | Abato et al. | 514/114 |
| 2007/0167415 A1 | 7/2007 | Levy et al. | 514/152 |
| 2007/0270389 A1 | 11/2007 | Garcia-Luzon et al. | 514/152 |
| 2008/0015169 A1 | 1/2008 | Nelson et al. | 514/152 |
| 2008/0070873 A1 | 3/2008 | Alekshun et al. | 514/153 |
| 2008/0118979 A1 | 5/2008 | Draper et al. | 435/375 |
| 2008/0167273 A1 | 7/2008 | Nelson et al. | 514/152 |
| 2008/0287401 A1 | 11/2008 | Johnston et al. | 514/152 |
| 2008/0300424 A1 | 12/2008 | Nelson et al. | 564/167 |
| 2008/0306032 A1 | 12/2008 | Nelson et al. | 514/152 |
| 2008/0312193 A1 | 12/2008 | Assefa et al. | 514/152 |
| 2009/0054379 A1 | 2/2009 | Huss et al. | 514/152 |
| 2009/0118269 A1 | 5/2009 | Berniac et al. | 514/231.5 |
| 2009/0124583 A1 | 5/2009 | Nelson et al. | 514/152 |
| 2009/0131696 A1 | 5/2009 | Levy | 552/203 |
| 2009/0156842 A1 | 6/2009 | Seyedi et al. | 552/204 |

FOREIGN PATENT DOCUMENTS

| | | |
|---|---|---|
| WO | WO-0187824 A2 | 11/2001 |
| WO | WO-0198259 A1 | 12/2001 |
| WO | WO 02/04406 * | 1/2002 |
| WO | WO-0204407 A2 | 1/2002 |
| WO | WO-02/072031 A2 | 9/2002 |
| WO | WO-02072532 A1 | 9/2002 |
| WO | WO-02/085303 A2 | 10/2002 |
| WO | WO-03/005971 A2 | 1/2003 |
| WO | WO-03075857 A2 | 9/2003 |
| WO | WO-03/079984 A2 | 10/2003 |
| WO | WO-03079983 A2 | 10/2003 |
| WO | WO-2004/038000 A2 | 5/2004 |
| WO | WO-2004/038001 A2 | 5/2004 |
| WO | WO-2004/064728 A2 | 8/2004 |
| WO | WO-2004/091513 A2 | 10/2004 |
| WO | WO-2005009943 A2 | 2/2005 |
| WO | WO-2005009944 A1 | 2/2005 |

OTHER PUBLICATIONS

Nelson, Mark L. et al, "Versatile and Facile Synthesis of Diverse Semisynthetic Tetracycline Derivatives via Pd-Catalyzed Reactions," *J. Org. Chem.*, vol. 68:5838-5851 (2003).

Petersen, P.J. et al, "In Vitro and In Vivo Antibacterial Activities of a Novel Glycylcycline, the 9-t-Butylglycylamido Derivative of Minocycline (GAR-936)," *Antimicrobial Agents and Chemotherapy*, vol. 43(4):738-744 (1999).

Sum, Phaik-Eng et al, "Glycylcyclines. 1. A New Generation of Potent Antibacterial Agents through Modification of 9-Aminotetracyclines," *J. Med. Chem.*, vol. 37:184-188 (1994).

Sum, Phaik-Eng et al, "Synthesis and Structure-Activity Relationship of Novel Glycylcycline Derivatives Leading to the Discovery of GAR-936," *Bioorganic & Medicinal Chemistry Letters*, vol. 9:1459-1462 (1999).

Sum, Phaik-Eng et al, "Synthesis and antibacterial activity of 9-substituted minocycline derivatives," *Bioorganic & Medicinal Chemistry Letters*, vol. 16:400-403 (2006).

Tally, F.T. et al, "Glycylcyclines: a new generation of tetracyclines," *Journal of Antimicrobial Chemistry*, vol. 35:449-452 (1995).

Communication Relating to the Results of the Partial Search Report enclosed with Invitation to Pay Additional Fees for Application No. PCT/US2005/039014, dated Mar. 21, 2006.

* cited by examiner

SUBSTITUTED TETRACYCLINE COMPOUNDS

RELATED APPLICATIONS

This application claims priority to U.S. Provisional Patent Application No. 60/622,027, filed on Oct. 25, 2004, and U.S. Provisional Patent Application No. 60/622,749, filed on Oct. 27, 2004, the entire contents of each of which are incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

In one embodiment, the invention pertains, at least in part, to substituted tetracycline compounds of Formula (I)

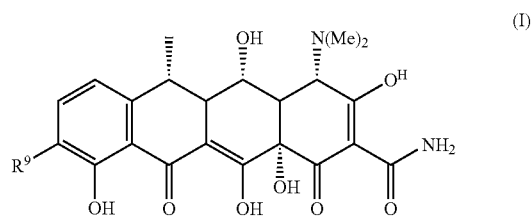

wherein $R^9$ is substituted or unsubstituted aminocarbonylalkyl, aminoalkylcarbonylaminoalkyl, carboxylate, arylalkylaminoalkyl, alkylcarbonylaminoalkyl, dialkylaminoalkyl, N-piperazinyl alkyl substituted phenyl, alkoxy substituted phenyl, substituted furanyl, alkylaminocarbonyl and pharmaceutically acceptable salts, esters, and prodrugs thereof.

In another embodiment, the invention pertains, at least in part, to substituted tetracycline compounds of Formula (II):

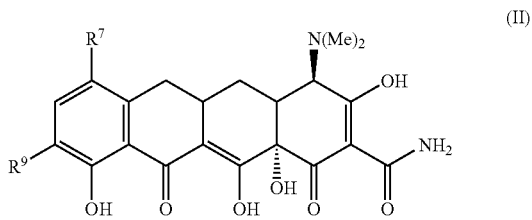

wherein $R^7$ is dimethylamino, substituted phenyl, substituted pyridinyl, alkoxycarbonylalkylaminocarbonyl, pyridinylalkylaminoalkyl, pyridinylalkylaminocarbonyl, substituted or unsubstituted arylaminoalkylcarbonyl, substituted or unsubstituted tetrahydropyridinyl, cycloalkylaminoalkylcarbonyl, alkylaminoalkylcarbonyl, heteroarylaminoalkylcarbonyl, alkoxylcarbonyl substituted alkylaminoalkylcarbonyl or arylaminoalkylcarbonyl;

$R^9$ is ethyl, aminomethyl, dialkylaminocarbonylalkyl, hydrogen, alkoxy substituted alkynyl, carboxylate substituted alkynyl, alkoxycarbonyl substituted alkynyl, dialkylamino substituted phenyl, cyano, acyl, substituted carboxylate aminomethyl, alkylaminocarbonyl, and pharmaceutically acceptable salts, esters and prodrugs thereof.

In yet another embodiment, the invention pertains, at least in part, to substituted tetracycline compounds of Formula (III):

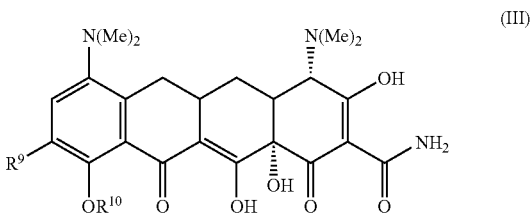

wherein

R$^9$ is R'—O—N═CR"—, R'—OC(═O)—, R$^{9a}$R$^{9b}$NC(═O)—, methoxycarbonyl substituted alkynyl, pyrazinyl, alkylaminocarbonyl alkyl, methoxymethyl, methoxymethyl substituted alkynyl, dimethylaminocarbonyl, cyclopropyl, methyl, amino substituted pyridinyl, alkoxyalkyl, alkylcarbonyl, arylcarbonyl, pyrimidinyl, alkoxycarbonyl substituted alkynyl, oxazolyl, pyrazolyl, carboxylate, halogen, piperidinylcarbonyl, alkyoxyalkyl substituted alkynyl, pyridinyl, thiazolyl, substituted or unsubstituted arylthiocarbonyl, cyano, deuterated alkylaminoalkyl, pyrrolidonylcarbonyl, carboxylatecarbonyl, alkylcarbonyl substituted phenyl, cyano substituted pyridinyl, aminocarbonyl substituted phenyl, dialkylaminomethyl, substituted or unsubstituted thiophenyl, substituted or unsubstituted furanyl, alkylcarbonylamino substituted pyridinyl, dialkylamino substituted phenyl, carboxylate substituted phenyl, azepanylcarbonyl, or piperazinylcarbonyl;

R$^{10}$ is hydrogen or alkenyl;

R' is unsubstituted alkyl, amino substituted alkyl, methoxy substituted alkyl, halogen substituted alkyl;

R" is alkyl;

R$^{9a}$ is hydrogen or alkyl;

R$^{9b}$ is alkyl, hydroxyl, alkoxy, hydroxyalkyl, alkoxyalkyl, alkylcarbonylaminoalkyl, alkoxycarbonylalkyl, hydroxyalkyl, aryl, cycloalkyl or aminoalkyl;

and pharmaceutically acceptable salts, esters and prodrugs thereof, provided that when R$^9$ is halogen, then R$^{10}$ is alkenyl.

In yet another embodiment, the invention also pertains, at least in part, to tetracycline compounds of Formula (IV):

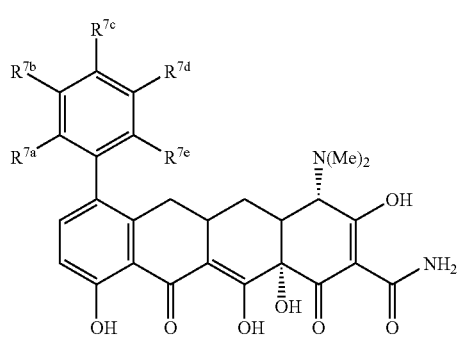

(IV)

wherein

R$^{7a}$ is methoxy, dialkylaminomethyl, substituted N-piperdinyl methyl, fluorine, or hydrogen;

R$^{7b}$ is hydrogen;

R$^{7c}$ is alkoxyalkylaminoalkyl, halogenated N-piperdinyl methyl, hydroxyl, dialkylaminoalkylamino, dialkylaminomethyl, substituted N-piperidinyl methyl, substituted N-pyrrolyl methyl, or hydrogen;

R$^{7d}$ is arylalkylaminoalkyl, arylalkyl substituted alkylaminoalkyl, substituted N-piperidinylmethyl, N-piperidinyl substituted aminomethyl, cyclopropylamino methyl, piperdinyl substituted alkyl, dialkylaminomethyl, heteroaryl substituted dialkylaminomethyl, alkylaminomethyl, cycloalkylaminomethyl, alkylaminoethyl, cyano substituted dialkylaminomethyl, N-pyrrolidinyl substituted methyl, N-pyrrolyl substituted methyl, methoxy substituted dialkylaminomethyl, alkoxyalkylaminomethyl, substituted carboxylate alkylaminomethyl, hydrogen or linked with R$^{7c}$ by a —O—CH$_2$—O— linker;

R$^{7e}$ is hydrogen, and pharmaceutically acceptable salts, esters and prodrugs thereof, provided that each of R$^{7a}$, R$^{7b}$, R$^{7c}$, R$^{7d}$, and R$^{7e}$ are not hydrogen.

In another further embodiment, the invention pertains, at least in part, to tetracycline compound of Formula (V):

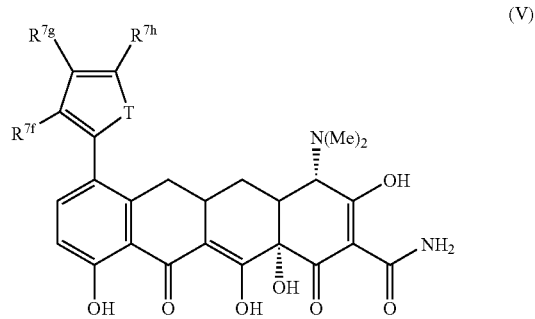

(V)

wherein

T is NH or O;

R$^{7f}$ is dialkylaminoalkyl, N-piperidinylamino alkyl, substituted or unsubstituted N-piperdinylalkyl, N-pyrrolidinylamino alkyl, substituted or unsubstituted N-pyrrolidinylalkyl, substituted or unsubstituted N-pyrrolylalkyl, alkenenyl substituted dialkylaminoalkyl, N-decahydroisoquinolinylalkyl, alkoxyalkylaminoalkyl, or hydrogen;

R$^{7g}$ is hydrogen;

R$^{7h}$ is heteroaryl substituted alkylaminoalkyl, dialkylaminoalkyl, substituted N-piperidinylalkyl or hydrogen, and pharmaceutically acceptable salts, esters and prodrugs thereof, provided that each of R$^{7f}$, R$^{7g}$, and R$^{7h}$ are not hydrogen.

In another embodiment, the invention pertains, at least in part, to tetracycline compounds of Formula (VI):

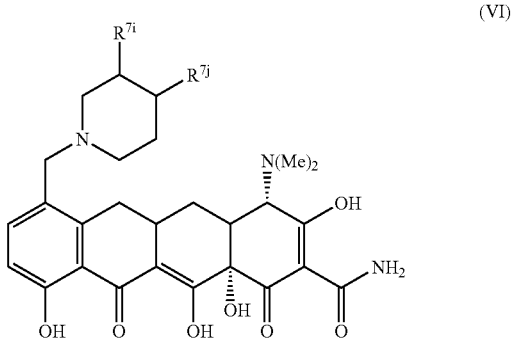

(VI)

wherein

R$^{7i}$ is fluorine or hydrogen;

R$^{7j}$ is trifluoromethyl, alkyloxycarbonyl, methyl, cyano, or hydrogen, and pharmaceutically acceptable salts, esters and prodrugs thereof, provided that both of R$^{7i}$ and R$^{7j}$ are not hydrogen.

In yet another embodiment, the invention also pertains, at least in part, to tetracycline compounds of Formula (VII):

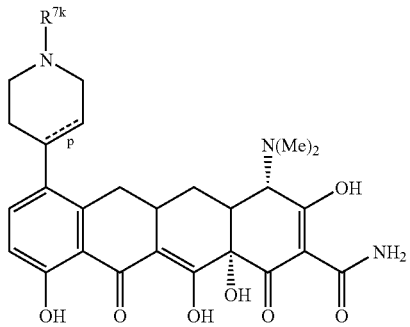

wherein p is a single or double bond;

$R^{7k}$ is alkyl, cycloalkyl, dialkylaminoalkylcarbonyl, alkoxyalkylcarbonyl, halogen substituted alkyl, halogen substituted cycloalkyl, or hydrogen, and pharmaceutically acceptable salts, esters and prodrugs thereof.

In yet another embodiment, the invention also pertains, at least in part, to tetracycline compounds of Formula (VIII):

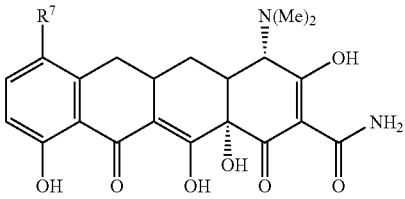

wherein $R^7$ is fluoro substituted N-pyrrolidinylalkyl, N-piperidinylalkylcarbonyl, dialkylaminoalkylaminocarbonyl, aminoalkyl, N-pyrroyl alkyl, dialkylamino substituted pyridinyl, phenyl substituted N-piperizinyl alkyl, alkylaminoalkyl, alkoxy substituted pyrimidinyl, 1-H-pyrimidin-2-onyl, cyano substituted pyridinyl, N-pyrrolidinyl alkyl, halogen substituted pyridinyl, arylalkylamino alkyl, alkoxyalkylaminoalkyl, N-imidizolylalkylcarbonyl, N-dihydroimidizolylalkylcarbonyl, imidizopyrimidinyl, imidizopyridinyl, or pyrizinyl substituted amino alkyl; and pharmaceutically acceptable salts, esters and prodrugs thereof.

In yet another embodiment, the invention also pertains, at least in part, to tetracycline compounds of Formula (IX):

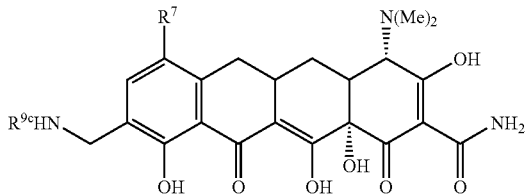

wherein $R^7$ is dialkylaminomethyl, alkoxy substituted phenyl, hydroxy, halogen substituted phenyl, halogenated alkyl substituted phenyl, naphthyl;

$R^{9c}$ is hydrogen, fluorinated alkyl or unsubstituted alkyl and pharmaceutically acceptable salts, esters and prodrugs thereof.

In another embodiment, the invention pertains, at least in part, to tetracycline compounds of the Formula (X):

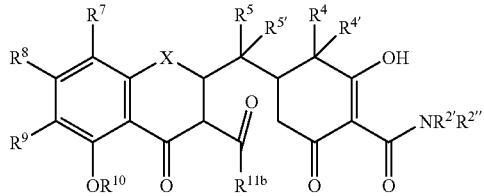

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen, optionally linked to $R^2$ to form a ring;

$R^2$ is hydrogen, alkyl, halogen, alkenyl, alkynyl, aryl, hydroxyl, thiol, cyano, nitro, acyl, formyl, alkoxy, amino, alkylamino, heterocyclic, or absent, optionally linked to $R^1$ to form a ring;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$ is hydrogen, alkyl, aryl, benzyl, arylalkyl, or a pro-drug moiety;

$R^{11b}$ is hydroxyl, alkoxy, aryloxy, or alkylamino;

$R^4$ and $R^{4'}$ are each independently $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkylcarbonyloxy, or arylcarbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7n})_{0-1}C(=W')WR^{7l}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{9f})_{0-1}C(=Z')ZR^{9d}$;

$R^{7l}$, $R^{7m}$, $R^{7n}$, $R^{7o}$, $R^{7p}$, $R^{7q}$, $R^{8a}$, $R^{8b}$, $R^{8c}$, $R^{8d}$, $R^{8e}$, $R^{8f}$, $R^{9d}$, $R^{9e}$, $R^{9f}$, $R^{9g}$, $R^{9h}$, and $R^{9i}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

Q is a double bond when $R^2$ is absent, Q is a single bond when $R^2$ is hydrogen, alkyl, halogen, hydroxyl, thiol, alkenyl, alkynyl, aryl, acyl, formyl, alkoxy, amino, alkylamino, cyano, nitro, or heterocyclic;

W is $CR^{7o}R^{7p}$, S, $NR^{7m}$ or O;

W' is O, $NR^{7q}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9g}R^{9h}$, S, $NR^{9e}$ or O;

Z' is O, S, or $NR^{9i}$, and pharmaceutically acceptable salts, esters and enantiomers thereof.

In another embodiment, the invention pertains, at least in part, to tetracycline compounds of the Formula (XI):

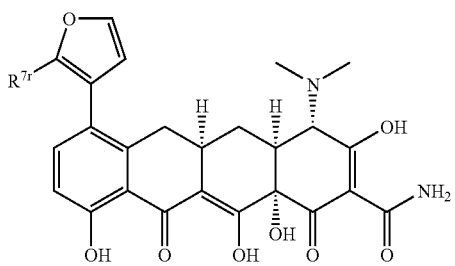

(XI)

wherein $R^{7r}$ is substituted or unsubstituted N-piperidinylalkyl, dialkylaminoalkyl and pharmaceutically acceptable salts, esters and enantiomers thereof.

In yet another embodiment, the invention pertains, at least in part, to tetracycline compounds of the Formula (XII):

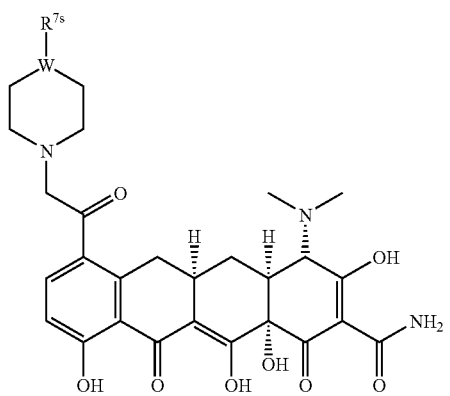

(XII)

wherein

W is N or CH; and $R^{7s}$ is substituted or unsubstituted alkyl, aryl, alkoxycarbonyl, alkylcarbonyl, cycloalkyl, or aminocarbonyl; and pharmaceutically acceptable salts, esters and enantiomers thereof.

In another embodiment, the invention pertains, at least in part, to tetracycline compounds of Formula (XIII):

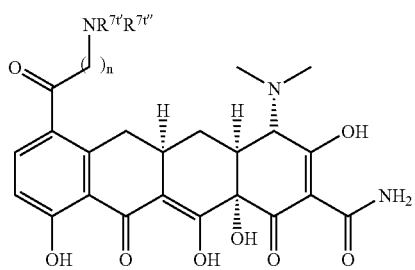

(XIII)

wherein n is 0, 1 or 2;

$R^{7t'}$ is hydrogen, alkyl, alkenyl or cycloalkyl;

$R^{7t''}$ is unsubstituted alkyl, dialkylaminoalkyl, halogenated alkyl, alkoxyalkyl, substituted or unsubstituted arylalkyl, cycloalkyl, alkenylalkyl, heterocyclic, cyano substituted alkyl, alkoxy substituted alkyl, heteroarylalkyl, aminocarbonylalkyl, aryl, hydrogen, alkylcarbonyl, aminoalkyl or alkoxycarbonyl; and pharmaceutically acceptable salts, esters and enantiomers thereof.

In another embodiment, the invention pertains, at least in part, to tetracycline compounds of Formula (XIV):

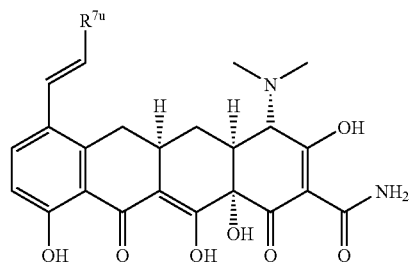

(XIV)

wherein $R^{7u}$ is substituted or unsubstituted N-piperidinylalkyl, dialkylaminoalkyl, alkoxyaminoalkyl, alkylaminoalkyl or dipiperidinium methyl; and pharmaceutically acceptable salts, esters and enantiomers thereof.

In another embodiment, the invention pertains, at least in part, to tetracycline compounds of formula (XV):

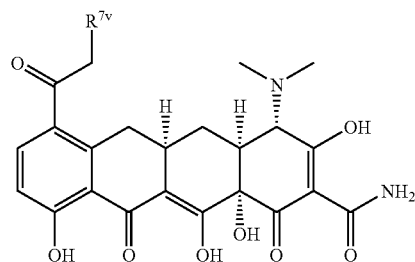

(XV)

wherein $R^{7v}$ is heterocyclic; and pharmaceutically acceptable salts, esters and enantiomers thereof.

9

In yet another embodiment, the invention pertains, at least in part, to tetracycline compounds of formula (XVI):

(XVI)

wherein:
$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each independently hydrogen, alkyl, aryl, benzyl, arylalkyl, or a pro-drug moiety;

$R^{3'}$ is hydroxyl, hydrogen, or a pro-drug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkylcarbonyloxy, or arylcarbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7c})_{0-1}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{9c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y'Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

10

In yet another embodiment, the invention pertains, at least in part, to tetracycline compounds of formula (XVII):

(XVII)

wherein:
$R^{2a}$ is alkyl or aryl;

$R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each independently hydrogen, alkyl, aryl, benzyl, arylalkyl, or a pro-drug moiety;

$R^{3'}$ is hydroxyl, hydrogen, or a pro-drug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkylcarbonyloxy, or arylcarbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7c})_{0-1}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{9c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, for S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In another further embodiment, the invention pertains, at least in part, to methods for treating subjects for tetracycline responsive states by administering to them an effective amount of a tetracycline compound of the invention, e.g., a compound of Formula I, II, III, IV, V, VI, VII, VIII, IX, X, XI, XII, XIII, XIV, XV, XVI or XVII or a tetracycline compound otherwise described herein.

In another further embodiment, the invention pertains, at least in part, to to pharmaceutical compositions which comprise an effective amount of a tetracycline compound of the invention, e.g., a compound of Formula I, II, III, IV, V, VI, VII, VIII, IX, X, XI, XII, XIII, XIV, XV, XVI or XVII or a tetracycline compound otherwise described herein, and a pharmaceutically acceptable carrier.

DETAILED DESCRIPTION OF THE INVENTION

The present invention pertains, at least in part, to novel substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

The term "tetracycline compound" includes many compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

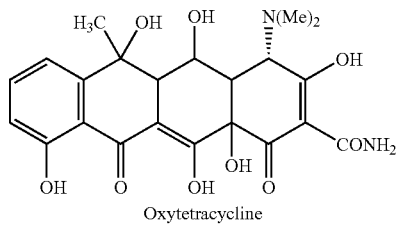
Oxytetracycline

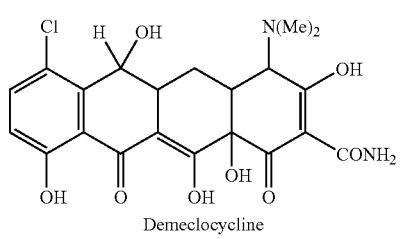
Demeclocycline

TABLE 1-continued

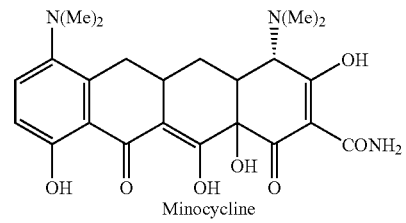
Minocycline

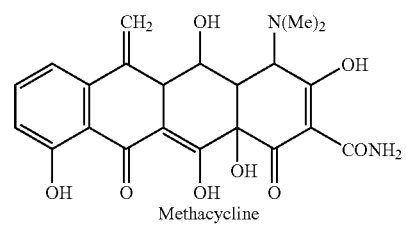
Methacycline

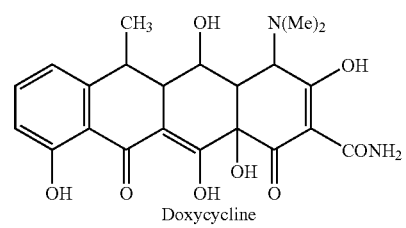
Doxycycline

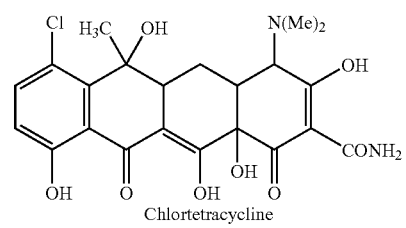
Chlortetracycline

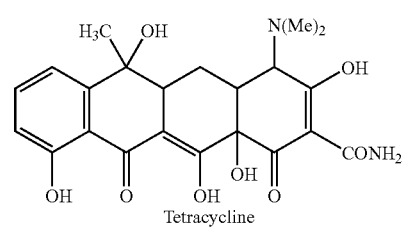
Tetracycline

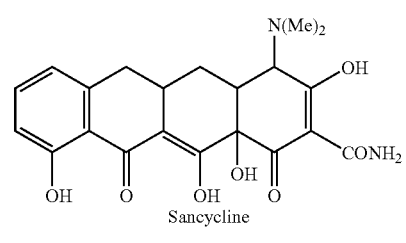
Sancycline

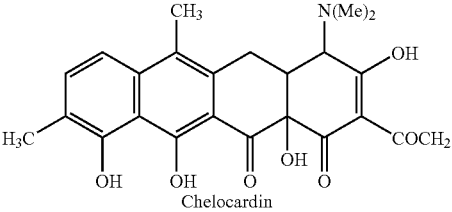
Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a Cl-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a Cl-6, 12 hemiketal tetracyclines; 11a Cl-6-methylene tetracyclines; 6, 13 diol tetracyclines; 6-benzylthiomethylene tetracyclines; 7, 11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-α acetoxy-6-demethyl tetracyclines; 6-β acetoxy-6-demethyl tetracyclines; 7, 13-epithiotetracyclines; oxytetracyclines; pyrazolotetracyclines; 11a halogens of tetracyclines; 12a formyl and other esters of tetracyclines; 5, 12a esters of tetracyclines; 10, 12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

In one embodiment, the invention pertains, at least in part, to substituted tetracycline compounds of Formula (I):

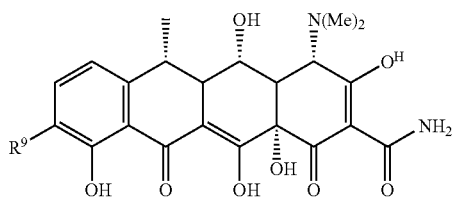

(I)

wherein $R^9$ is substituted or unsubstituted aminocarbonylalkyl, aminoalkylcarbonylaminoalkyl, carboxylate, arylalkylaminoalkyl, alkylcarbonylaminoalkyl, dialkylaminoalkyl, N-piperazinyl alkyl substituted phenyl, alkoxy substituted phenyl, substituted furanyl, alkylaminocarbonyl and pharmaceutically acceptable salts, esters, and prodrugs thereof.

In one embodiment, $R^9$ is substituted aminocarbonylalkyl (e.g., t-butyl substituted aminoalkylcarbonyl). In another embodiment, $R^9$ is dialkylaminoalkyl, such as dimethylaminoalkyl. In yet another embodiment $R^9$ is arylalkylaminoalkyl, such as phenylalkylaminoalkyl. In another embodiment, $R^9$ is alkoxy substituted phenyl which is further substituted by a pyrrolidinyl alkyl moiety. In yet another embodiment, $R^9$ is substituted furanyl, such as carbonyl substituted furanyl, dialkylaminoalkyl (e.g., dimethylaminoalkyl) substituted furanyl and pyrrolidinylalkyl substituted furanyl.

Examples of substituted tetracycline compounds of Formula (I) include:

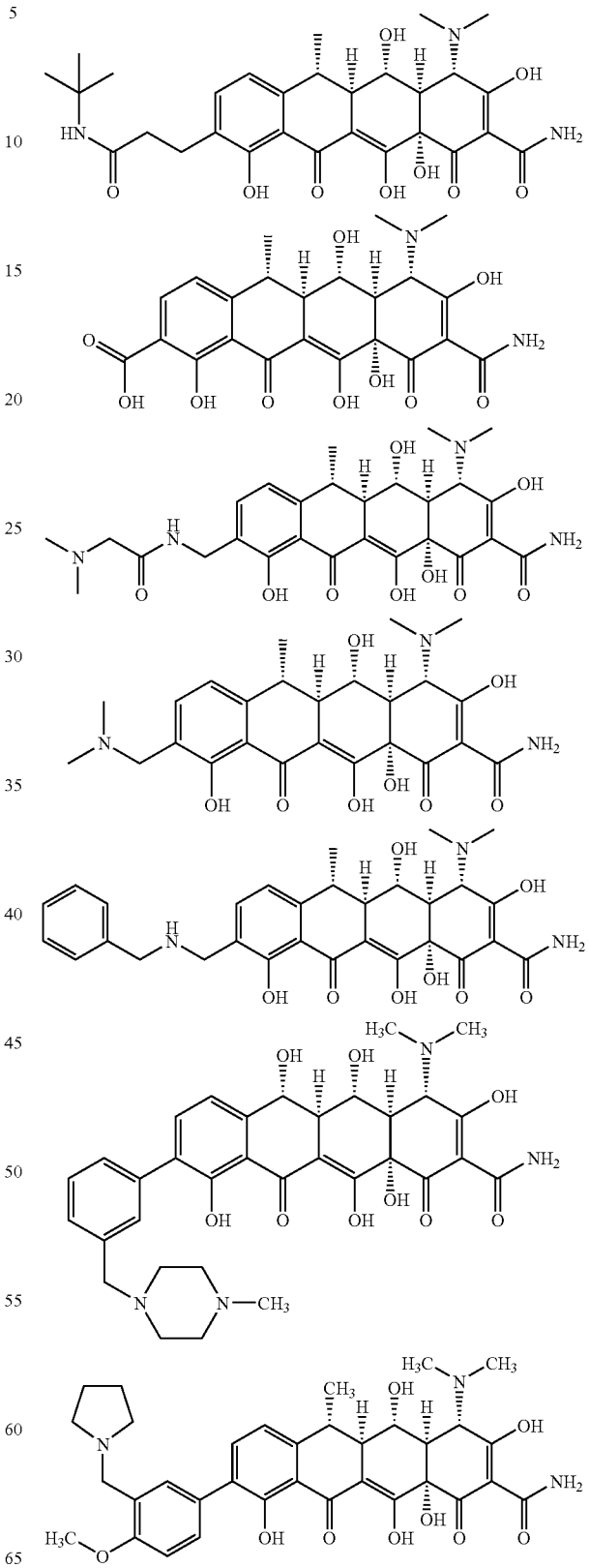

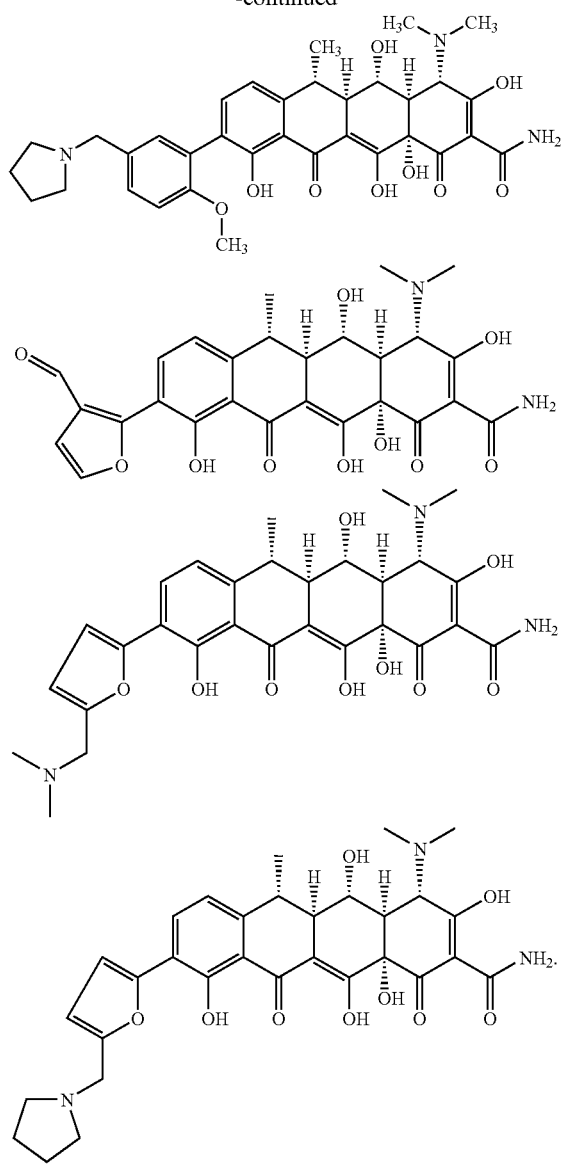

In another embodiment, the invention pertains, at least in part, to tetracycline compounds of Formula (II):

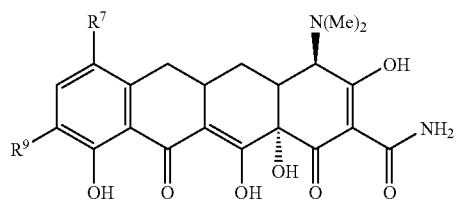

wherein

R⁷ is dimethylamino, substituted phenyl, substituted pyridinyl, alkoxycarbonylalkylamino carbonyl, pyridinylalkylaminoalkyl, pyridinylalkylamino carbonyl, substituted or unsubstituted arylaminoalkylcarbonyl, substituted or unsubstituted tetrahydropyridinyl, cycloalkylaminoalkylcarbonyl, alkylaminoalkylcarbonyl, heteroarylaminoalkylcarbonyl, alkoxylcarbonyl substituted alkylaminoalkylcarbonyl or arylaminoalkylcarbonyl;

R⁹ is ethyl, aminomethyl, dialkylaminocarbonylalkyl, hydrogen, alkoxy substituted alkynyl, carboxylate substituted alkynyl, alkoxycarbonyl substituted alkynyl, dialkylamino substituted phenyl, cyano, acyl, substituted carboxylate aminomethyl, alkylaminocarbonyl, and pharmaceutically acceptable salts, esters and prodrugs thereof.

In one embodiment, R⁷ is dimethylamino. In another embodiment, R⁹ is ethyl, dialkylaminocarbonylalkyl (e.g., dimethylaminocarbonylalkyl) alkyoxysubstituted alkynyl (e.g., methoxysubstituted alkynyl), carboxylate substituted alkynyl, alkoxycarbonyl substituted alkynyl (e.g methoxycarbonyl substituted alkynyl), dialkylamino substituted phenyl (e.g. dimethylamino substituted phenyl), cyano, acyl, substituted carboxylate aminomethyl or alkylaminocarbonyl (e.g., n-propylaminocarbonyl or t-butylaminocarbonyl).

In another embodiment, R⁹ is hydrogen. In yet another embodiment, R⁷ is substituted pyridinyl (e.g., methyl substituted pyridinyl), alkoxycarbonylalkylaminocarbonyl (e.g., methyoxycarbonylalkylaminocarbonyl), pyridinylalkylaminoalkyl, substituted or unsubstituted arylaminoalkylcarbonyl (e.g., phenylaminoalkylcarbonyl), substituted or unsubstituted tetrahydropyridinyl (e.g., isopropyl substituted tetrahydropyridinyl or dimethylaminoalkylcarbonyl substituted tetrahydropyridinyl), cycloalkylaminoalkylcarbonyl (e.g., cyclohexylaminoalkylcarbonyl or morpholinoaminoalkylcarbonyl), alkylaminoalkylcarbonyl, heteroarylaminoalkylcarbonyl (e.g., pyrimidinylaminoalkylcarbonyl) or alkoxylcarbonyl substituted alkylaminoalkylcarbonyl.

In yet another embodiment, R⁹ is aminomethyl. In another embodiment, R⁷ is substituted phenyl such as dichloro substituted phenyl.

Examples of tetracycline compounds of Formula (I) include:

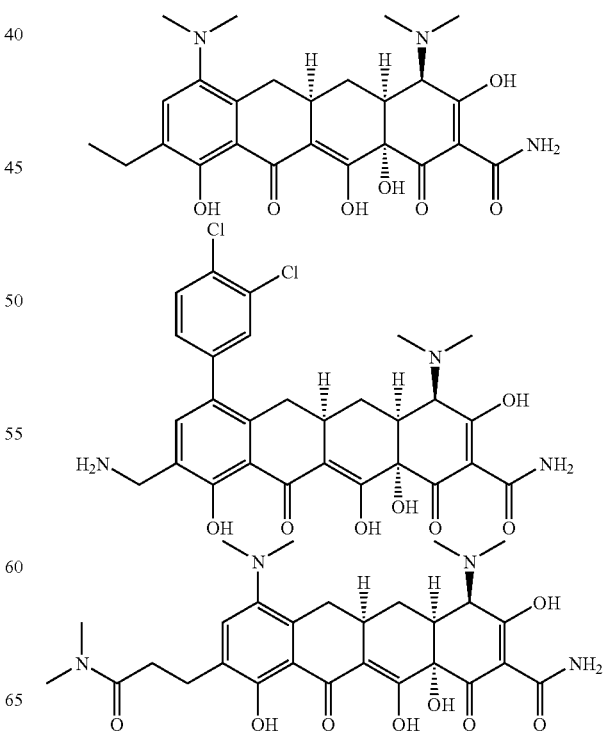

-continued
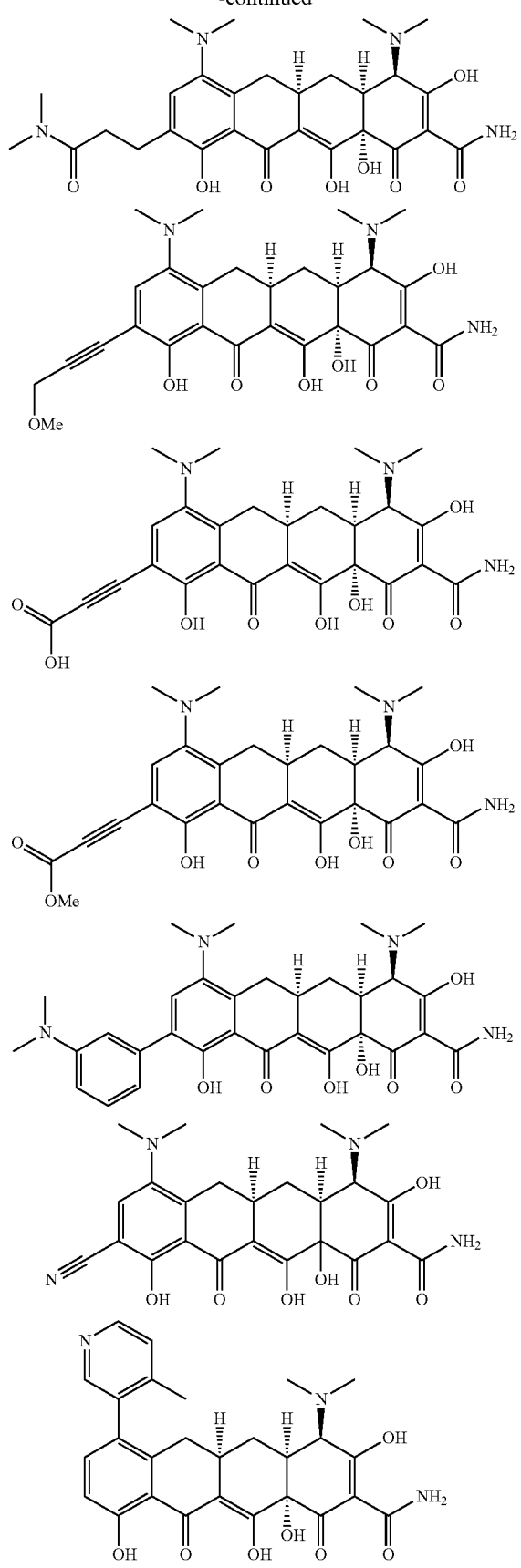
-continued
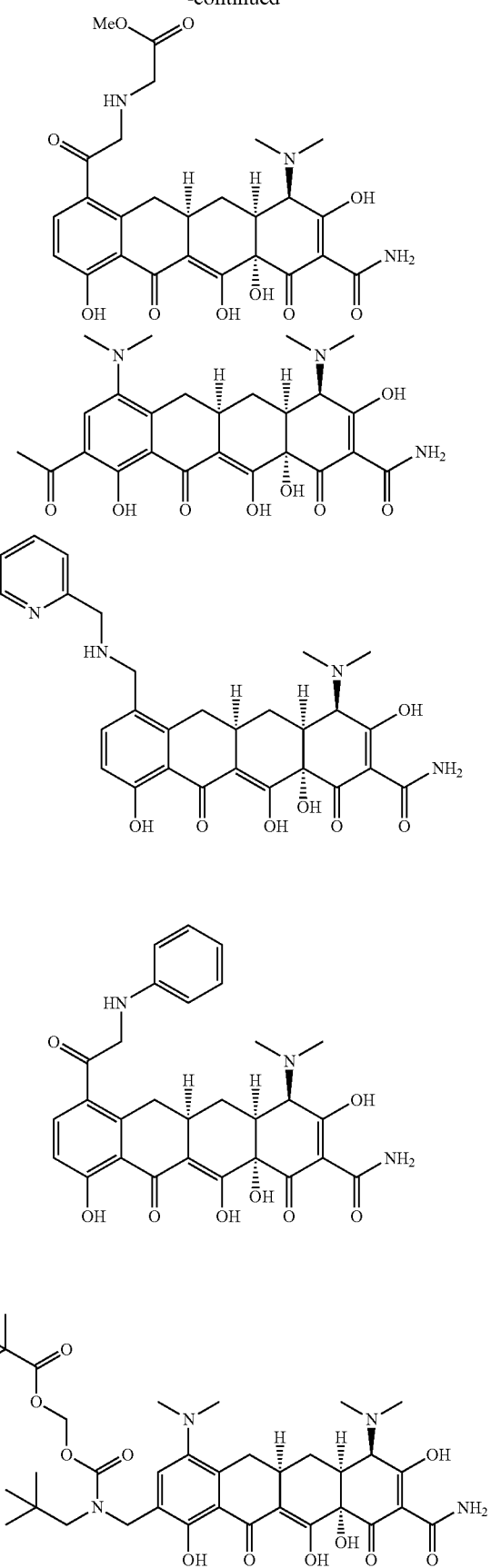

-continued
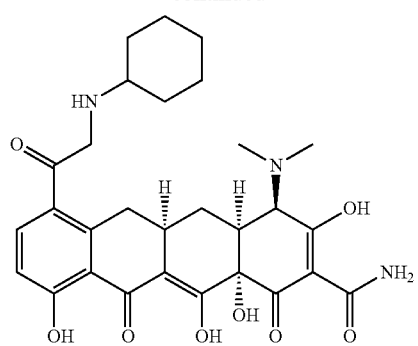
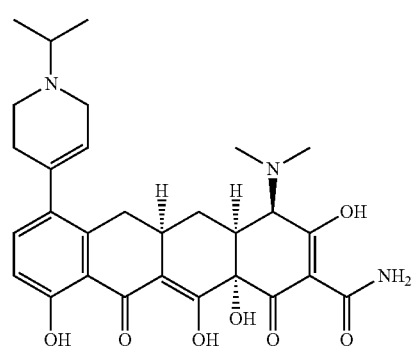
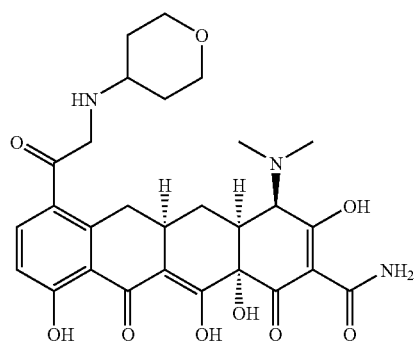
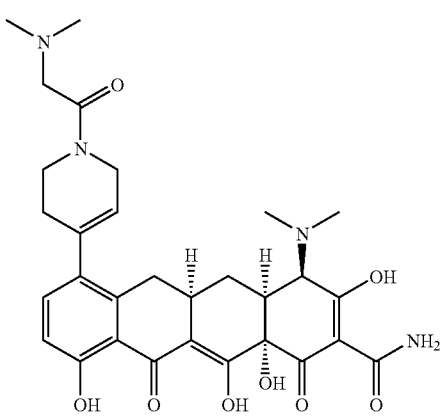
-continued
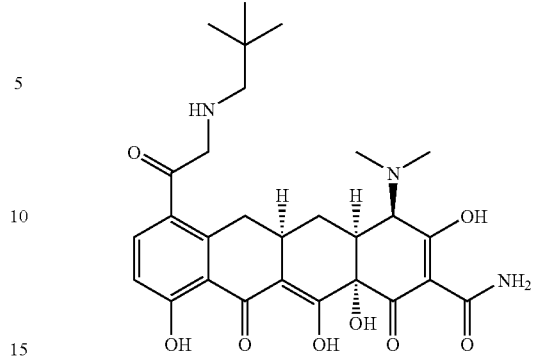
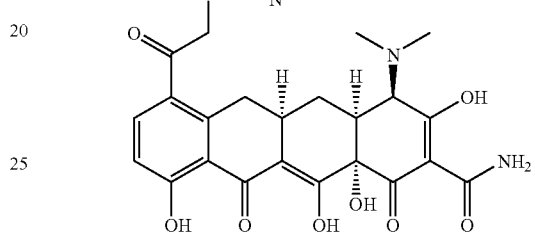
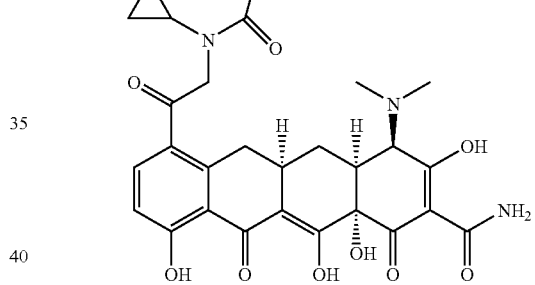
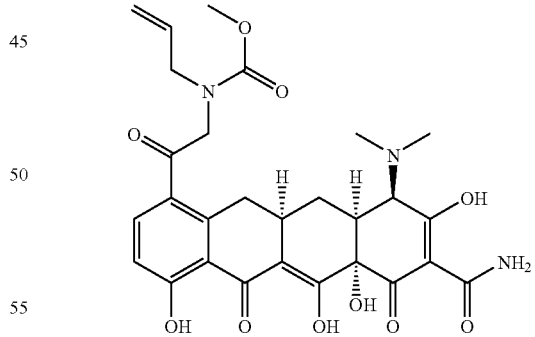
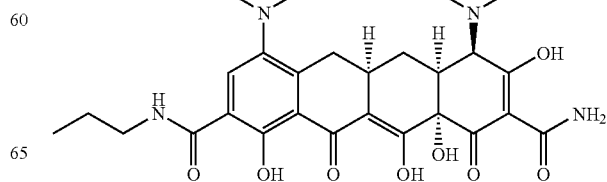

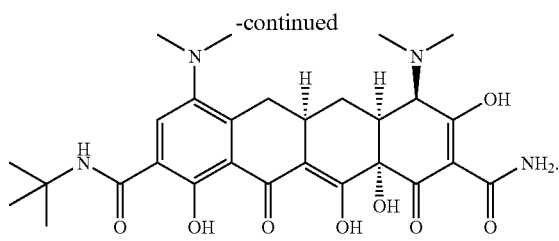

In another further embodiment, the invention pertains to tetracycline compounds of Formula (III):

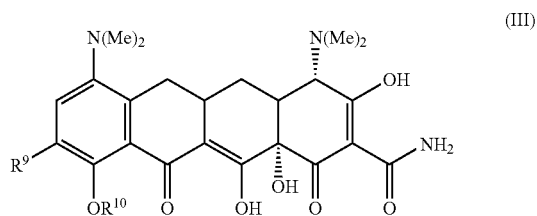

wherein $R^9$ is R'—O—N=CR"—, R'—OC(=O)—, $R^{9a}R^{9b}$NC(=O)—, methoxycarbonyl substituted alkynyl, pyrazinyl, alkylaminocarbonyl alkyl, methoxymethyl, methoxymethyl substituted alkynyl, dimethylaminocarbonyl, cyclopropyl, methyl, amino substituted pyridinyl, alkoxyalkyl, alkylcarbonyl, arylcarbonyl, pyrimidinyl, alkoxycarbonyl substituted alkynyl, oxazolyl, pyrazolyl, carboxylate, halogen, piperidinylcarbonyl, alkyoxyalkyl substituted alkynyl, pyridinyl, thiazolyl, substituted or unsubstituted arylthiocarbonyl, cyano, deuterated alkylaminoalkyl, pyrrolidonylcarbonyl, carboxylatecarbonyl, alkylcarbonyl substituted phenyl, cyano substituted pyridinyl, aminocarbonyl substituted phenyl, dialkylaminomethyl, substituted or unsubstituted thiophenyl, substituted or unsubstituted furanyl, alkylcarbonylamino substituted pyridinyl, dialkylamino substituted phenyl, carboxylate substituted phenyl, azepanylcarbonyl, or piperazinylcarbonyl;

$R^{10}$ is hydrogen or alkenyl;

R' is unsubstituted alkyl, amino substituted alkyl, methoxy substituted alkyl, halogen substituted alkyl;

R" is alkyl;

$R^{9a}$ is hydrogen or alkyl;

$R^{9b}$ is alkyl, hydroxyl, alkoxy, hydroxyalkyl, alkoxyalkyl, alkylcarbonylaminoalkyl, alkoxycarbonylalkyl, hydroxyalkyl, aryl, cycloalkyl or aminoalkyl;

and pharmaceutically acceptable salts, esters and prodrugs thereof, provided that when $R^9$ is halogen, then $R^{10}$ is alkenyl.

In one embodiment, $R^{10}$ is alkenyl. In another embodiment $R^9$ is halogen, for example, iodine.

In another embodiment, $R^{10}$ is hydrogen. In a further embodiment, $R^9$ is R'—O—N=CR"—, wherein R" is alkyl, such as methyl and R' is unsubstituted alkyl, for example, methyl.

In yet another embodiment, $R^{10}$ is hydrogen and $R^9$ is R'—OC(=O)—. In one embodiment R' is unsubstituted alkyl (e.g., ethyl or isopropyl), amino substituted alkyl (e.g., dialkylamino substituted alkyl, such as dimethylamino substituted alkyl), halogen substituted alkyl (such as trifluoromethyl substituted alkyl) or methoxy substituted alkyl.

In another embodiment, $R^{10}$ is hydrogen and $R^9$ is $R^{9a}R^{9b}$NC(=O)—. In one embodiment, $R^{9a}$ and $R^{9b}$ are each alkyl, such as, for example methyl or ethyl. In one embodiment, $R^{9a}$ is alkyl (e.g., methyl) and $R^{9b}$ is alkoxyalkyl, such as methoxyalkyl. In yet another embodiment, $R^{9a}$ is ethyl and $R^{9b}$ is n-propyl. In a further embodiment, $R^{9a}$ is hydrogen and $R^{9b}$ is hydrogen, hydroxy, alkoxy (e.g., methoxy, ethoxy or t-butyloxy), hydroxyalkyl, alkyl (e.g., methyl-t-butyl, n-propyl, ethyl, t-butyl or n-butyl), cycloalkyl (such as cyclopropyl), alkylcarbonylaminoalkyl (e.g., methylcarbonylaminoalkyl), alkoxycarbonylalkyl (e.g., methoxycarbonylalkyl), aryl (e.g., phenyl) or aminoalkyl.

In another embodiment, $R^{10}$ is hydrogen and $R^9$ is methoxycarbonyl substituted alkynyl, pyrazinyl, methoxymethyl, cyclopropyl, methyl, methoxymethyl substituted alkynyl, amino substituted pyridinyl, alkylcarbonyl (e.g., ethylcarbonyl or isopropylcarbonyl.), arylcarbonyl (e.g., phenylcarbonyl), pyrimidinyl, oxazolyl, pyrazolyl, carboxylate, pyridinyl, thiazolyl, substituted or unsubstituted thiophenyl (e.g., carboxylate substituted thiophenyl), piperidinylcarbonyl, dialkylaminomethyl (e.g., di-n-butylaminomethyl), cyano, substituted or unsubstituted arylthiocarbonyl (e.g., p-methylphenylthiocarbonyl), deuterated alkylaminoalkyl, substituted furanyl (e.g., methoxyalkylaminomethyl substituted furanyl, alkylaminomethyl substituted furanyl or halogenated alkylaminomethyl substituted furanyl, such as fluoroalkylaminomethyl substituted furanyl), isoxolazolyl, cyano substituted pyridinyl, alkylcarbonylamino substituted pyridinyl (such as acylamino substituted pyridinyl), dialkylamino substituted phenyl (e.g., para-dimethylamino substituted phenyl), pyrrolidonylcarbonyl, azepanylcarbonyl, carboxylatecarbonyl, alkylcarbonyl substituted phenyl (e.g., meta-acyl substituted phenyl), aminocarbonyl substituted phenyl (e.g., is para-aminocarbonyl substituted phenyl or meta-aminocarbonyl substituted phenyl), carboxylate substituted phenyl (e.g., meta-carboxylate substituted phenyl) or piperazinylcarbonyl.

Examples of tetracycline compounds of Formula (III) include:

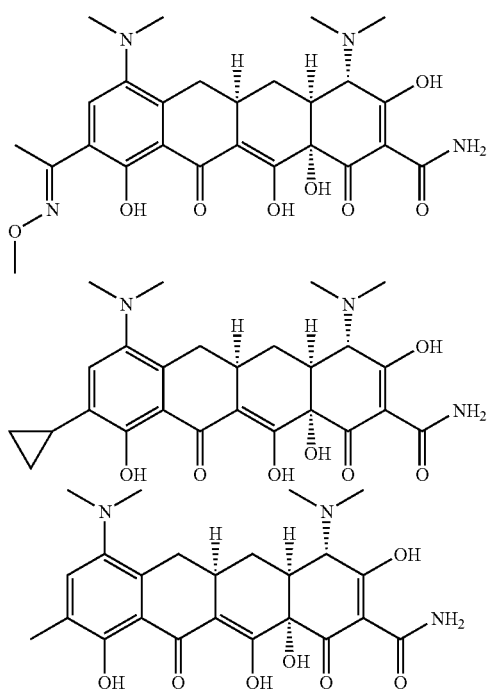

23
-continued
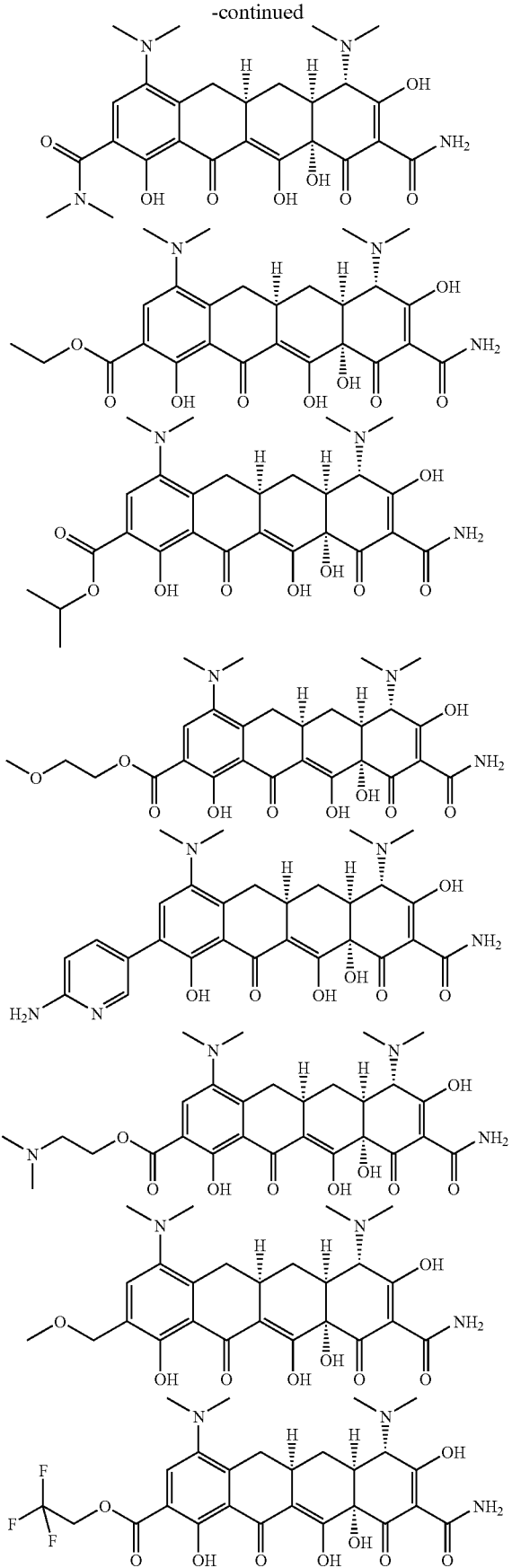
24
-continued
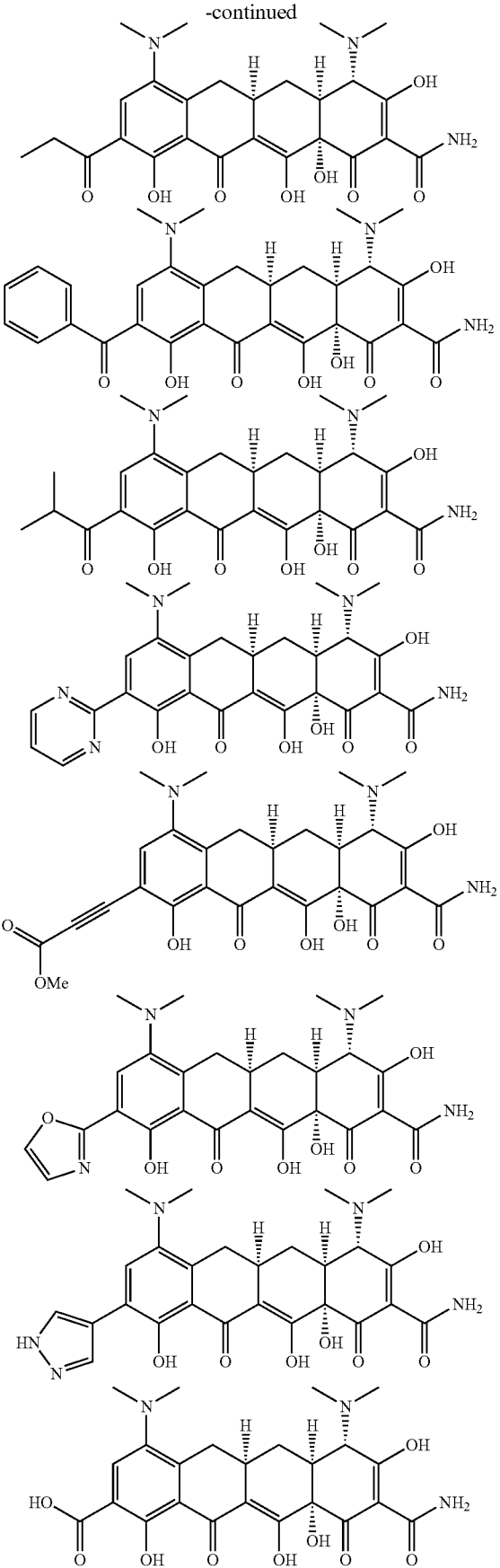

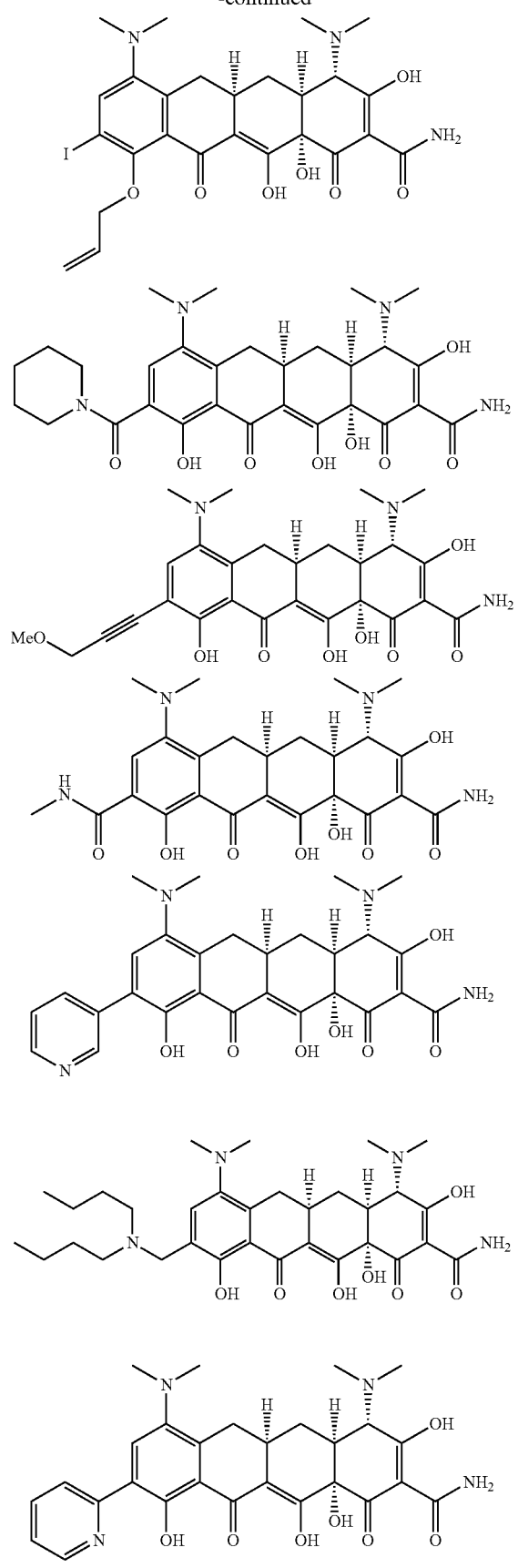
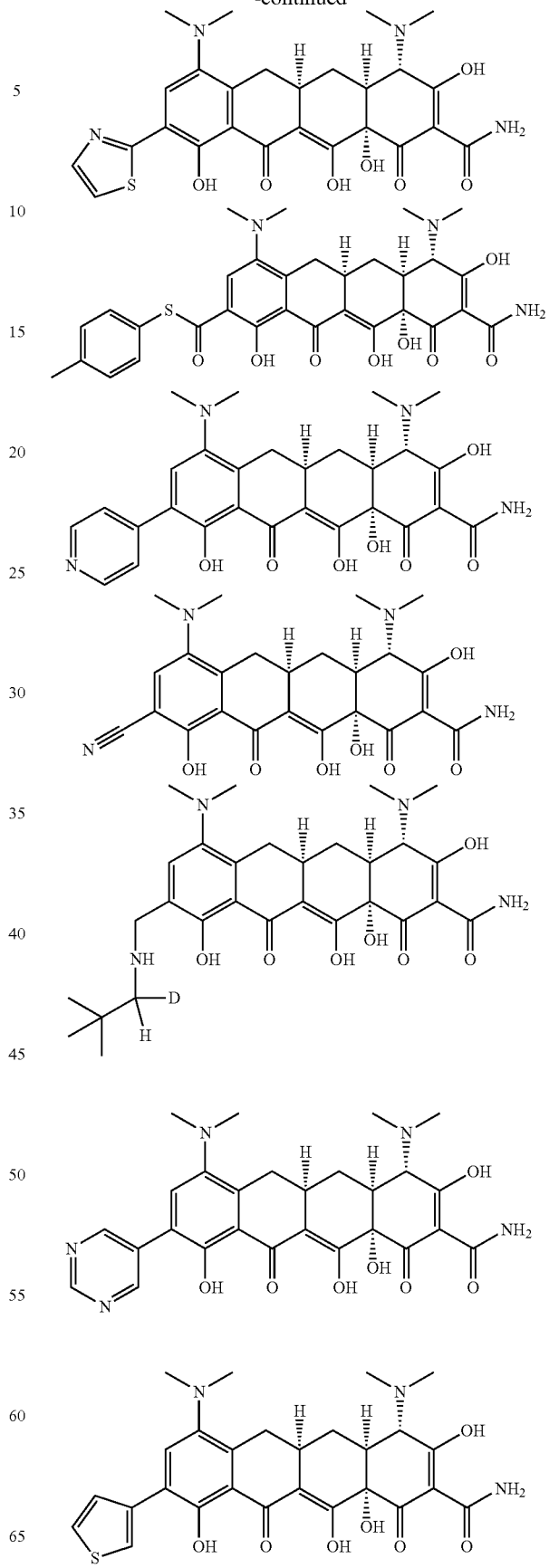

27
-continued
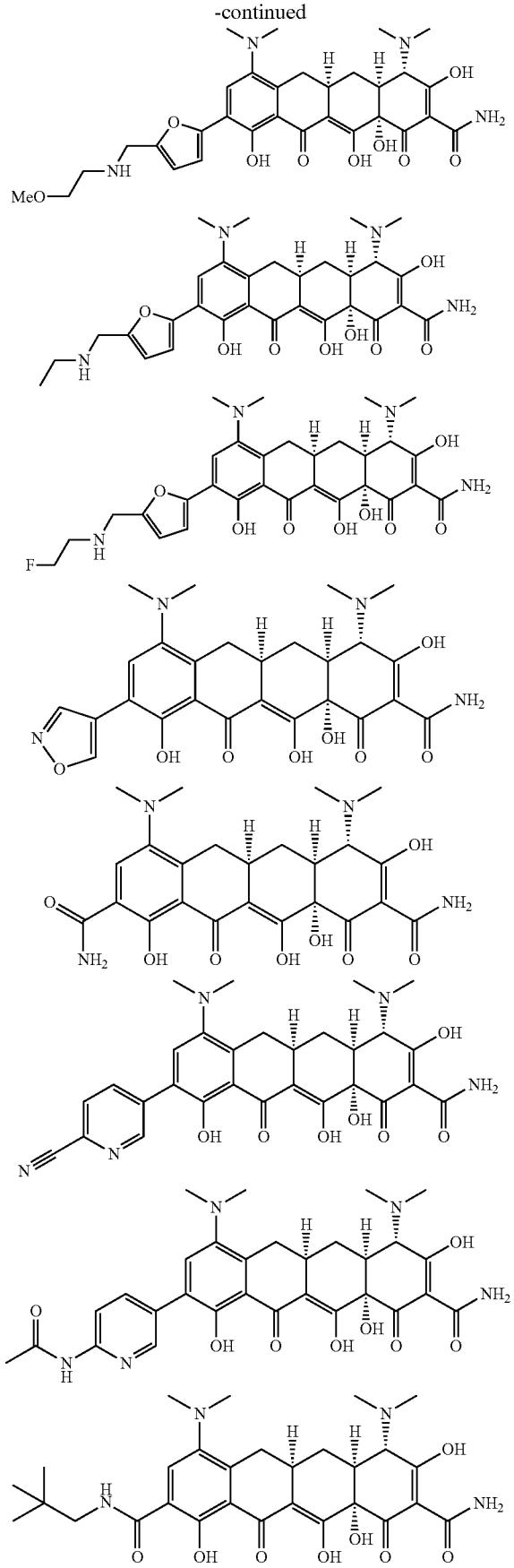
28
-continued
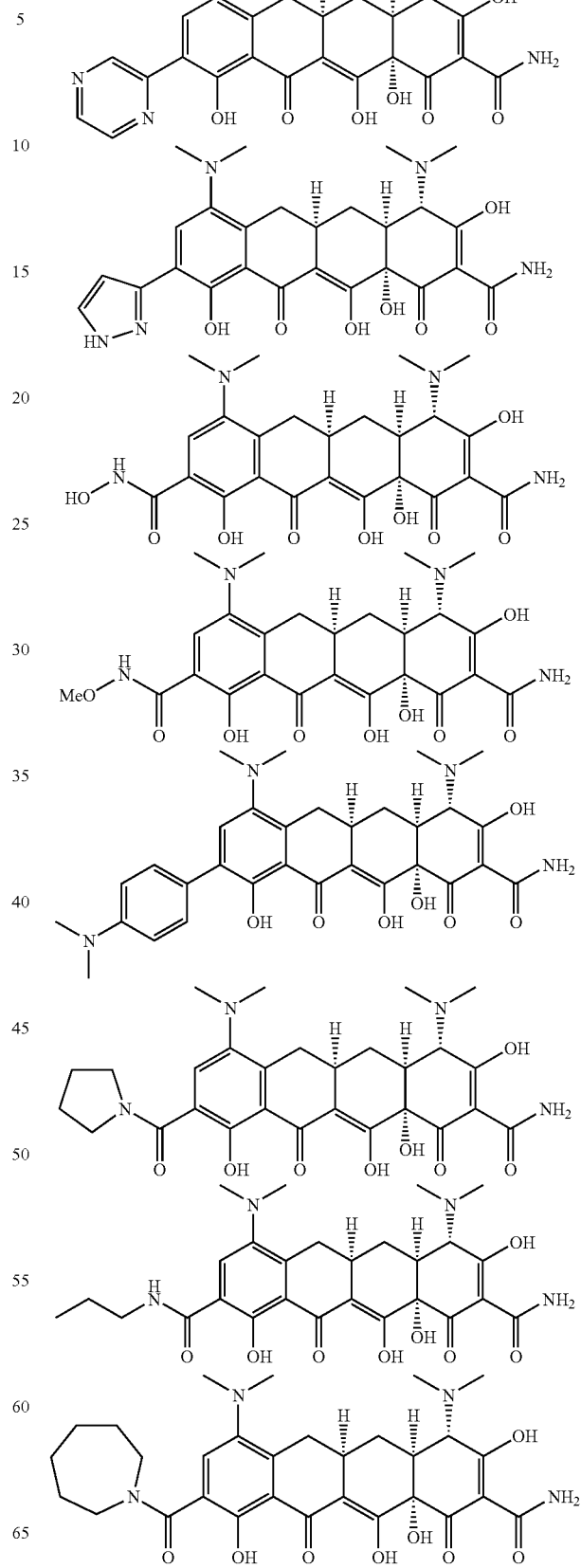

29
-continued
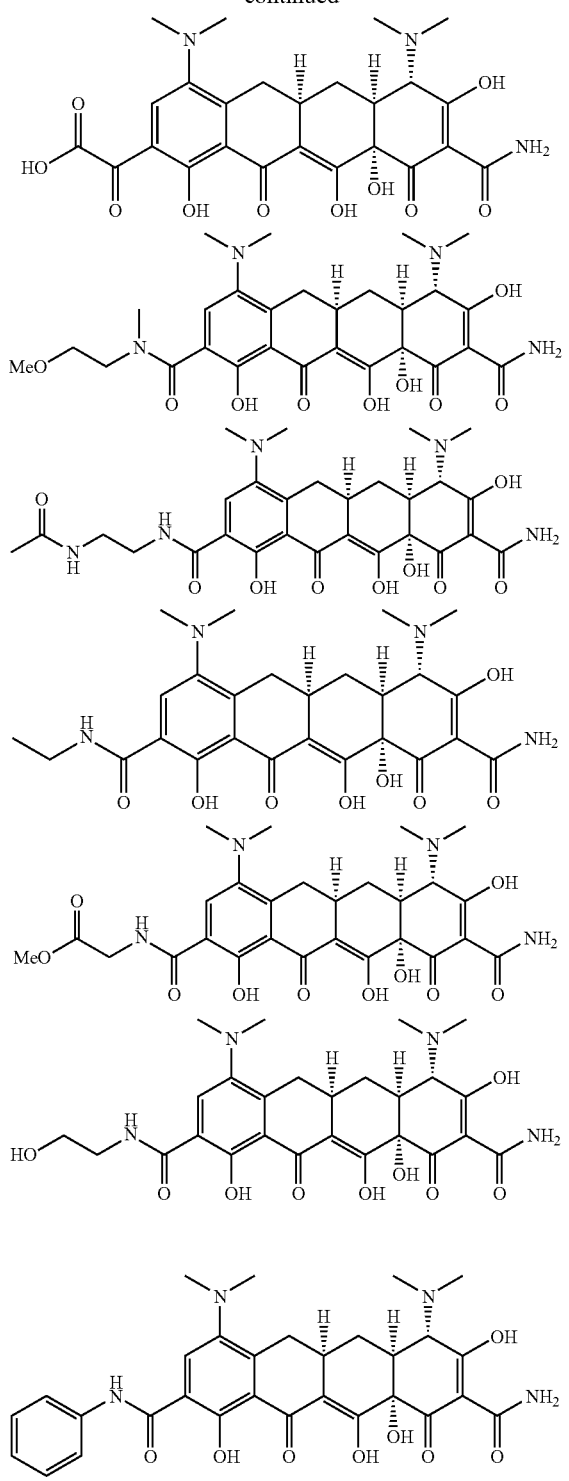
30
-continued
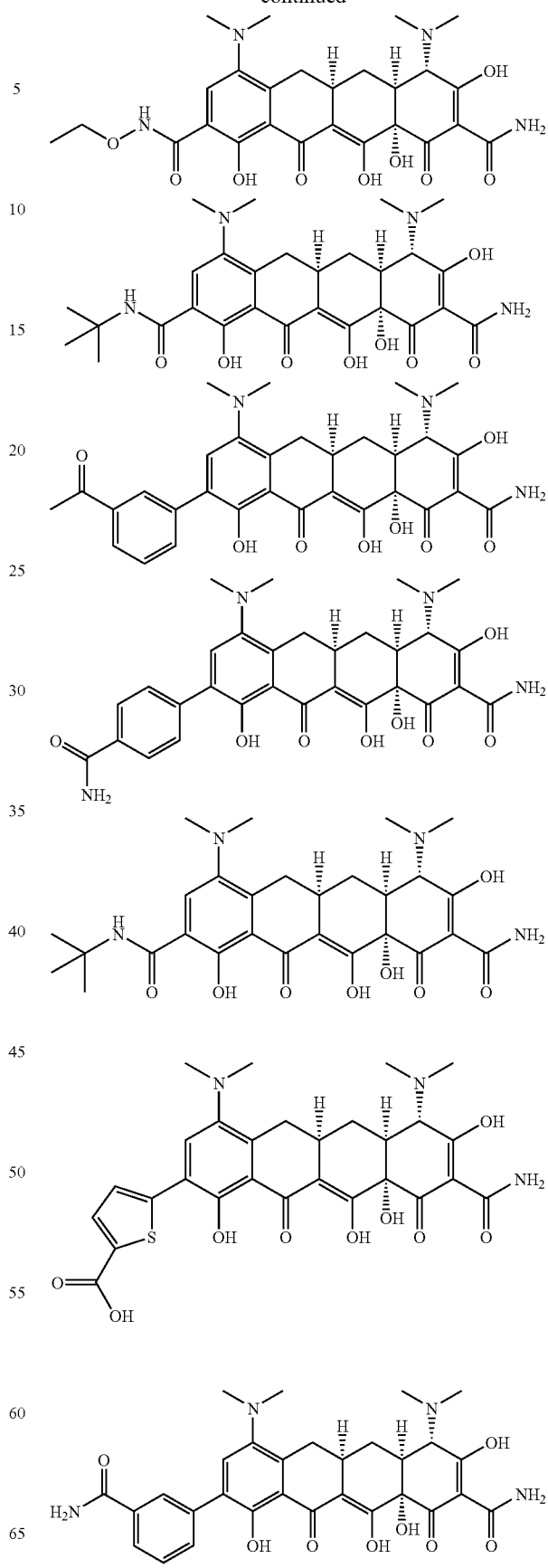

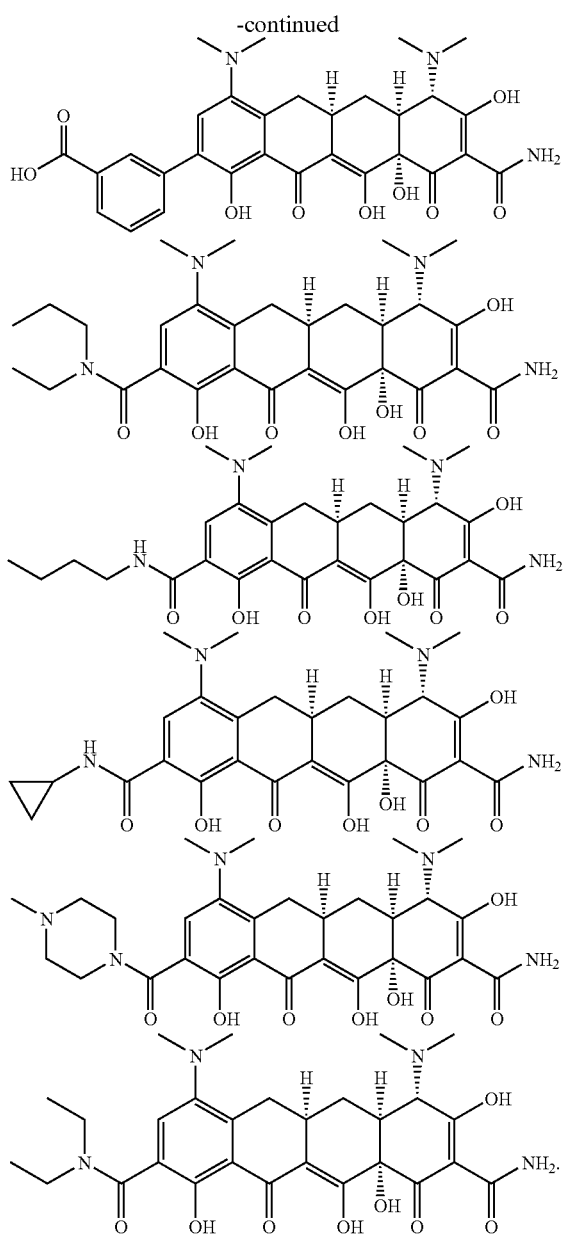

In another embodiment, the invention pertains to tetracycline compounds of Formula (IV):

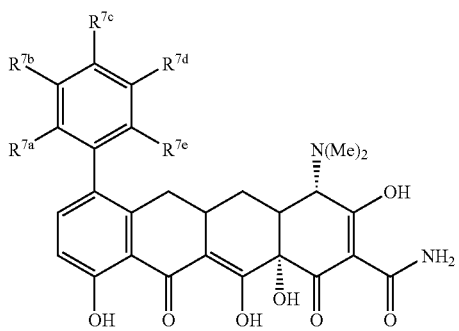

(IV)

wherein $R^{7a}$ is methoxy, dialkylaminomethyl, substituted N-piperdinyl methyl, fluorine, or hydrogen;

$R^{7b}$ is hydrogen;

$R^{7c}$ is alkoxyalkylaminoalkyl, halogenated N-piperdinyl methyl, hydroxyl, dialkylaminoalkylamino, dialkylaminomethyl, substituted N-piperidinyl methyl, substituted N-pyrrolyl methyl, or hydrogen;

$R^{7d}$ is arylalkylaminoalkyl, arylalkyl substituted alkylaminoalkyl, substituted N-piperidinylmethyl, N-piperidinyl substituted aminomethyl, cyclopropylamino methyl, piperdinyl substituted alkyl, dialkylaminomethyl, heteroaryl substituted dialkylaminomethyl, alkylaminomethyl, cycloalkylaminomethyl, alkylaminoethyl, cyano substituted dialkylaminomethyl, N-pyrrolidinyl substituted methyl, N-pyrrolyl substituted methyl, methoxy substituted dialkylaminomethyl, alkoxyalkylaminomethyl, substituted carboxylate alkylaminomethyl, hydrogen or linked with $R^{7c}$ by a —O—CH$_2$—O— linker;

$R^{7e}$ is hydrogen, and pharmaceutically acceptable salts, esters and prodrugs thereof, provided that each of $R^{7a}$, $R^{7b}$, $R^{7c}$, $R^{7d}$, and $R^{7e}$ are not hydrogen.

In one embodiment, $R^{7e}$ is hydrogen and $R^{7b}$ and $R^{7c}$ are each hydrogen. In a further embodiment, $R^{7a}$ is methoxy and $R^{7d}$ is substituted N-piperidinylmethyl, $R^{7a}$ is halogen (e.g., fluorine) and $R^{7d}$ is substituted N-piperidinylmethyl or $R^{7a}$ is methoxy and $R^{7d}$ is arylalkyl substituted alkylaminoalkyl, such as phenylmethyl substituted alkylaminoalkyl In another embodiment, $R^{7e}$ and $R^{7a}$, $R^{7b}$ and $R^{7c}$ are each hydrogen. In a further embodiment, $R^{7d}$ is dialkylaminomethyl, for example, methylisopropylaminomethyl, methylcyclohexylaminomethyl, methylethylaminomethyl, methylpropylaminomethyl, methylisobutylaminomethyl, propylisopropylaminomethyl, ethylisopropylaminomethyl, propylcyclopropylmethylaminomethyl, cyano-substituted ethylmethylaminomethyl, methoxy-substituted ethylaminomethyl, t-butoxy substituted ethylmethylaminomethyl or pyridine substituted methymethylaminomethyl. In another embodiment, $R^{7d}$ is substituted N-piperidinylmethyl, such as dimethyl substituted N-piperidinylmethyl, trifluoromethyl substituted N-piperidinylmethyl or halogen (e.g., fluorine) substituted N-piperidinylmethyl, cycloalkylaminomethyl (e.g., cyclopropylaminomethyl, dimethylpyrrolidinylaminomethyl or dimethylpyrrolylaminomethyl) or alkylaminomethyl (e.g., t-butylmethylaminomethyl).

In yet another embodiment, $R^{7e}$ and $R^{7a}$, $R^{7b}$ and $R^{7d}$ are each hydrogen. In a further embodiment, $R^{7c}$ is alkoxyalkylaminoalkyl (e.g., methoxyalkylaminoalkyl), hydroxy, dialkylaminoalkylamino (e.g., diisopropylaminomethyl), dialkylaminomethyl, substituted N-piperidinylmethyl, substituted N-pyrrolyl or substituted carboxylate alkylaminomethyl, In another embodiment, $R^{7e}$ and $R^{7b}$, $R^{7c}$ and $R^{7d}$ are each hydrogen. In a further embodiment, $R^{7a}$ is dialkylaminomethyl, such as dimethylaminomethyl.

In yet another embodiment, $R^{7e}$ and $R^{7b}$ are each hydrogen and $R^{7a}$ is substituted N-piperidinylmethyl and $R^{7d}$ is linked with $R^{7c}$ by a —CH$_2$—O— linker.

Examples of tetracycline compounds of Formula (IV) include:
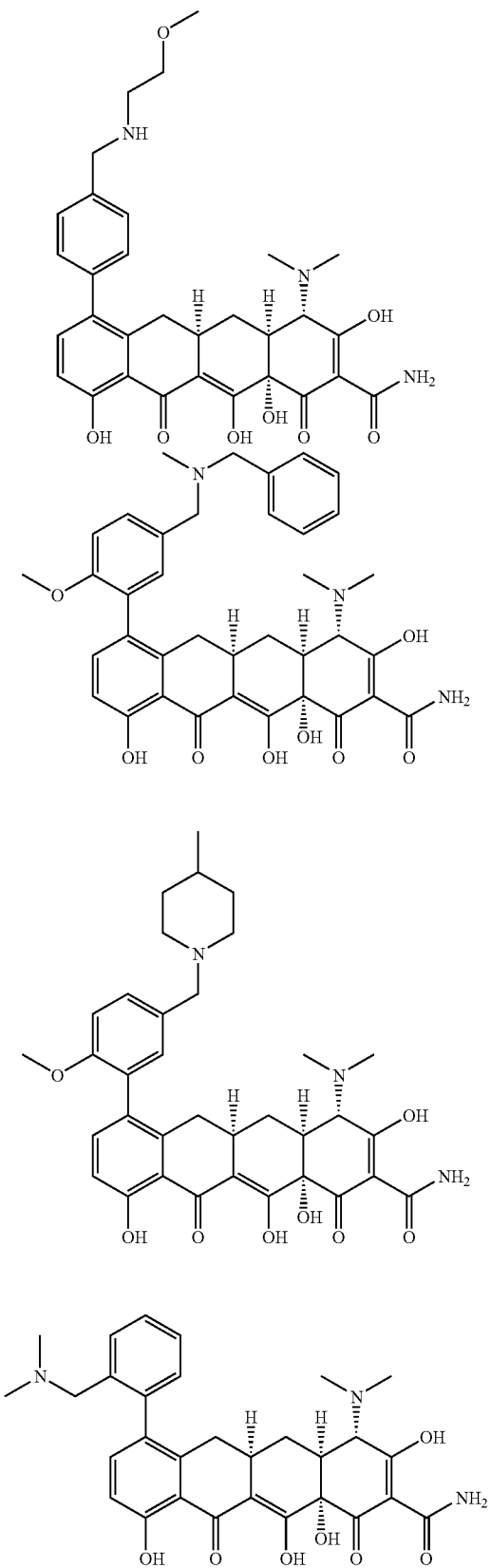
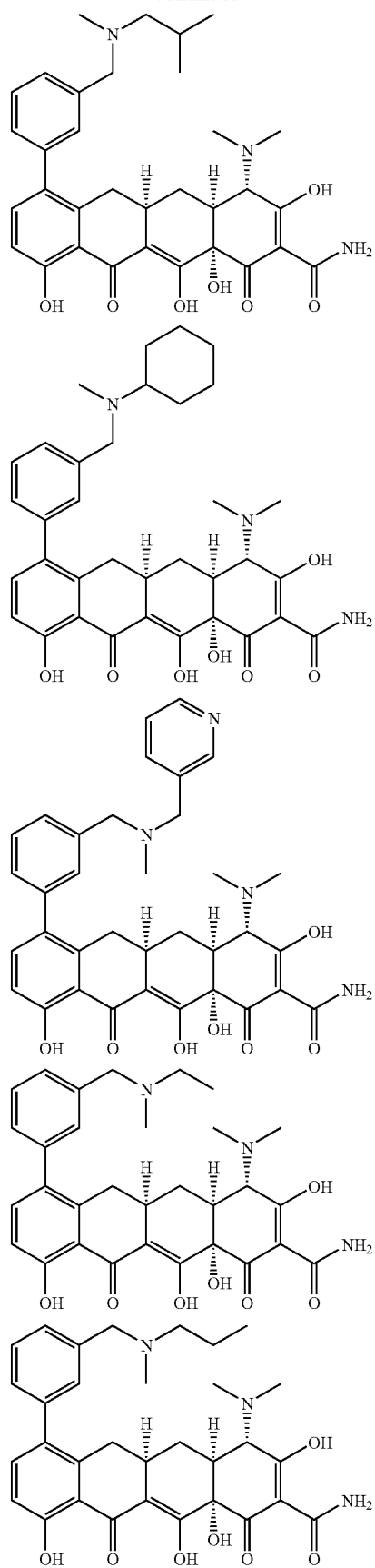

35
-continued
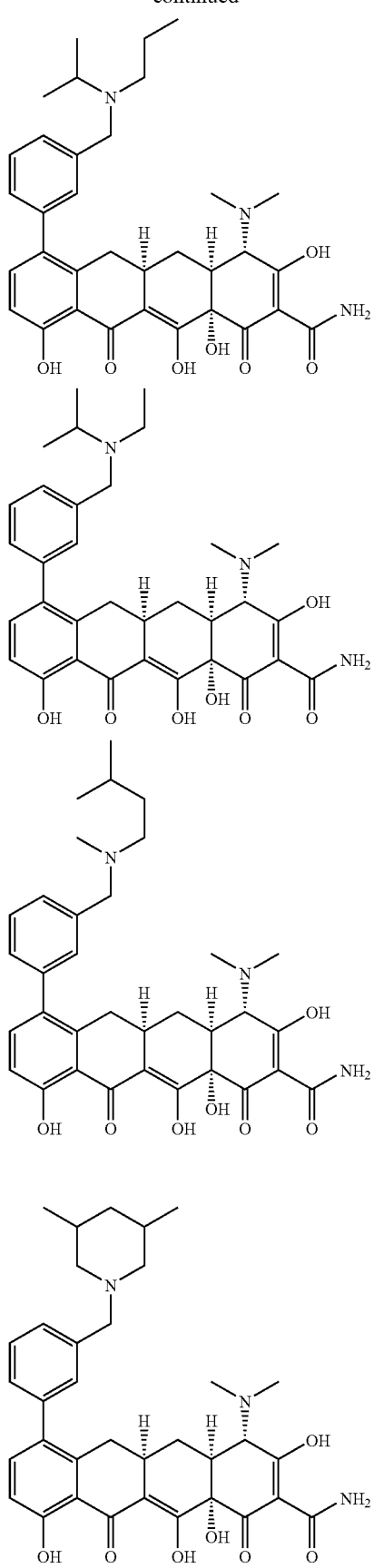
36
-continued
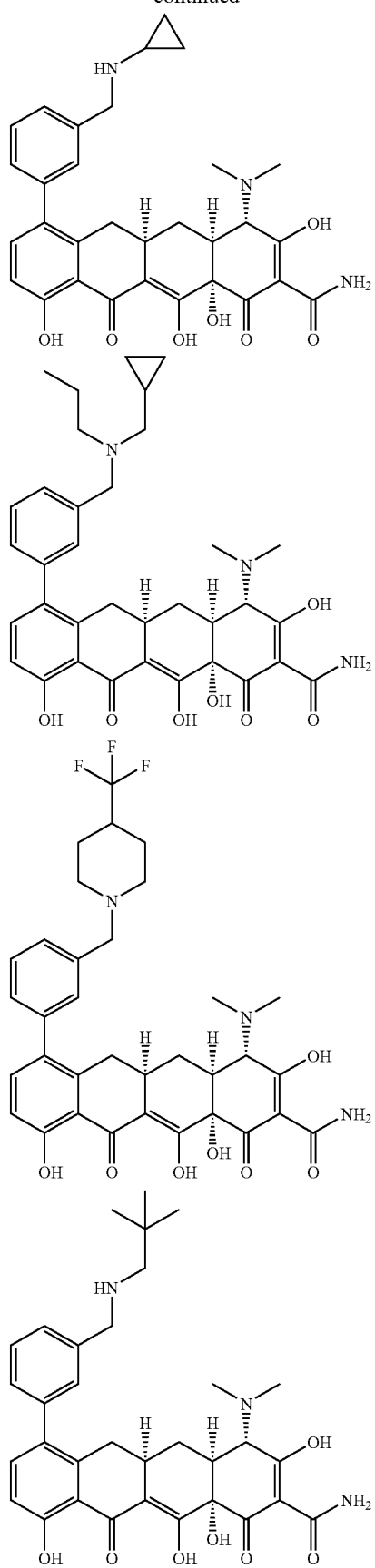

37
-continued
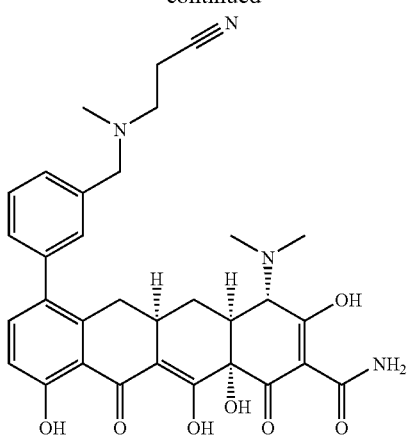
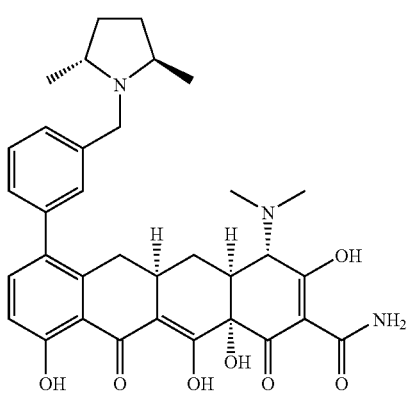
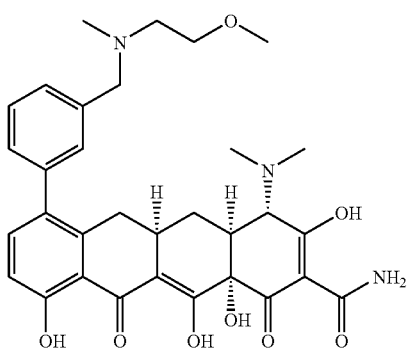
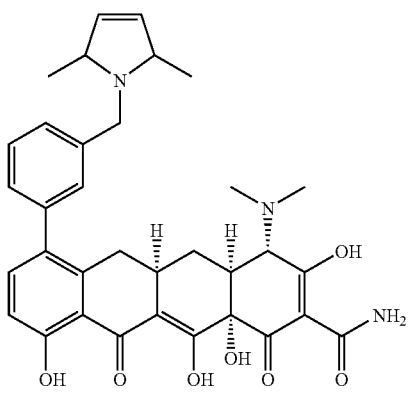
38
-continued
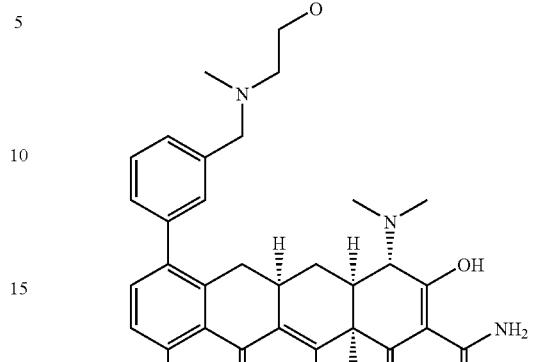
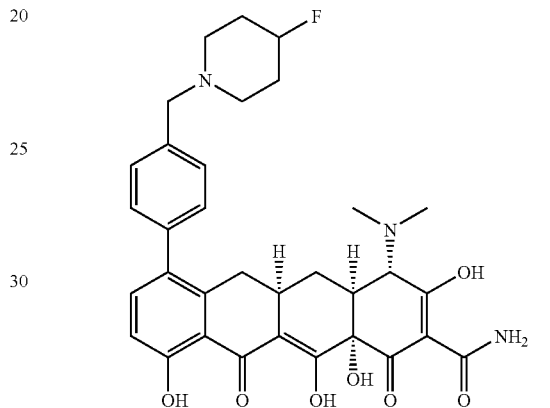
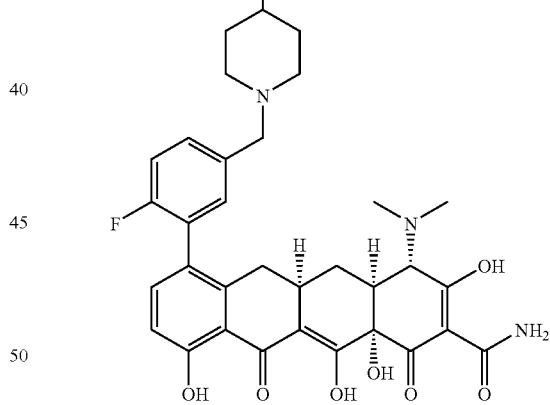
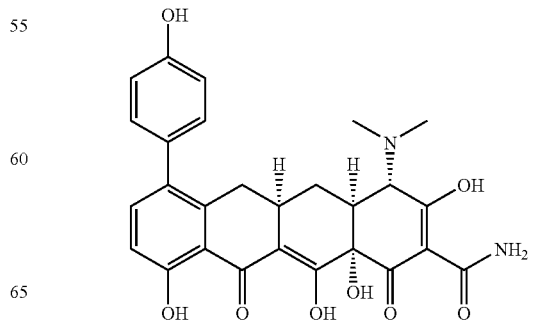

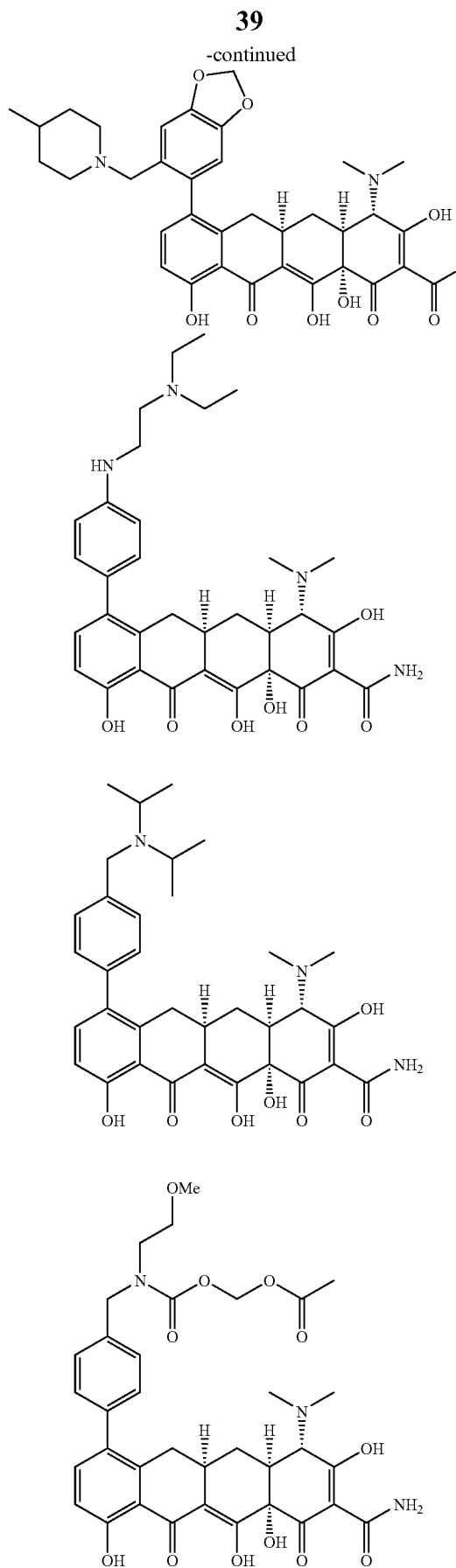
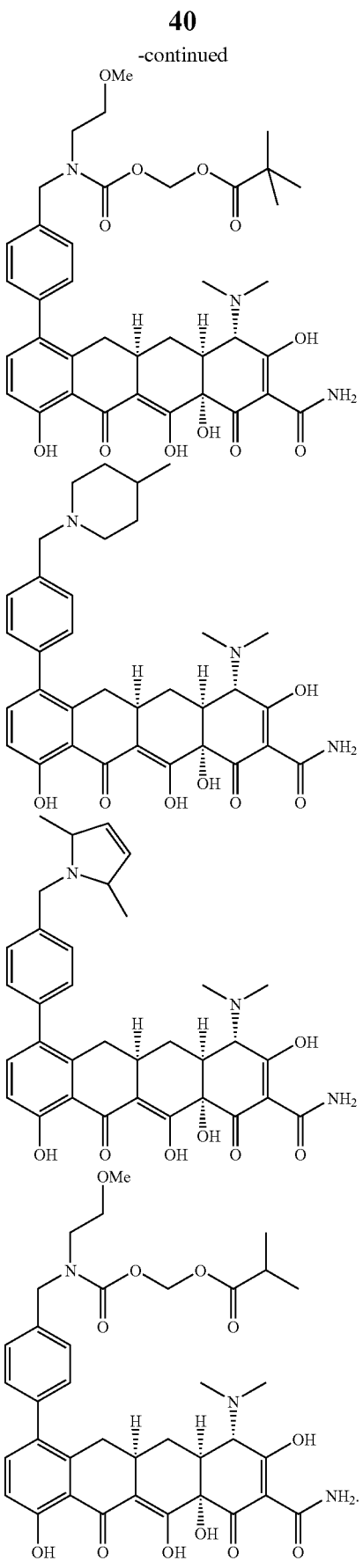

In another embodiment, the invention pertains to tetracycline compounds of Formula (V):

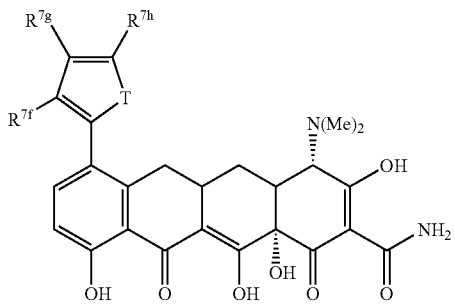

wherein

T is NH or O;

$R^{7f}$ is dialkylaminoalkyl, N-piperidinylamino alkyl, substituted or unsubstituted N-piperdinylalkyl, N-pyrrolidinylamino alkyl, substituted or unsubstituted N-pyrrolidinylalkyl, substituted or unsubstituted N-pyrrolylalkyl, alkenenyl substituted dialkylaminoalkyl, N-decahydroisoquinolinylalkyl, alkoxyalkylaminoalkyl, or hydrogen;

$R^{7g}$ is hydrogen;

$R^{7h}$ is heteroaryl substituted alkylaminoalkyl, dialkylaminoalkyl, substituted N-piperidinylalkyl or hydrogen, and pharmaceutically acceptable salts, esters and prodrugs thereof, provided that each of $R^{7f}$, $R^{7g}$, and $R^{7h}$ are not hydrogen.

In one embodiment, T is NH and $R^{7f}$ and $R^{7g}$ are each hydrogen. In a further embodiment, $R^{7h}$ is dialkylaminoalkyl (e.g., dimethylaminomethyl) or substituted N-piperidinylalkyl (e.g., methyl substituted N-piperidinylmethyl).

In another embodiment, T is O and $R^{7f}$ and $R^{7g}$ are each hydrogen. In a further embodiment, $R^{7h}$ is heteroaryl substituted alkylaminoalkyl, such as, for example, pyridinyl substituted methylaminomethyl or methyl substituted isoxazolylmethylaminomethyl.

In yet another embodiment, T is O and $R^{7g}$ and $R^{7h}$ are each hydrogen. In a further embodiment, $R^{7f}$ is dialkylaminoalkyl (e.g., methylisopropylaminomethyl or allylmethylaminomethyl), substituted N-piperidinylalkyl (e.g., methyl substituted N-piperidinylmethyl or halogen substituted N-piperidinylmethyl, such as fluorine substituted N-piperidinylmethyl) substituted N-pyrrolylalkyl (e.g., methyl substituted N-pyrrolylmethyl), substituted N-pyrrolidinylalkyl (e.g., methyl substituted N-pyrrolidinylmethyl), N-decahydroisoquinolinylalkyl or alkoxyalkylaminoalkyl (e.g., methoxyalkylaminomethyl).

Examples of tetracycline compounds of Formula (V) include:

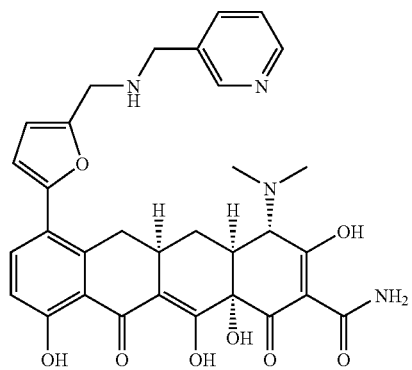

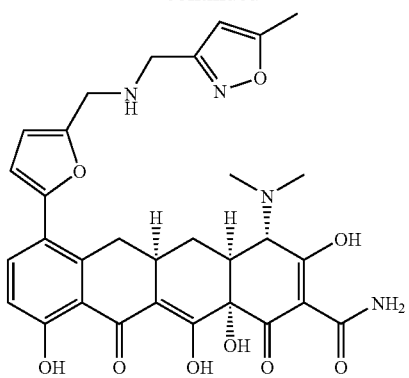

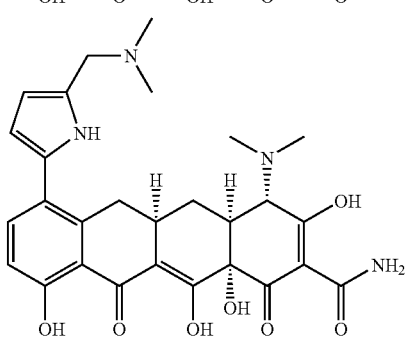

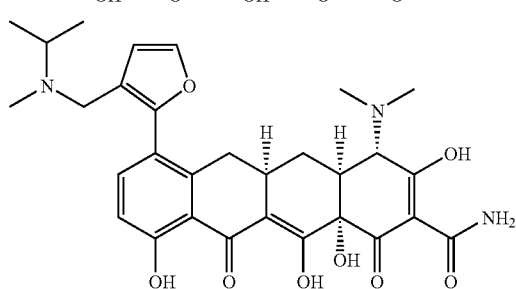

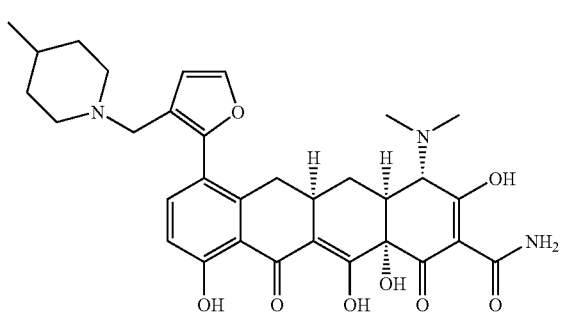

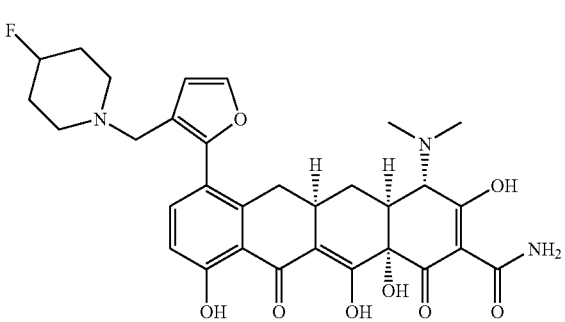

-continued

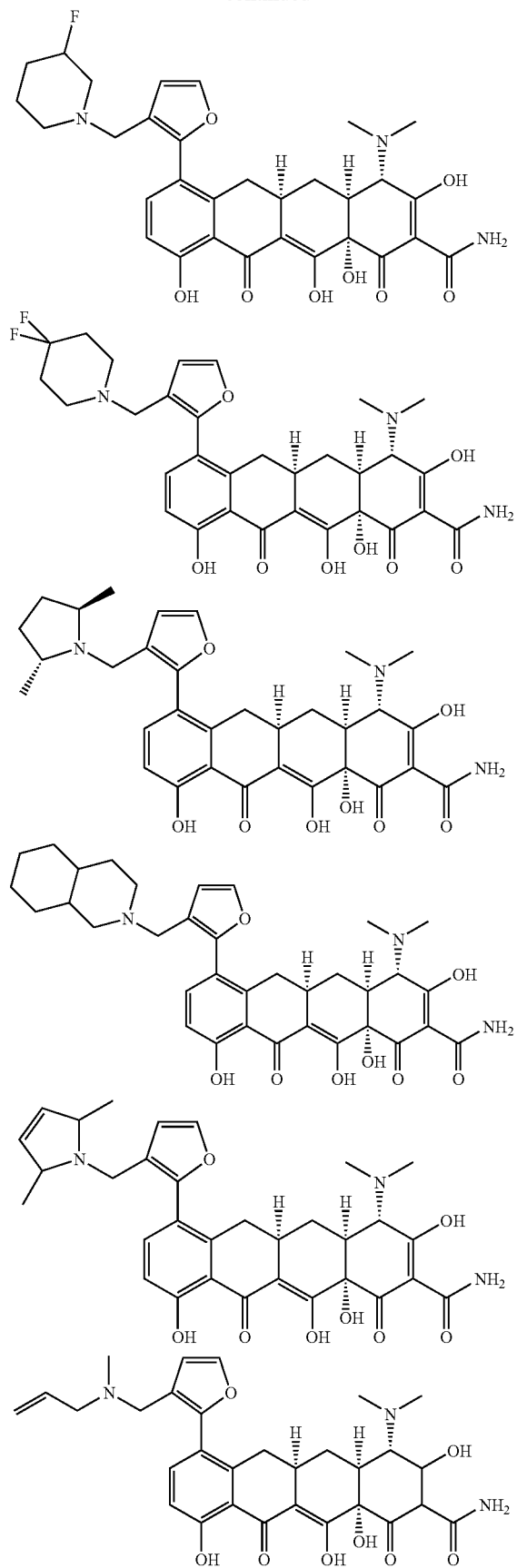

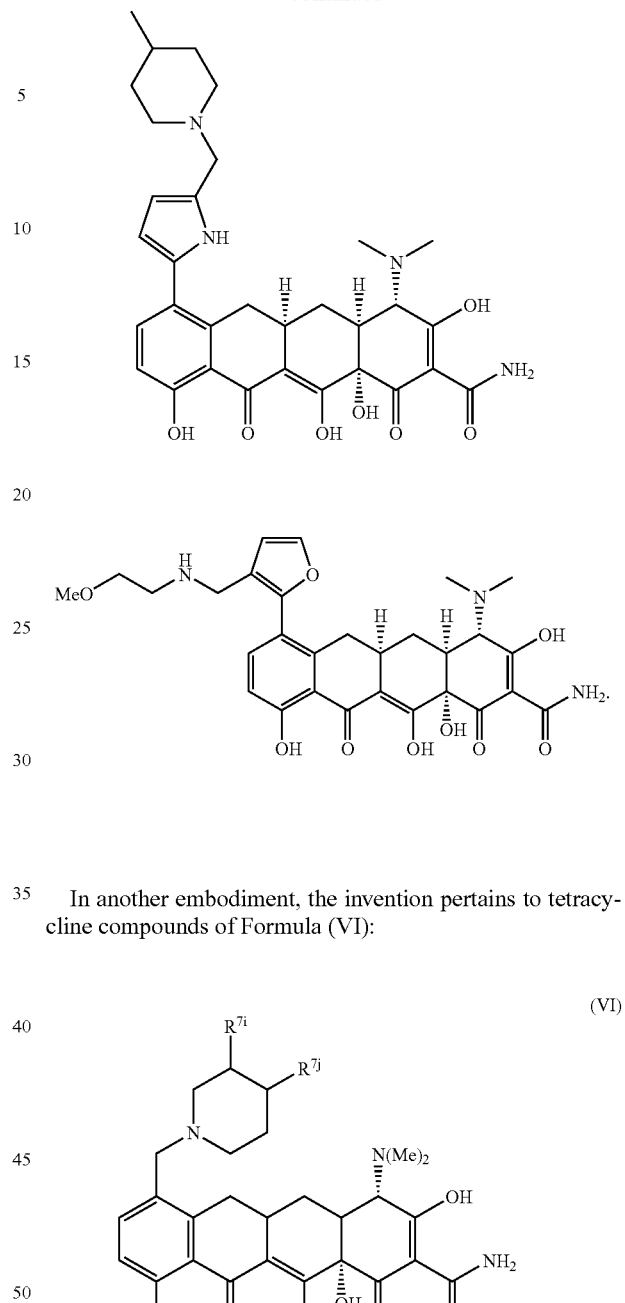

In another embodiment, the invention pertains to tetracycline compounds of Formula (VI):

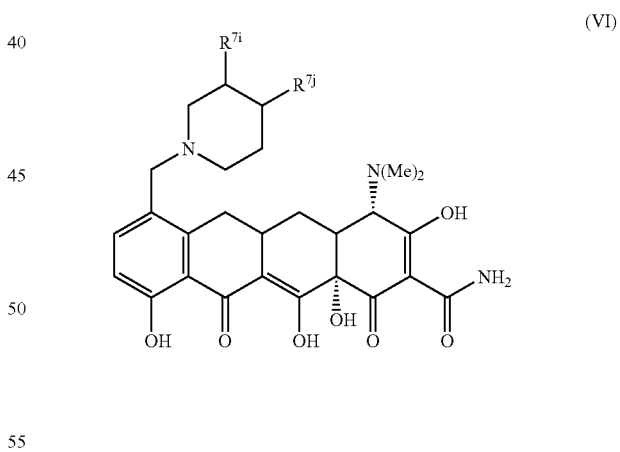

(VI)

wherein $R^{7i}$ is fluorine or hydrogen;

$R^{7j}$ is trifluoromethyl, alkyloxycarbonyl, methyl, cyano, or hydrogen, and pharmaceutically acceptable salts, esters and prodrugs thereof, provided that both of $R^{7i}$ and $R^{7j}$ are not hydrogen.

In one embodiment, $R^{7i}$ is hydrogen. In a further embodiment, $R^{7j}$ is methyl, cyano, trifluoromethyl, or alkyloxycarbonyl, such as, for example, methoxycarbonyl.

In another embodiment, $R^{7i}$ is fluorine and $R^{7j}$ is hydrogen.

Examples of tetracycline compounds of Formula (VI) include:

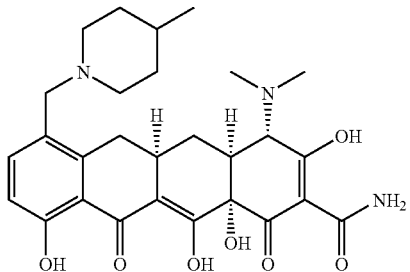

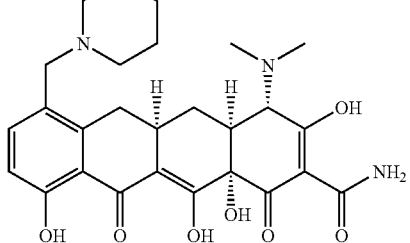

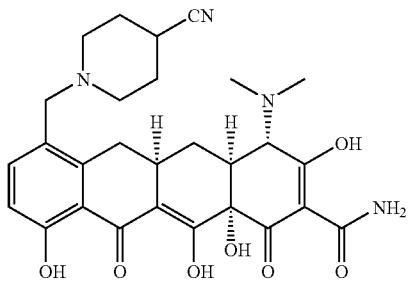

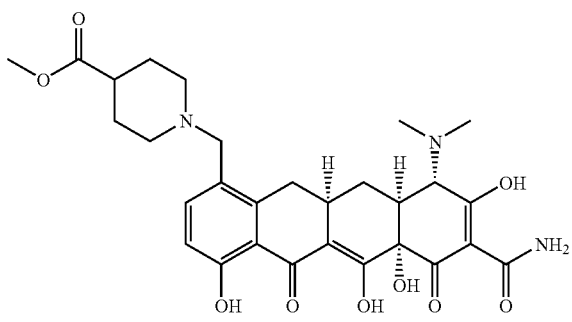

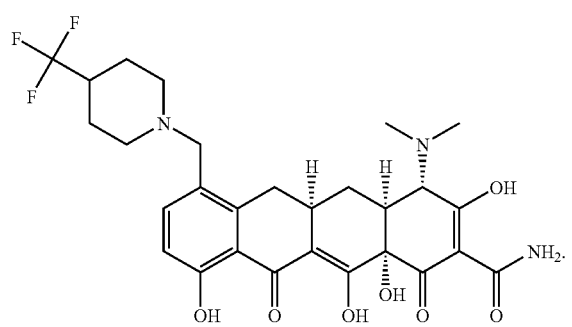

In another embodiment, the invention pertains to tetracycline compounds of Formula (VII):

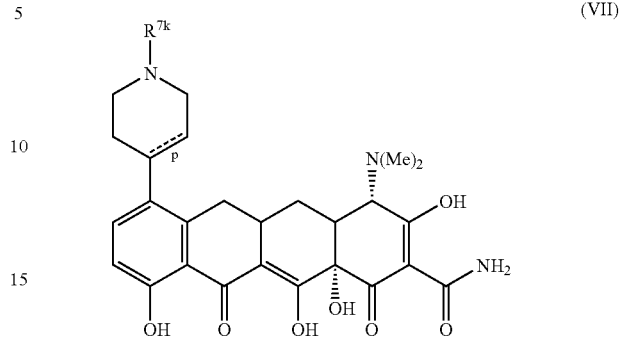

(VII)

wherein p is a single or double bond;

$R^{7k}$ is alkyl, cycloalkyl, dialkylaminoalkylcarbonyl, alkoxyalkylcarbonyl, halogen substituted alkyl, halogen substituted cycloalkyl, or hydrogen, and pharmaceutically acceptable salts, esters and prodrugs thereof.

In one embodiment, p is a single bond and $R^{7k}$ is alkyl, such as isopropyl, or hydrogen.

In another embodiment, p is a double bond. In a further embodiment, $R^{7k}$ is hydrogen, alkyl (e.g., isopropyl), cycloalkyl (e.g., cyclohexyl or cyclopropylmethyl), halogen substituted alkyl (e.g., trifluoromethyl substituted propyl), halogen substituted cycloalkyl (e.g., trifluoromethyl substituted cyclohexyl), alkoxyalkylcarbonyl (e.g., methoxymethylcarbonyl) or dialkylaminoalkylcarbonyl (e.g., dimethylaminomethylcarbonyl).

Examples of tetracycline compounds of Formula (VII) include:

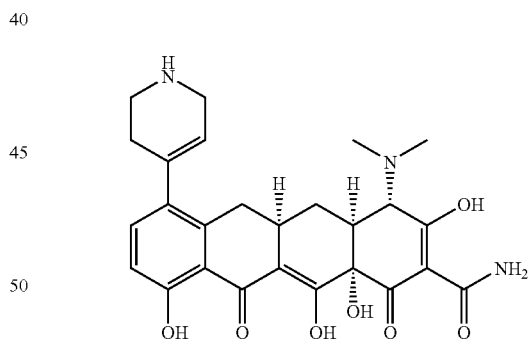

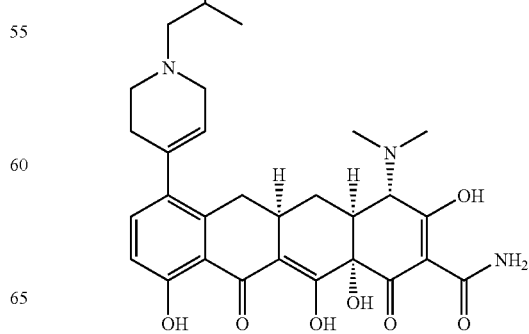

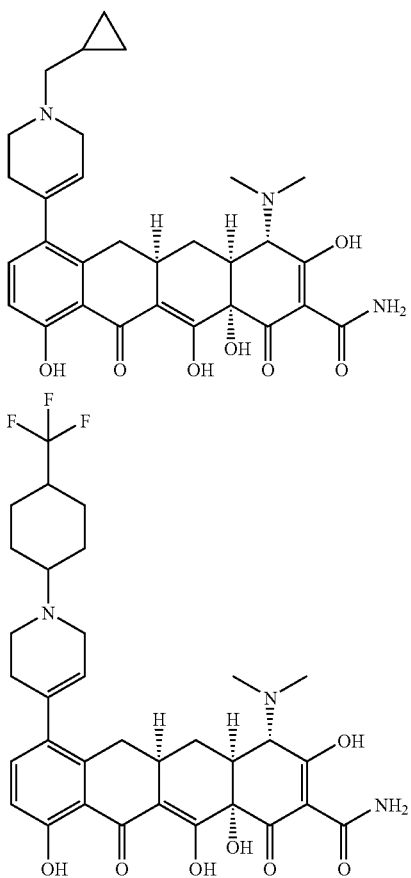
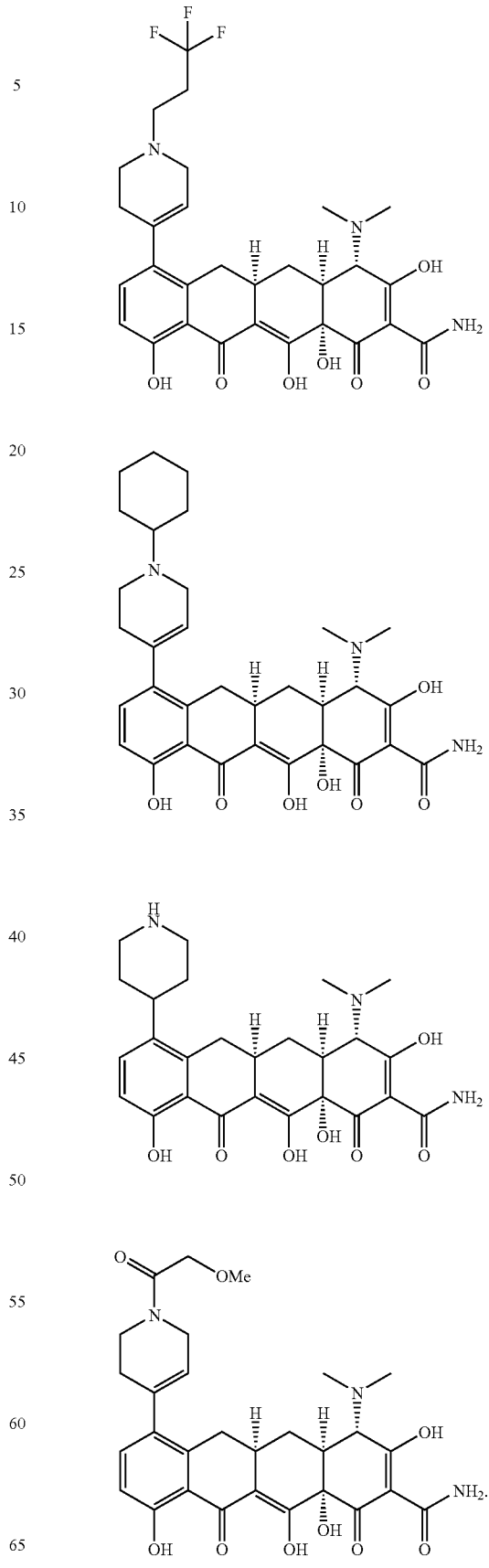

In another embodiment, the invention pertains to tetracycline compounds of Formula (VIII):

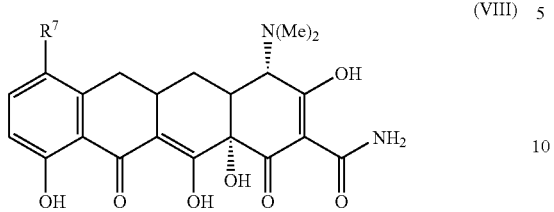

wherein

R⁷ is fluoro substituted N-pyrrolidinylalkyl, N-piperidinylalkylcarbonyl, dialkylaminoalkylaminocarbonyl, aminoalkyl, N-pyrroyl alkyl, dialkylamino substituted pyridinyl, substituted or unsubtituted phenyl substituted N-piperizinyl alkyl, alkylaminoalkyl, alkoxy substituted pyrimidinyl, 1-H-pyrimidin-2-onyl, cyano substituted pyridinyl, substituted or unsubstituted N-pyrrolidinyl alkyl, halogen substituted pyridinyl, substituted or unsubstituted arylalkylamino alkyl, alkoxyalkylaminoalkyl, N-imidizolylalkylcarbonyl, N-dihydroimidizolylalkylcarbonyl, alkylaminoalkyl, imidizopyrimidinyl, substituted or unsubstituted imidizopyridinyl, or substituted or unsubstituted pyrizinyl substituted alkylaminoalkyl, alkoxyalkylcarbonyl; and pharmaceutically acceptable salts, esters and prodrugs thereof.

In one embodiment, the fluoro substituted N-pyrrolidinylalkyl is difluoro substituted N-pyrrolidinylmethyl.

In another embodiment, the aminoalkyl is aminomethyl.

In yet another embodiment, the N-pyrroyl alkyl is N-pyrroyl methyl.

In another embodiment, the dialkylamino substituted pyridinyl is dimethylamino substituted pyridinyl.

In a further embodiment, the substituted phenyl substituted N-piperizinyl alkyl is para-fluorophenyl substituted phenyl N-piperizinyl methyl.

In one embodiment, the alkoxy substituted pyrimidinyl is methoxy substituted pyrimidinyl.

In another embodiment, the substituted N-pyrrolidinyl alkyl is dimethyl substituted N-pyrrolidinyl methyl.

In yet another embodiment, the halogen substituted pyridiyl is fluorine substituted pyridinyl.

In another embodiment, the arylalkylamino alkyl is phenylmethylaminomethyl.

In one embodiment, the alkoxyalkylaminoalkyl is methoxyalkylaminomethyl.

In another embodiment, the alkylaminoalkyl is methylaminomethyl.

In yet another embodiment, the substituted arylalkylamino alkyl is hydroxy substituted phenylmethylamino methyl.

In another embodiment, the substituted pyrizinyl substituted amino alkyl is methyl pyrizinyl substituted methylaminomethyl.

In yet another embodiment, the substituted imidizopyridinyl is halogen substituted imidizopyridinyl, for example, fluorine substituted imidizopyridinyl.

In one embodiment, the alkoxyalkylcarbonyl is methoxymethylcarbonyl.

Examples of tetracycline compounds of Formula (VIII) include:

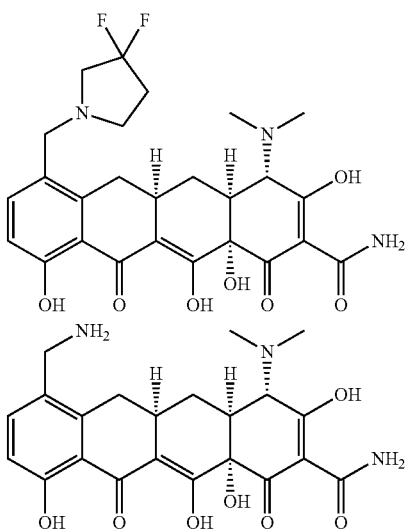

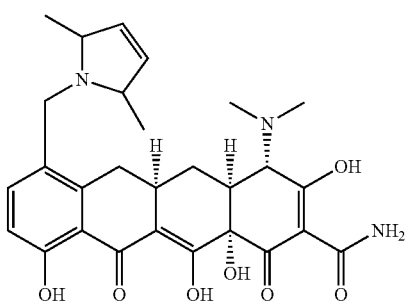

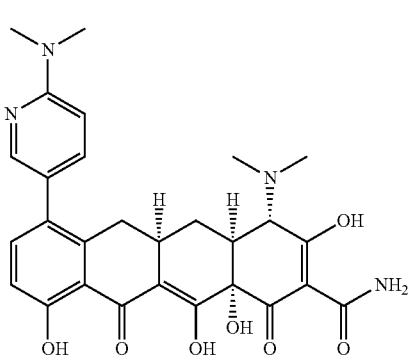

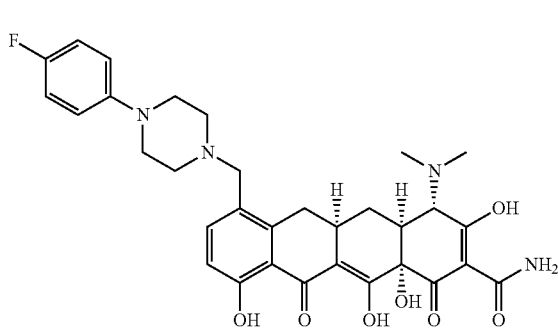

51
-continued
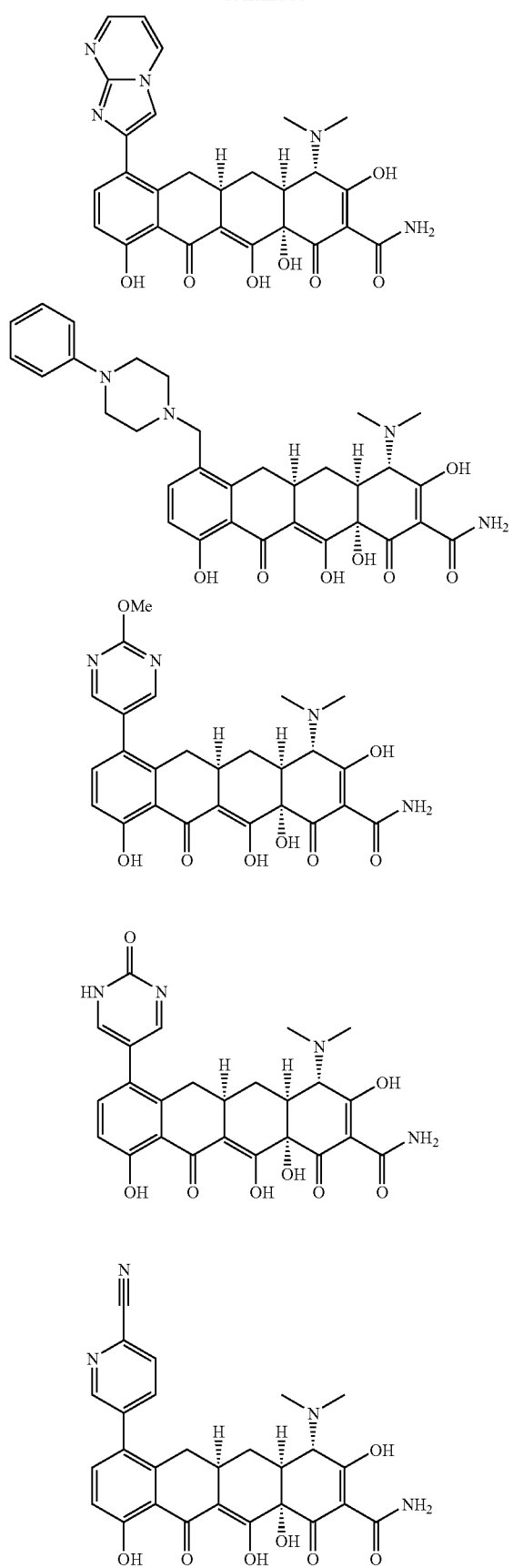
52
-continued
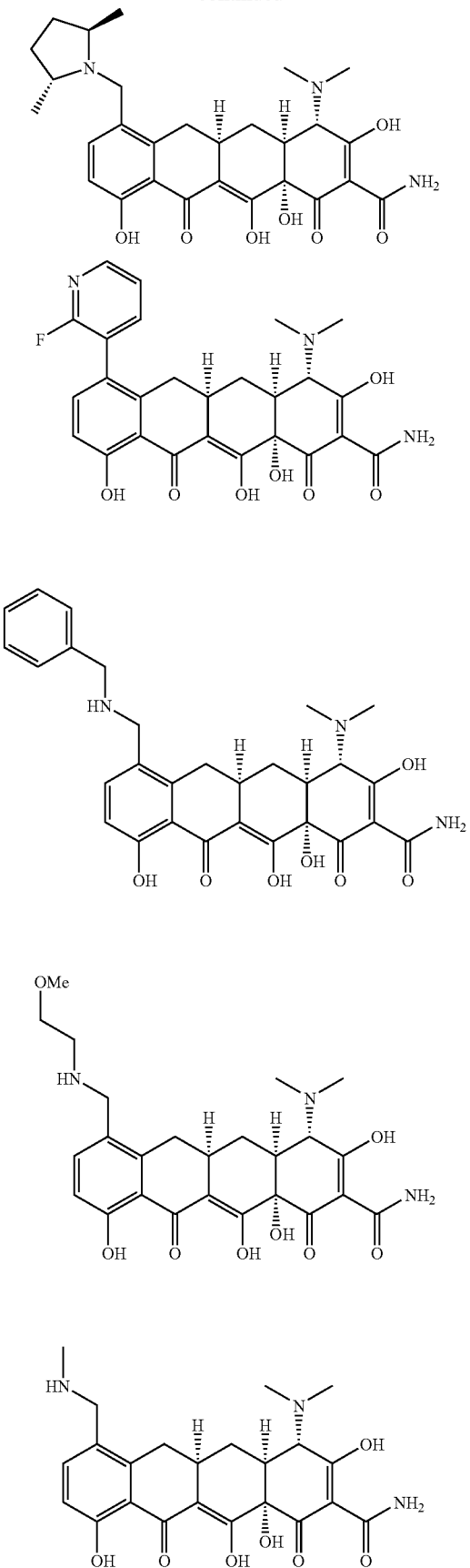

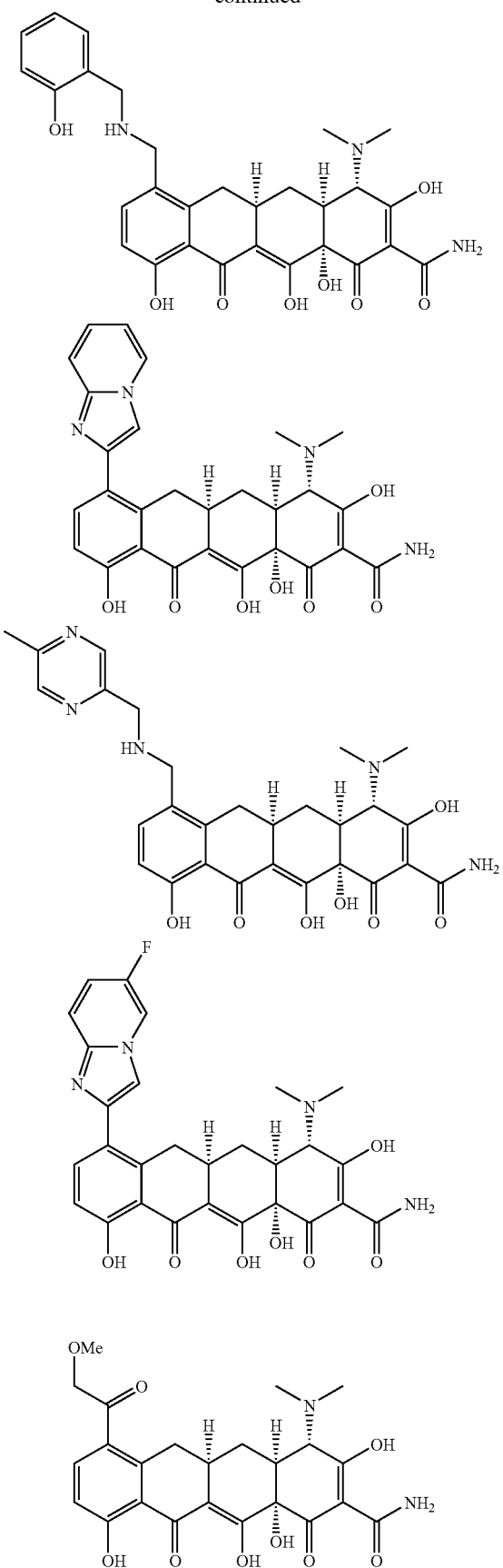

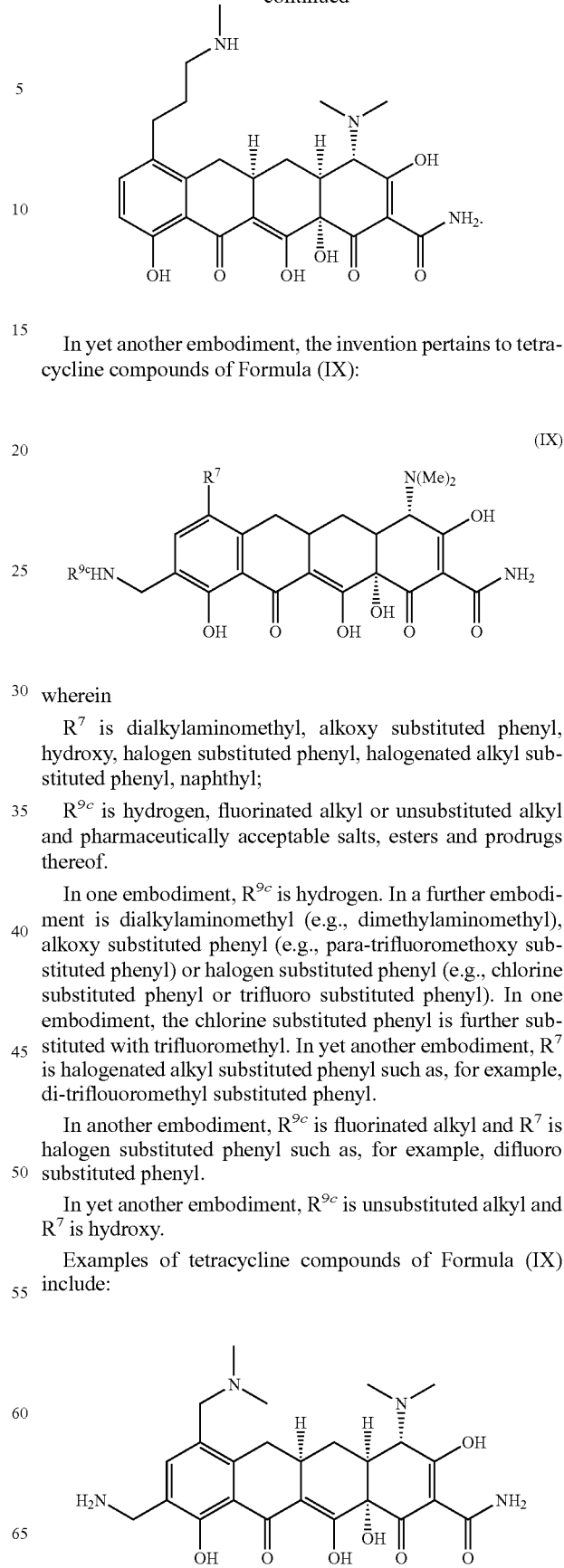

In yet another embodiment, the invention pertains to tetracycline compounds of Formula (IX):

(IX)

wherein $R^7$ is dialkylaminomethyl, alkoxy substituted phenyl, hydroxy, halogen substituted phenyl, halogenated alkyl substituted phenyl, naphthyl;

$R^{9c}$ is hydrogen, fluorinated alkyl or unsubstituted alkyl and pharmaceutically acceptable salts, esters and prodrugs thereof.

In one embodiment, $R^{9c}$ is hydrogen. In a further embodiment is dialkylaminomethyl (e.g., dimethylaminomethyl), alkoxy substituted phenyl (e.g., para-trifluoromethoxy substituted phenyl) or halogen substituted phenyl (e.g., chlorine substituted phenyl or trifluoro substituted phenyl). In one embodiment, the chlorine substituted phenyl is further substituted with trifluoromethyl. In yet another embodiment, $R^7$ is halogenated alkyl substituted phenyl such as, for example, di-triflouoromethyl substituted phenyl.

In another embodiment, $R^{9c}$ is fluorinated alkyl and $R^7$ is halogen substituted phenyl such as, for example, difluoro substituted phenyl.

In yet another embodiment, $R^{9c}$ is unsubstituted alkyl and $R^7$ is hydroxy.

Examples of tetracycline compounds of Formula (IX) include:

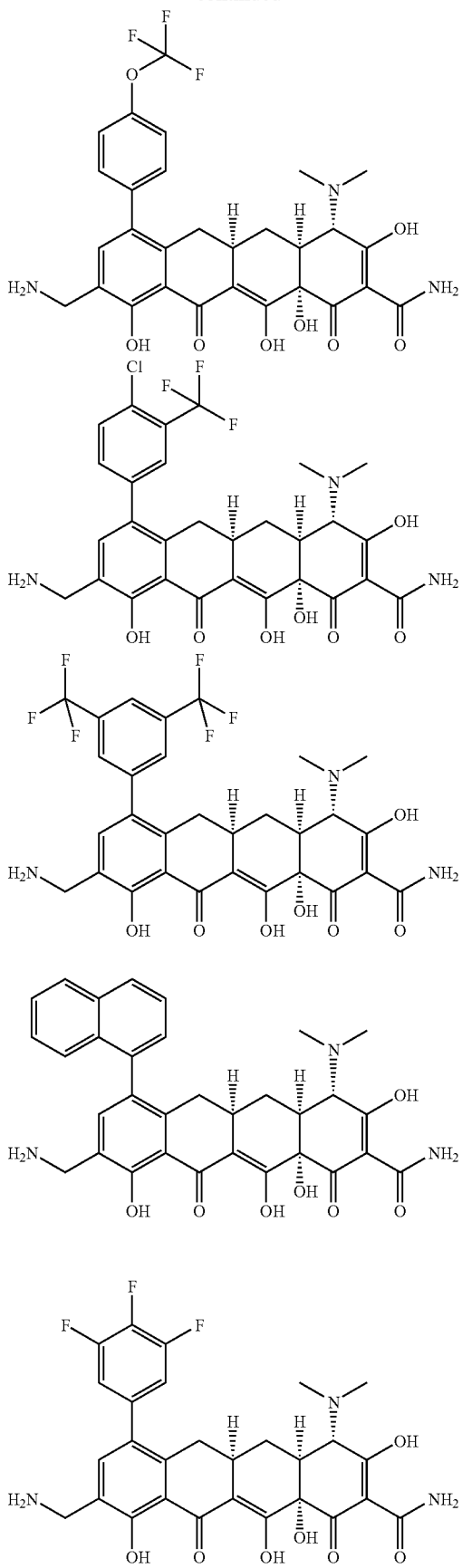

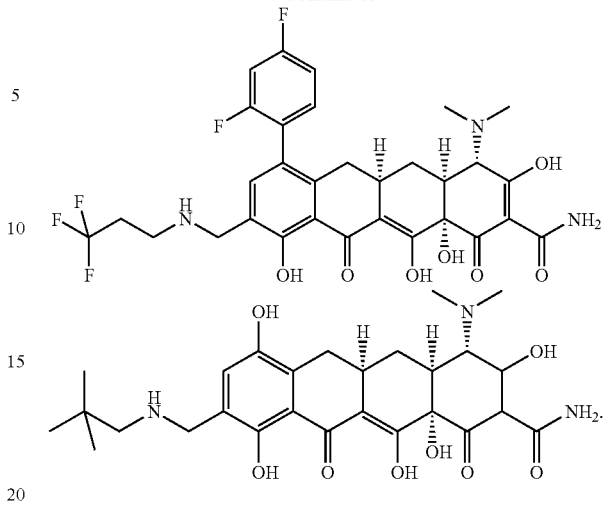

In another embodiment, the invention includes tetracycline compounds of the Formula (X):

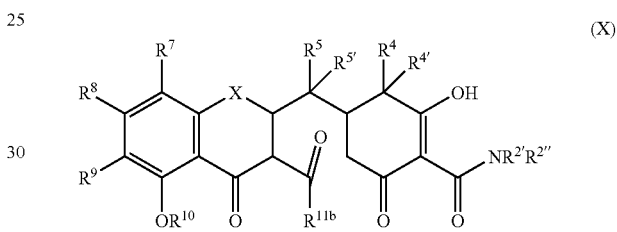

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen, optionally linked to $R^2$ to form a ring;

$R^2$ is hydrogen, alkyl, halogen, alkenyl, alkynyl, aryl, hydroxyl, thiol, cyano, nitro, acyl, formyl, alkoxy, amino, alkylamino, heterocyclic, or absent, optionally linked to $R^1$ to form a ring;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$ is hydrogen, alkyl, aryl, benzyl, arylalkyl, or a pro-drug moiety;

$R^{11b}$ is hydroxyl, alkoxy, aryloxy, or alkylamino;

$R^4$ and $R^{4'}$ are each independently $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7n})_{0-1}C(=W')WR^{7l}$;

R[8] is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}(NR^{8c})_{0-1}C(=E')ER^{8a}$;

R[9] is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}(NR^{9f})_{0-1}C(=Z')ZR^{9a}$;

$R^{7l}$, $R^{7m}$, $R^{7n}$, $R^{7o}$, $R^{7p}$, $R^{7q}$, $R^{8a}$, $R^{8b}$, $R^{8c}$, $R^{8d}$, $R^{8e}$, $R^{8f}$, $R^{9a}$, $R^{9b}$, $R^{8c}$, $R^{8e}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

Q is a double bond when $R^2$ is absent, Q is a single bond when $R^2$ is hydrogen, alkyl, halogen, hydroxyl, thiol, alkenyl, alkynyl, aryl, acyl, formyl, alkoxy, amino, alkylamino, cyano, nitro, or heterocyclic;

W is $CR^{7o}R^{7p}$, S, $NR^{7m}$ or O;

W' is O, $NR^{7q}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In a further embodiment, the tetracycline compound of Formula (X) is:

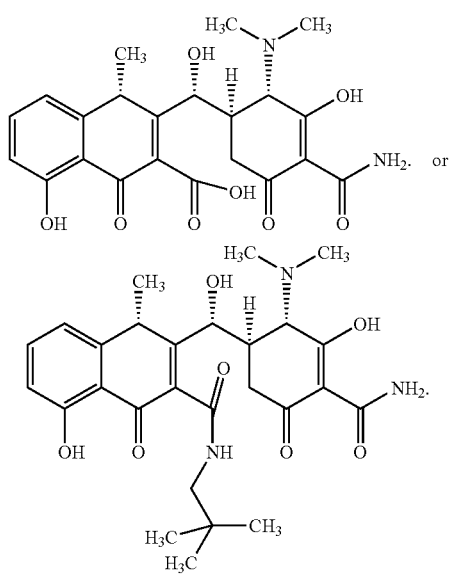

In another embodiment, the invention includes tetracycline compounds of the Formula (XI):

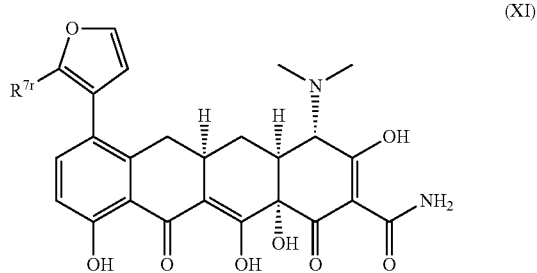

(XI)

wherein $R^{7r}$ is substituted or unsubstituted N-piperidinylalkyl, dialkylaminoalkyl and pharmaceutically acceptable salts, esters and enantiomers thereof.

In one embodiment, dialkylaminoalkyl is dimethylaminomethyl. In another embodiment, the substituted N-piperidinylalkyl is methyl substituted N-piperidinylmethyl.

Examples of the tetracycline compounds of Formula (XI) are:

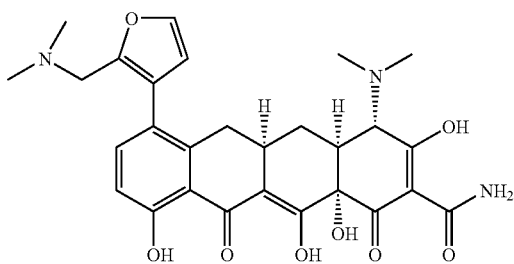

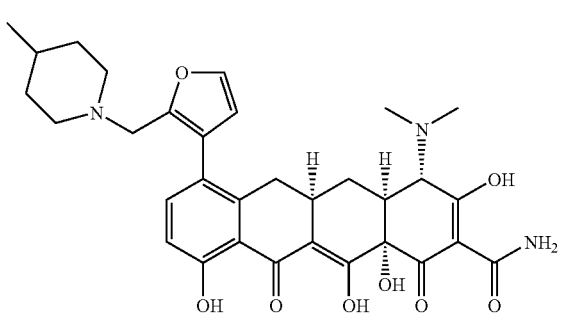

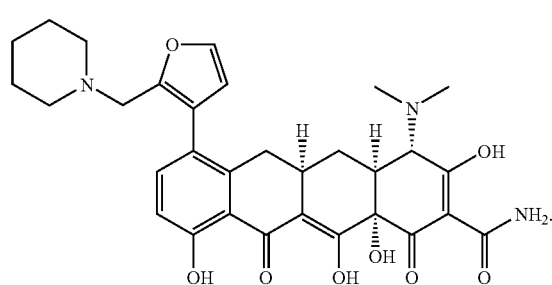

In another embodiment, the invention includes tetracycline compounds of the Formula (XII):

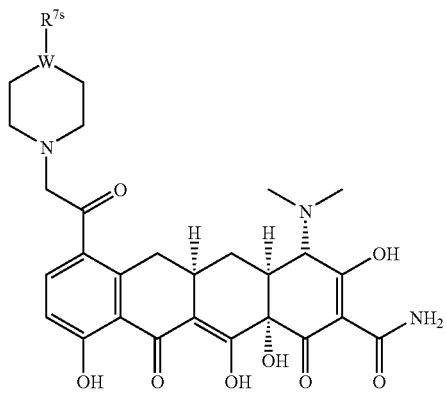
(XII)

wherein
W is N or CH; and
$R^{7s}$ is substituted or unsubstituted alkyl, aryl, alkoxycarbonyl, alkylcarbonyl, cycloalkyl, or aminocarbonyl; and pharmaceutically acceptable salts, esters and enantiomers thereof.

In one embodiment, W is CH. In a further embodiment, $R^{7s}$ is unsubstituted alkyl such as, for example, methyl.

In another embodiment, W is N. In a further embodiment, is alkoxycarbonyl (e.g., ethoxycarbonyl), alkylcarbonyl (e.g., acyl), cycloalkyl (e.g., cyclohexyl), aryl (e.g., phenyl), alkyl (e.g., isopropyl), or aminocarbonyl.

Examples of the tetracycline compounds of Formula (XII) are:

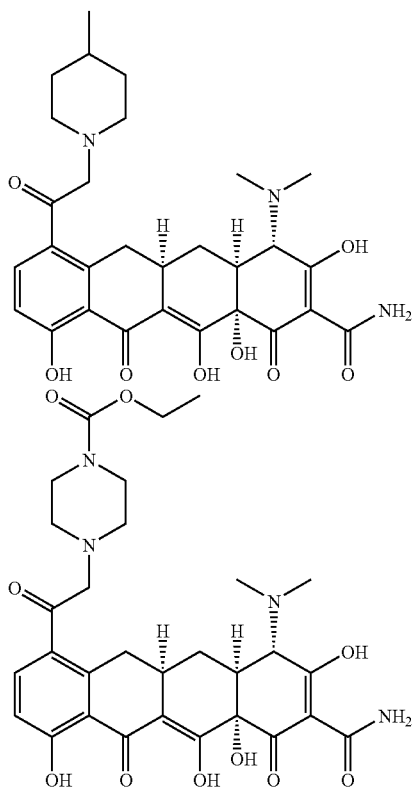

-continued

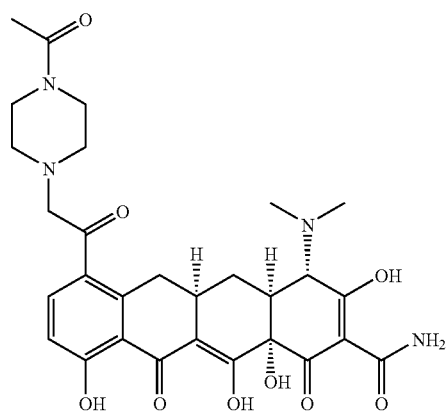

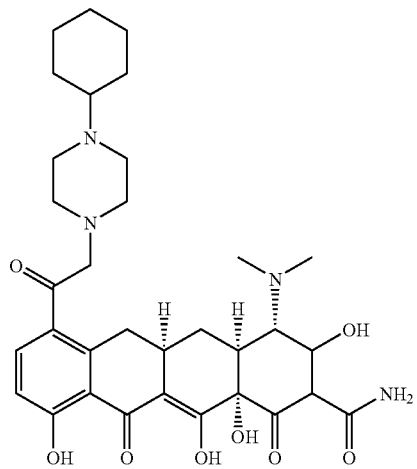

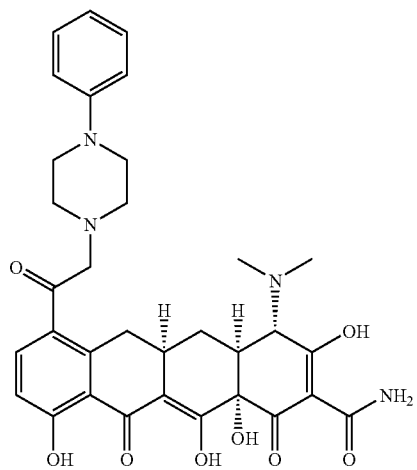

-continued

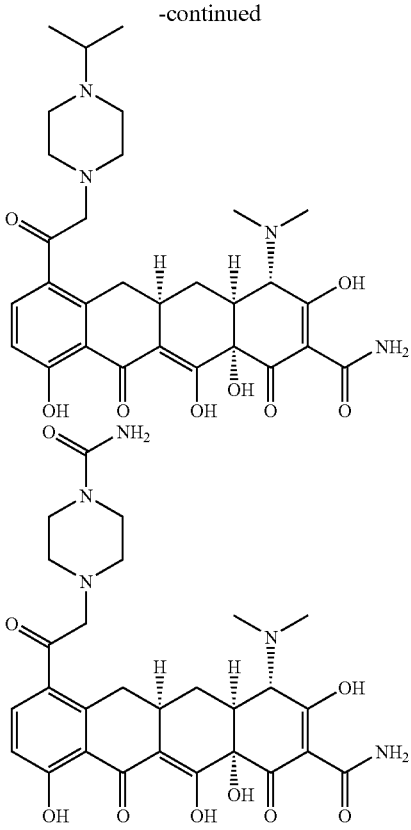

In another embodiment, the invention includes tetracycline compounds of the Formula XIII:

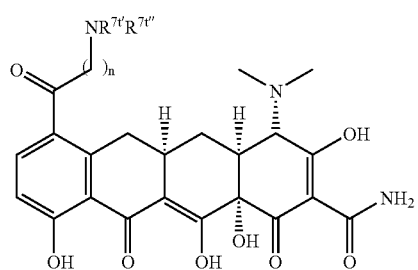

(XIII)

wherein n is 0, 1 or 2;

$R^{7t'}$ is hydrogen, alkyl, alkenyl or cycloalkyl;

$R^{7t''}$ is unsubstituted alkyl, dialkylaminoalkyl, halogenated alkyl, alkoxyalkyl, substituted or unsubstituted arylalkyl, cycloalkyl, alkenylalkyl, heterocyclic, cyano substituted alkyl, alkoxy substituted alkyl, heteroarylalkyl, aminocarbonylalkyl, aryl, hydrogen, alkylcarbonyl, aminoalkyl or alkoxycarbonyl; and pharmaceutically acceptable salts, esters and enantiomers thereof.

In one embodiment, n is 0. In a further embodiment, $R^{7t'}$ is hydrogen. In yet another embodiment, $R^{7t''}$ is dialkylaminoalkyl.

In another embodiment, n is 1. In a further embodiment, $R^{7t''}$ is alkoxyalkyl, such as, for example, methoxyethyl. In another embodiment, $R^{7t''}$ is alkyl such as, for example, isopropyl. In yet a further embodiment $R^{7t'}$ is alkyl such as, for example, methyl.

In another embodiment, $R^{7t'}$ is alkenyl. In a further embodiment, $R^{7t''}$ is alkoxycarbonyl such as, for example, methoxycarbonyl In another embodiment, $R^{7t''}$ is alkylcarbonyl such as, for example, acyl. In a further embodiment, $R^{7t'}$ is cycloalkyl, such as cyclpropyl.

In another embodiment, n is 1. In a further embodiment, $R^{7t'}$ is hydrogen. In another embodiment, $R^{7t''}$ is halogenated alkyl (e.g., fluoroethyl, difluoroethyl or trifluoroethyl), unsubstituted alkyl (e.g., methyl, ethyl, t-butylmethyl, t-butyl or diethylmethyl), cycloalkyl (e.g., cyclohexyl, cyclopropyl, morpholino, cyclobutyl, bicyclo[2.2.1]heptenyl, cyclopentyl), arylalkyl (e.g., phenylmethyl), alkenylalkyl, cyano substituted alkyl, heteroarylalkyl (e.g., pyridinylmethyl, furanylmethyl or N-methylpyrrolylmethyl), aminocarbonylalkyl (e.g., aminocarbonylmethyl), alkoxy substituted alkyl (e.g., methoxy substituted alkyl), aryl (e.g., pyridinyl or phenyl), aminoalkyl (e.g., aminomethyl) or substituted arylalkyl (e.g., difluorophenyl).

In yet another embodiment, n is 2. In a further embodiment, $R^{7t'}$ is hydrogen. In yet a further embodiment, $R^{7t''}$ is alkyl, such as for example, methyl. In another embodiment, $R^{7t''}$ is alkylcarbonyl, such as, for example, acyl.

Examples of the tetracycline compounds of Formula (XIII) are:

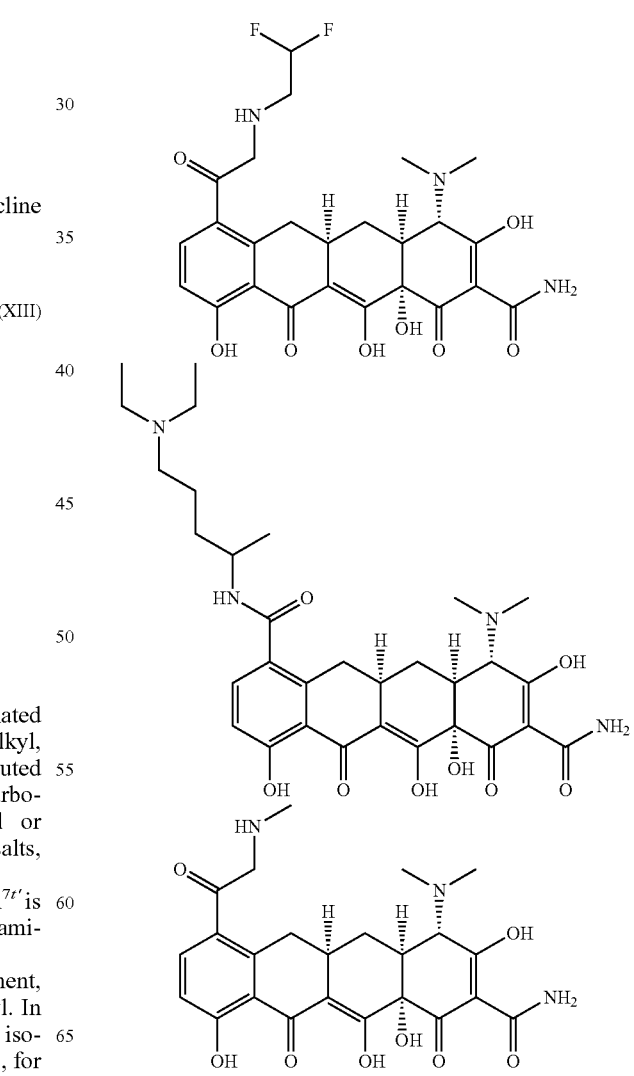

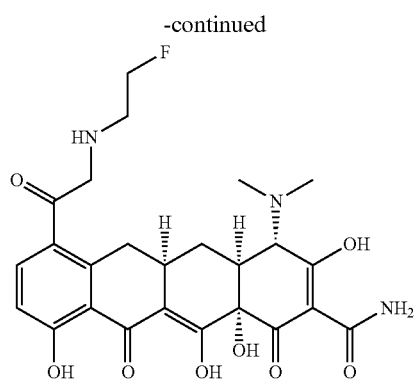
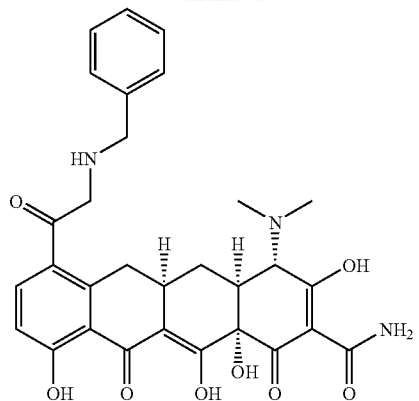
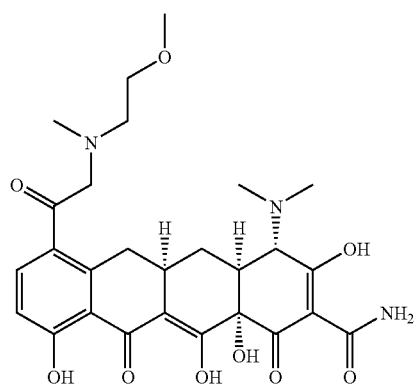
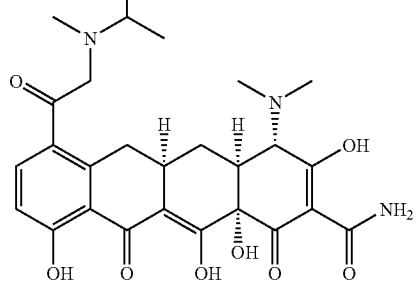
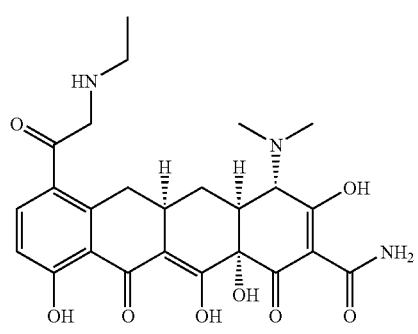
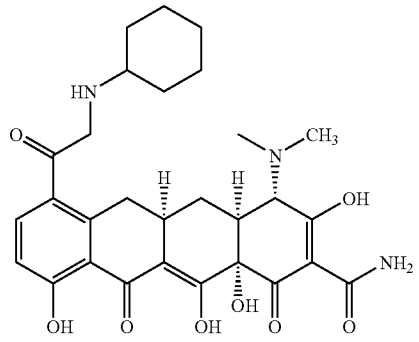
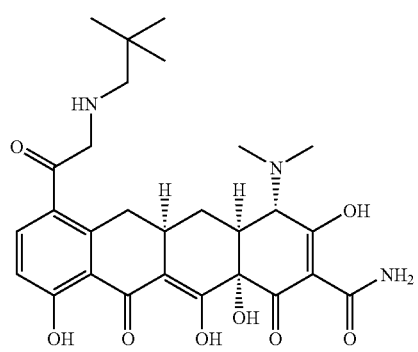
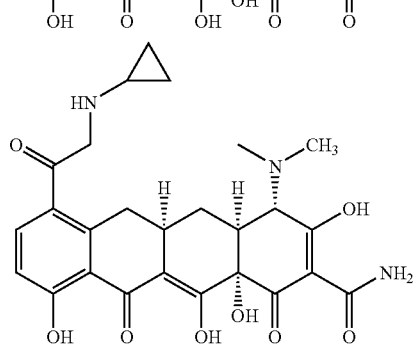

65
-continued
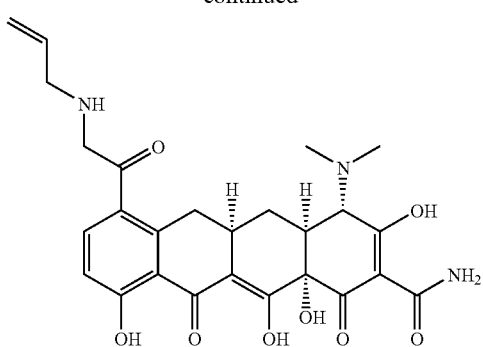
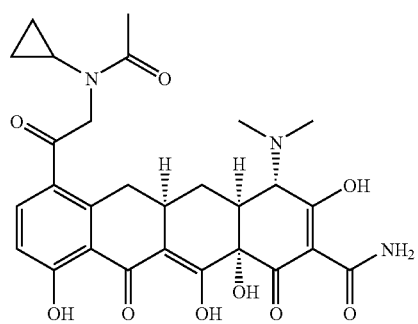
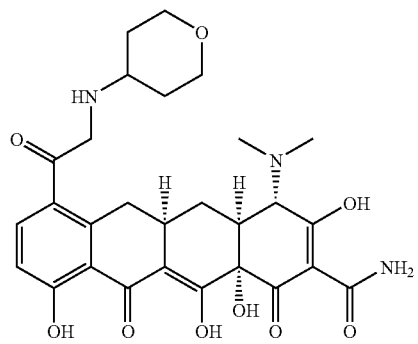
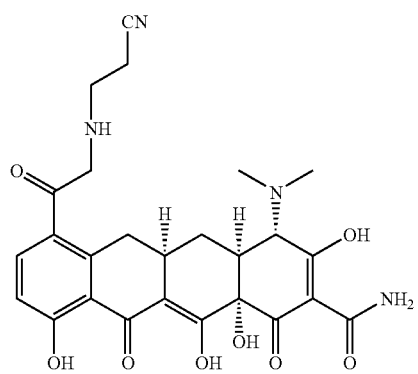
66
-continued
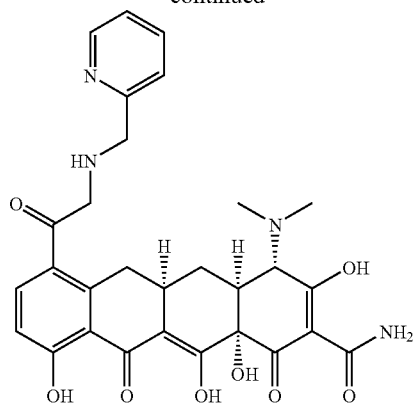
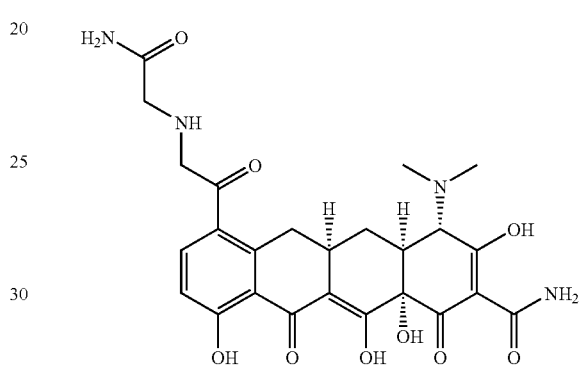
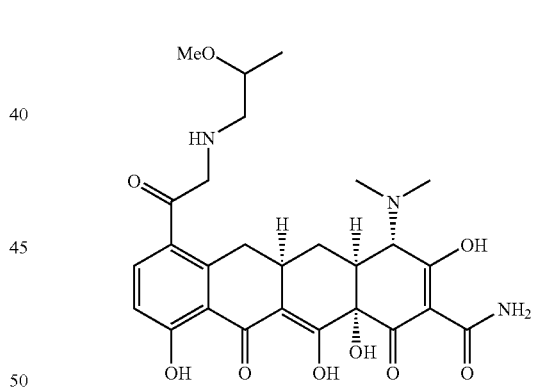
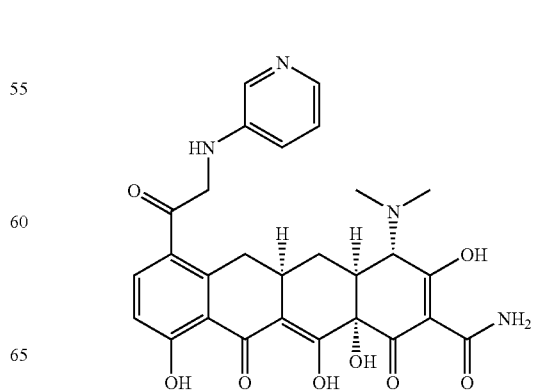

67
-continued
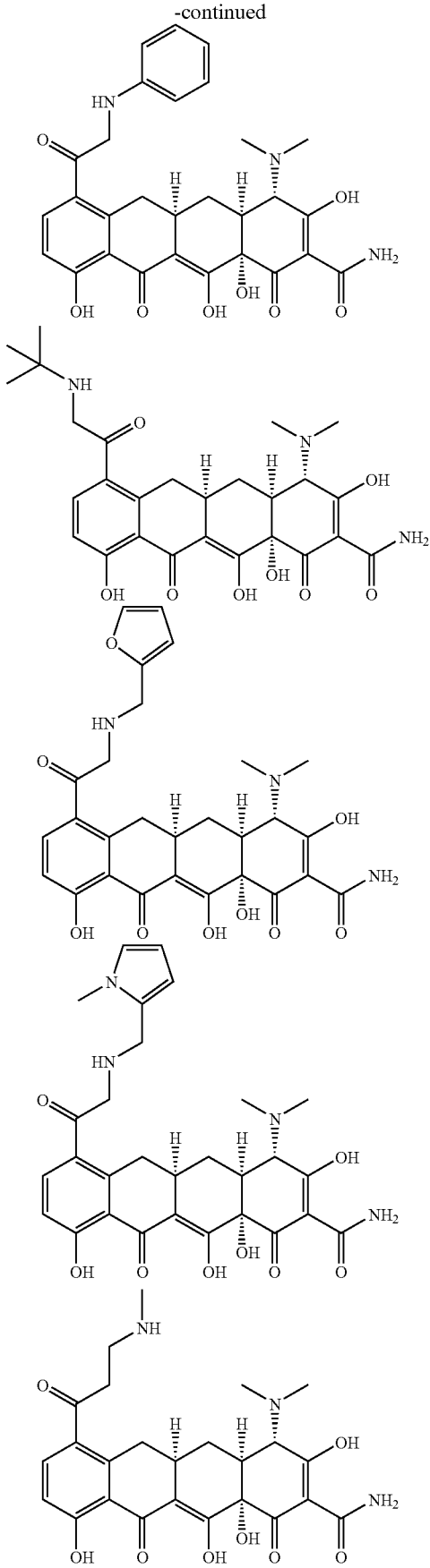
68
-continued
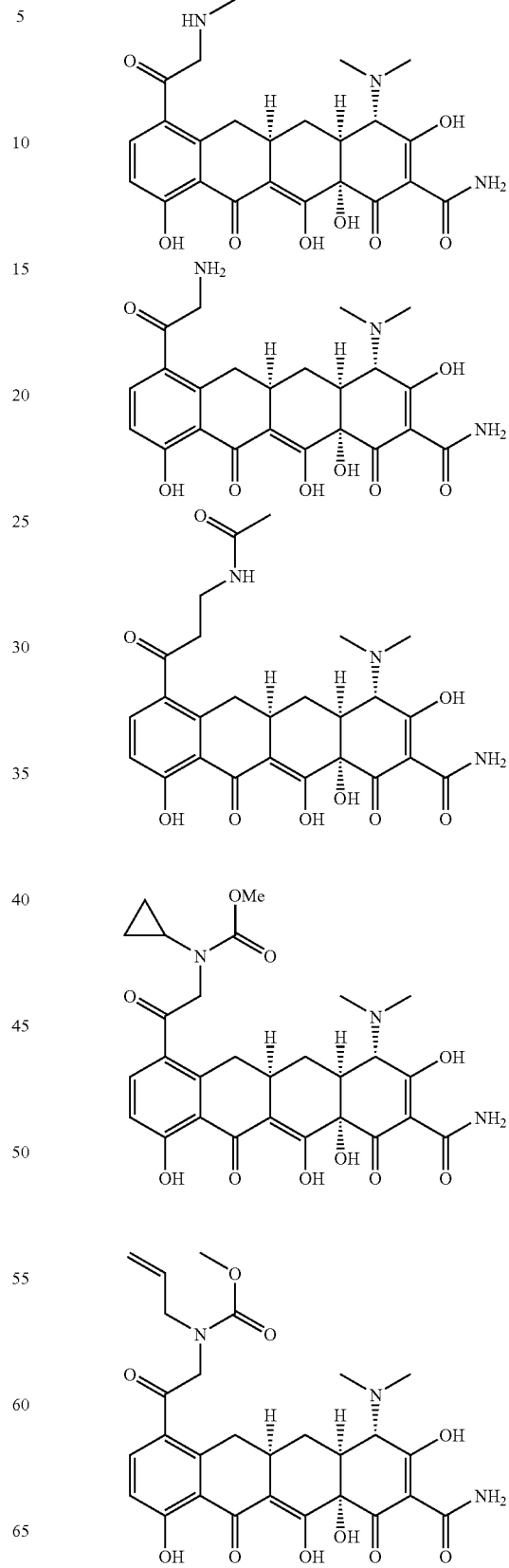

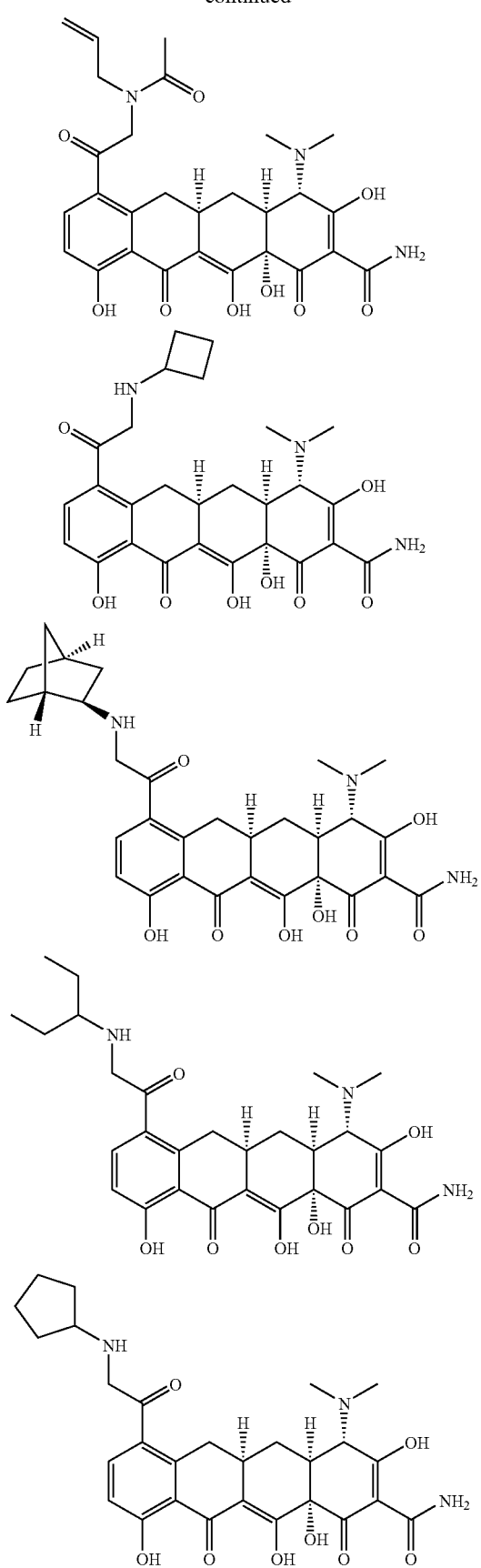

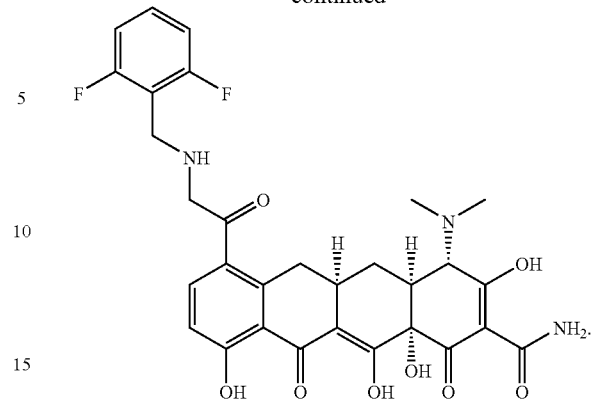

In another embodiment, the invention includes tetracycline compounds of Formula XIV:

(XIV)

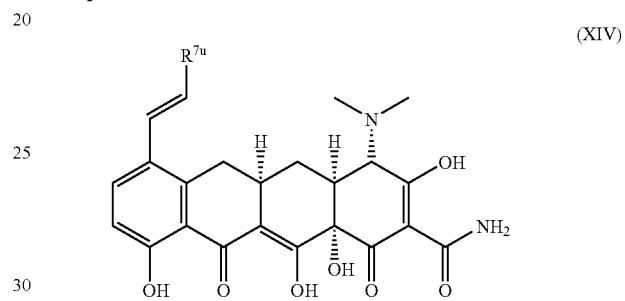

wherein $R^{7u}$ is substituted or unsubstituted N-piperidinylalkyl, dialkylaminoalkyl, alkoxyaminoalkyl, alkylaminoalkyl or dipiperidinium methyl; and pharmaceutically acceptable salts, esters and enantiomers thereof.

In one embodiment, $R^{7u}$ is substituted N-piperidinylalkyl, such as, for example, methyl substituted N-piperidinylalkyl or halogen substituted N-piperidinylalkyl.

In another embodiment, the halogen substituted N-piperidinylalkyl is, includes, for example, fluorine substituted N-piperidinylalkyl.

In yet another embodiment, $R^{7u}$ is dialkylaminoalkyl, including, for example, dimethylaminomethyl.

In another embodiment, $R^{7u}$ is alkylaminomethyl is methylaminomethyl.

In yet another embodiment, $R^{7u}$ is alkoxyaminoalkyl is methoxyaminoalkyl.

Examples of the tetracycline compounds of Formula (XIV) are:

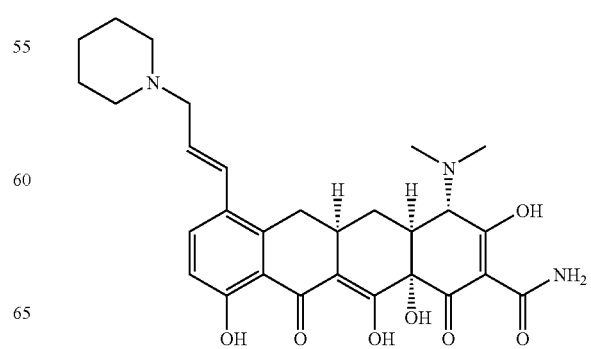

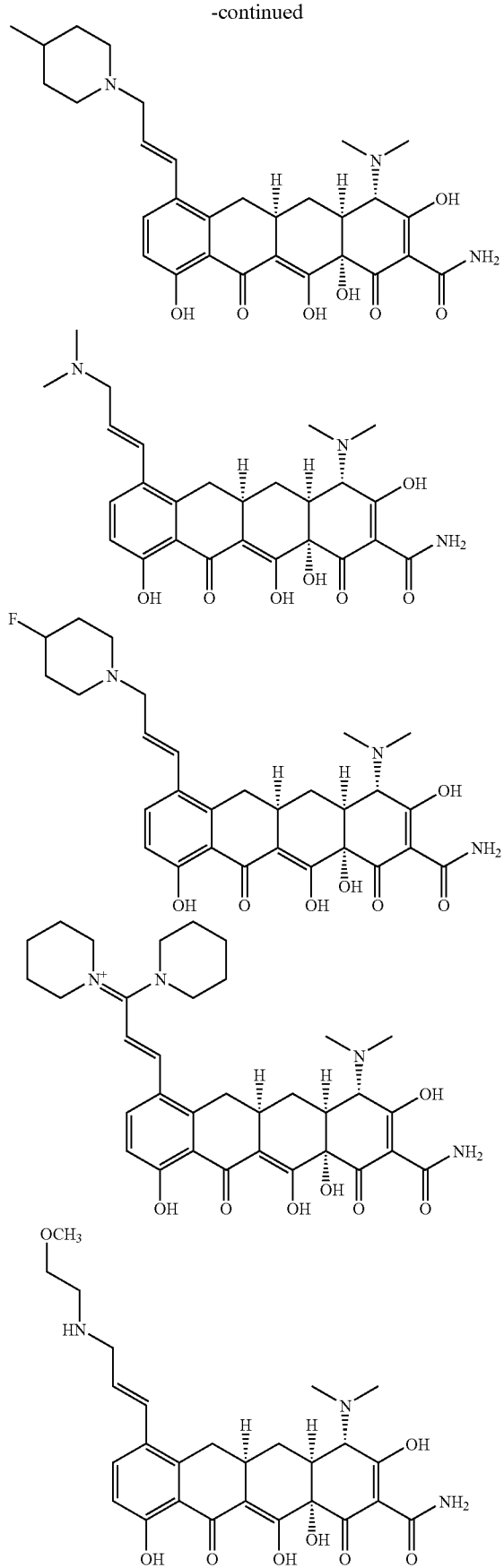

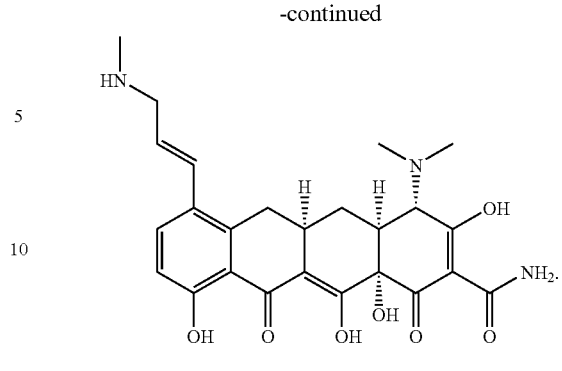

In another embodiment, the invention pertains, at least in part, to tetracycline compounds of formula (XV):

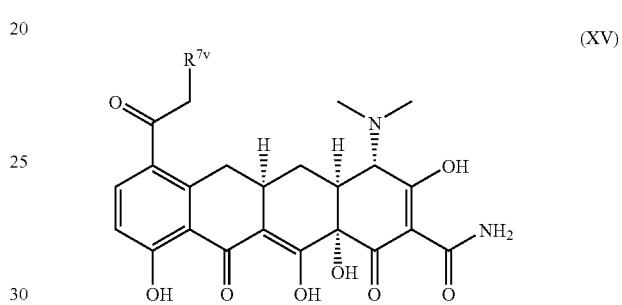

(XV)

wherein $R^{7v}$ is heteroaryl; and pharmaceutically acceptable salts, esters and enantiomers thereof.

In one embodiment, the said heteroryl is imidizolyl, methyl imidizolyl, imidizolidinyl or methyl imidizolidinyl.

Examples of tetracycline compounds of formula (XV) are:

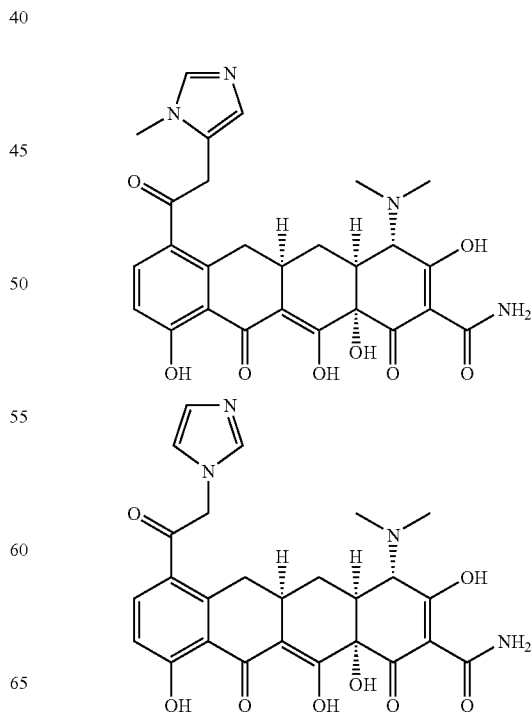

-continued

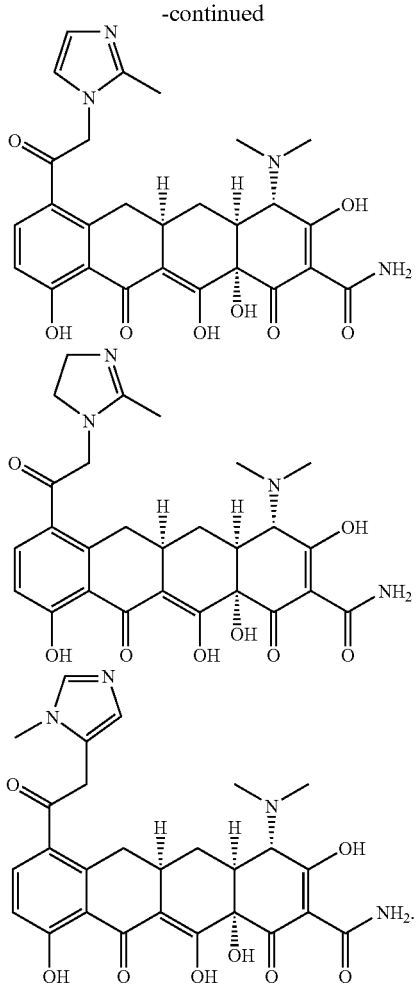

In another embodiment, the invention pertains, at least in part, to tetracycline compounds of formula (XVI):

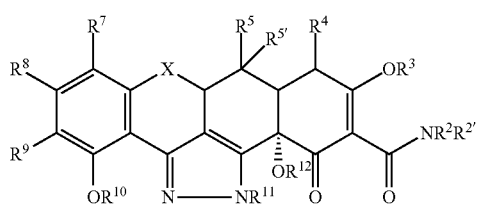

wherein:

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each independently hydrogen, alkyl, aryl, benzyl, arylalkyl, or a pro-drug moiety;

$R^{3'}$ is hydroxyl, hydrogen, or a pro-drug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7c})_{0-1}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{9c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In a further embodiment, $R^{2'}$, $R^3$, $R^{10}$, $R^{11}$, and $R^{12}$ are each hydrogen or a prodrug moiety; X is $CR^6R^{6'}$; and $R^{2''}$, $R^5$, $R^{5'}$, $R^6$, and $R^{6'}$ are each hydrogen.

Alternatively, $R^5$ and $R^{5'}$ are hydrogen and X is $CR^6R^{6'}$, wherein $R^6$ is methyl and $R^{6'}$ is hydroxy. Alternatively, when $R^5$ is hydroxyl; X is $CR^6R^{6'}$; $R^6$ is methyl; and $R^{5'}$ and $R^{6'}$ are hydrogen. In yet another embodiment, X is $CR^6R^{6'}$; $R^5$, $R^{5'}$, $R^6$ and $R^{6'}$ are hydrogen atoms and $R^7$ is dimethylamino.

In one embodiment, $R^9$ is hydrogen. In another embodiment, $R^9$ is substituted or unsubstituted aryl (e.g., phenyl or heteroaryl). In another embodiment, $R^9$ is substituted or unsubstituted alkyl. In a further embodiment, $R^9$ is aminoalkyl, e.g., aminomethyl (e.g., $-CH_2-N^{9n}R^{9m}$, wherein $R^{9n}$ is hydrogen or a prodrug and $R^{9m}$ is hydrogen or lower alkyl).

In another embodiment, $R^7$ is hydrogen. In yet another embodiment, $R^7$ is substituted or unsubstituted aryl, e.g., phenyl or heteroaryl (e.g., pyridinyl, pyrrolyl, pyrazinyl, etc.). In another embodiment, $R^7$ is substituted or unsubstituted amino (e.g., dimethylamino), nitro or halogen. In another embodiment, $R^8$ is hydrogen. In another further embodiment, $R^{11}$ is hydrogen.

In a further embodiment, the tetracycline compound is:

In another embodiment, the invention pertains to tetracycline compounds substituted at the 2 position such as compounds of formula (XVII):

(XVII)

wherein:

$R^{2a}$ is alkyl or aryl;

$R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each independently hydrogen, alkyl, aryl, benzyl, arylalkyl, or a pro-drug moiety;

$R^{3'}$ is hydroxyl, hydrogen, or a pro-drug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $—(CH_2)_{0-3}(NR^{7c})_{0-1}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $—(CH_2)_{0-3}(NR^{7c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $—(CH_2)_{0-3}(NR^{7c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, for S;

X is $CHC(R^{13}Y'Y)$, $C=CR^{13}Y$, $CR^6R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In a further embodiment, $R^3$, $R^{10}$, $R^{11}$, and $R^{12}$ are each hydrogen or a prodrug moiety; X is $CR^6R^{6'}$; and $R^5$, $R^{5'}$, $R^6$, and $R^{6'}$ are each hydrogen.

Alternatively, $R^5$ and $R^{5'}$ are hydrogen and X is $CR^6R^{6'}$, wherein $R^6$ is methyl and $R^{6'}$ is hydroxy. Alternatively, when $R^5$ is hydroxyl; X is $CR^6R^{6'}$; $R^6$ is methyl; and $R^{5'}$ and $R^{6'}$ are hydrogen. In yet another embodiment, X is $CR^6R^{6'}$; $R^5$, $R^{5'}$, $R^6$ and $R^{6'}$ are hydrogen atoms and $R^7$ is dimethylamino.

In one embodiment, $R^9$ is hydrogen. In another embodiment, $R^9$ is substituted or unsubstituted aryl (e.g., phenyl or heteroaryl). In another embodiment, $R^9$ is substituted or unsubstituted alkyl. In a further embodiment, $R^9$ is aminoalkyl, e.g., aminomethyl (e.g., $—CH_2—N^{9n}R^{9m}$, wherein $R^{9n}$ is hydrogen or a prodrug and $R^{9m}$ is hydrogen or lower alkyl).

In another embodiment, $R^7$ is hydrogen. In yet another embodiment, $R^7$ is substituted or unsubstituted aryl, e.g., phenyl or heteroaryl (e.g., pyridinyl, pyrrolyl, pyrazinyl, etc.). In another embodiment, $R^7$ is substituted or unsubstituted amino (e.g., dimethylamino), nitro or halogen. In another embodiment, $R^8$ is hydrogen.

In a further embodiment, $R^{2a}$ is alkyl, e.g., methyl, ethyl or propyl.

In another further embodiment, the tetracycline compound is:

77

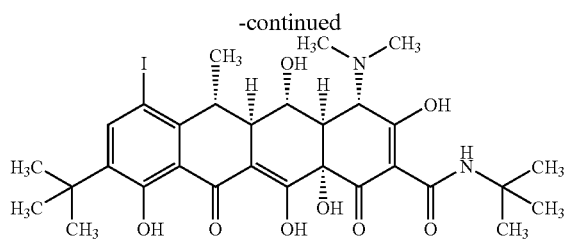

In one embodiment, the tetracycline compounds of the invention do not include those described in U.S. Ser. NoS. 09/660,598, 09/823,884, 09/852,908, 10/819,343, 10/820,456, 09/894,805, 09/895,796, 09/895,812, 09/895,797, 09/895,857, 10/097,634, 10/759,484, 10/337,914, 10/636,437, 10/752,378, or 10/740,961. The entire contents of each of these applications are hereby incorporated herein in their entirety.

Methods for Synthesizing Tetracycline Compounds of the Invention

The tetracycline compounds of this invention can be synthesized using the methods described in the Schemes and/or by other techniques known to those of ordinary skill in the art.

78

The substituted tetracycline compounds of the invention can be synthesized using the methods described in the following schemes and by using art recognized techniques. All novel substituted tetracycline compounds described herein are included in the invention as compounds.

9- and 7-substituted tetracyclines can be synthesized by the method shown in Scheme 1. As shown in Scheme 1, 9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate reactive reagent to yield the desired compound (e.g., in Scheme 1, 7-cyclopent-1-enyl doxycycline (1H) and 9-cyclopent-1-enyl doxycycline (1I)).

SCHEME 1

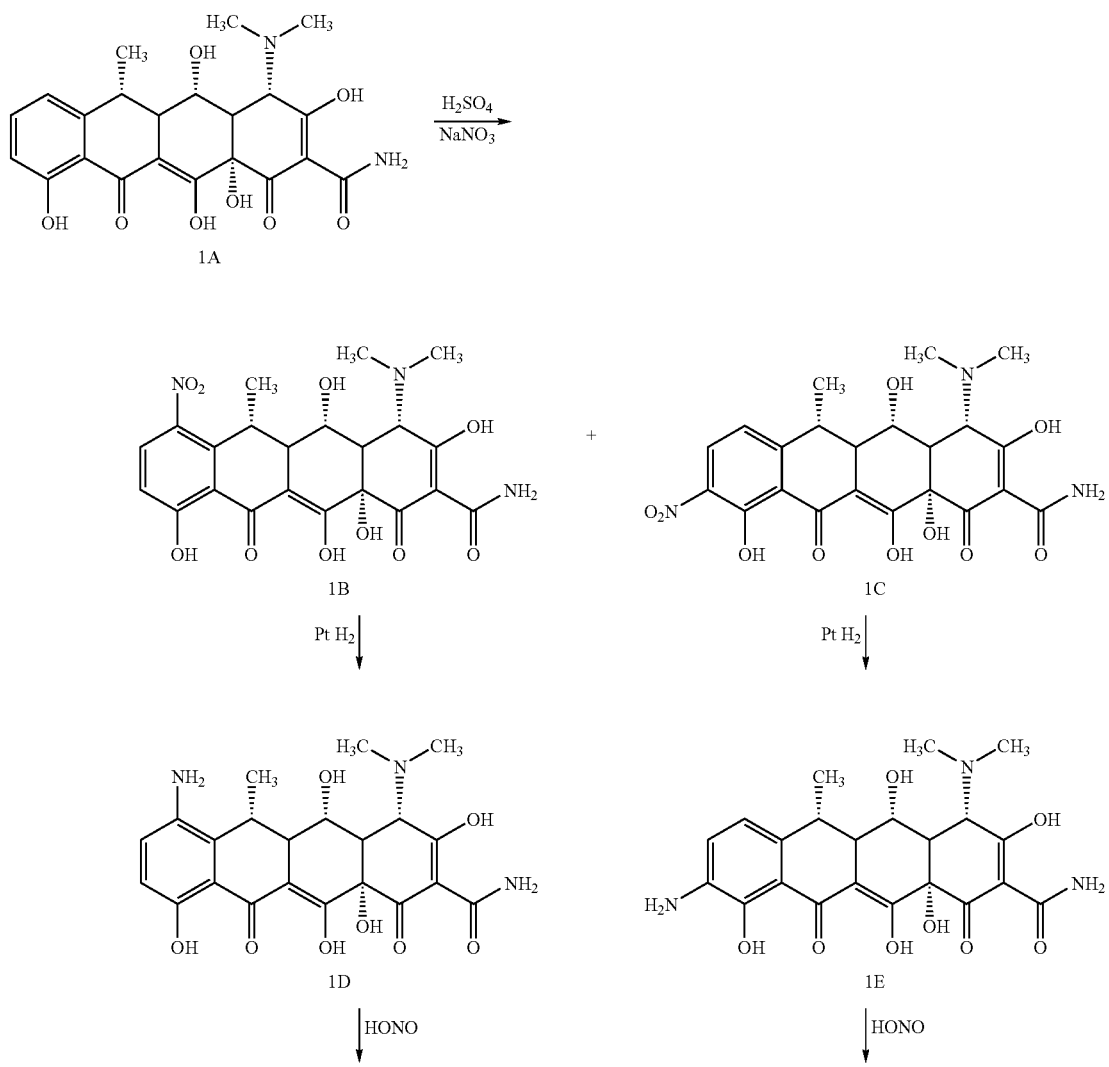

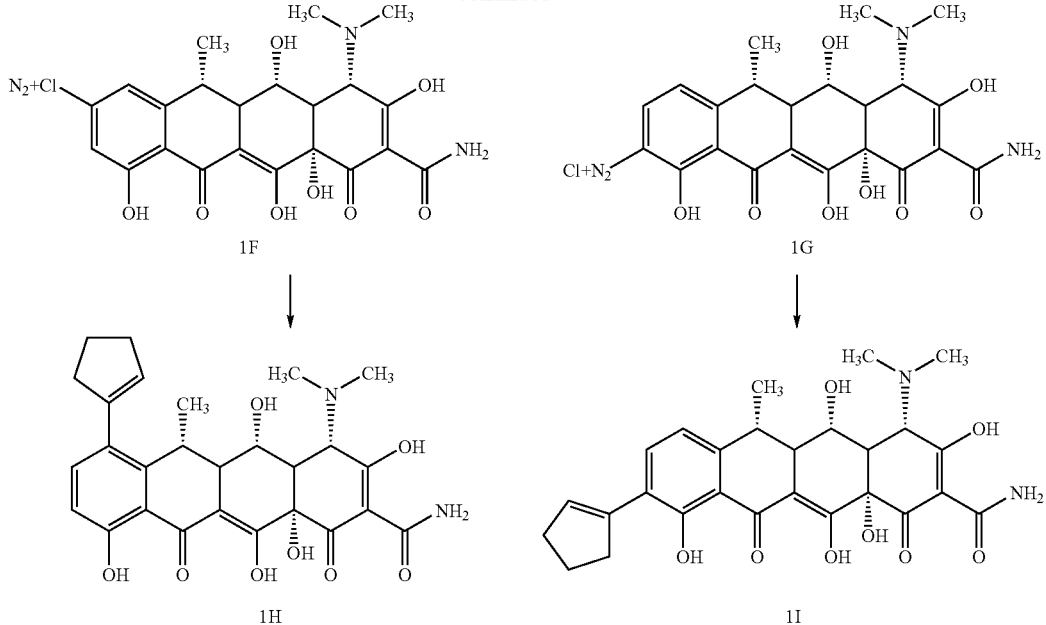

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

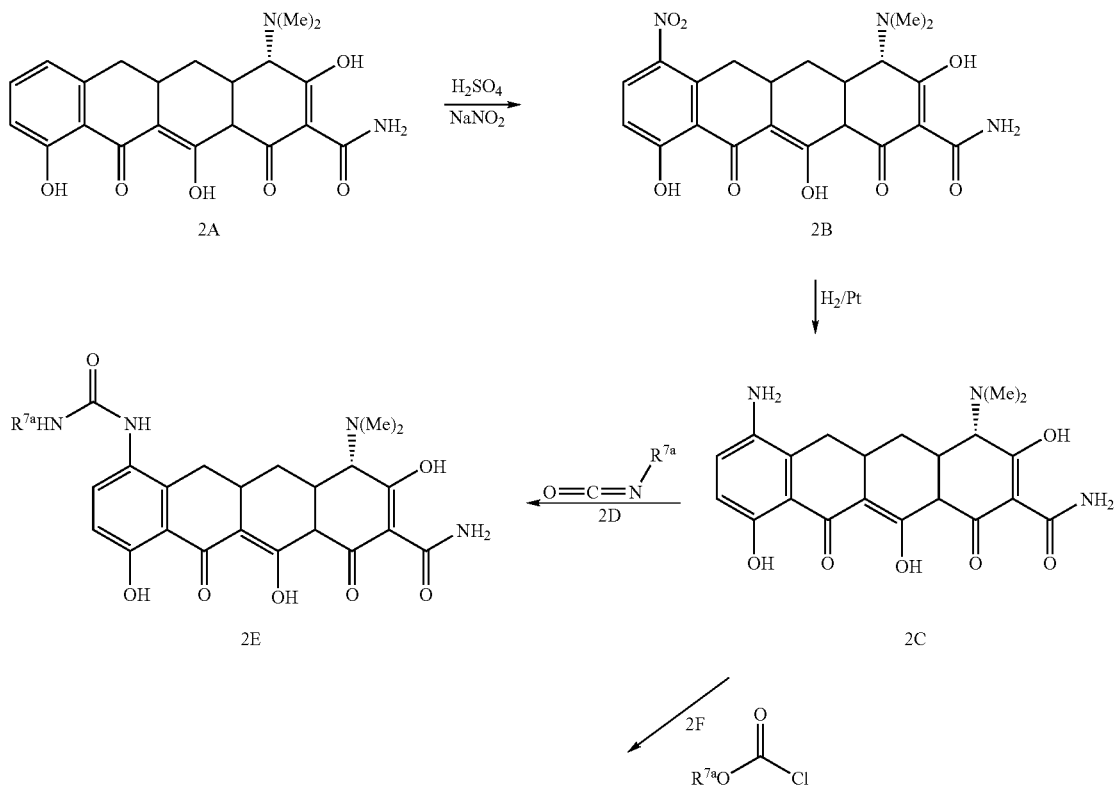

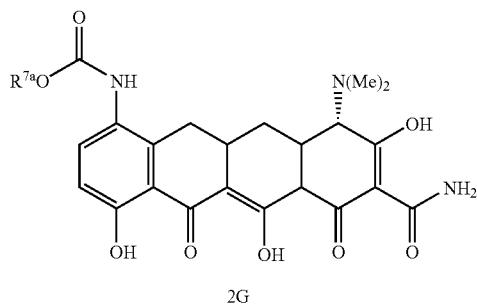

2G

As shown in Scheme 3, tetracycline compounds of the invention, wherein $R^7$ is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

7-alkenyl tetracycline compounds, such as 7-alkynyl sancycline (4A) and 7-alkenyl sancycline (4B), can be hydrogenated to form 7-alkyl substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

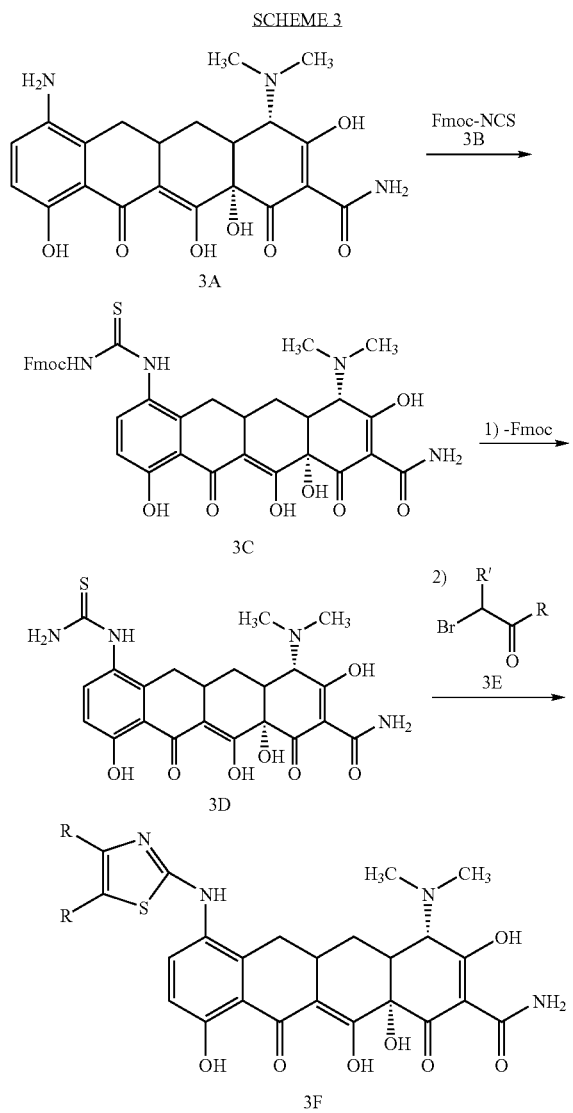

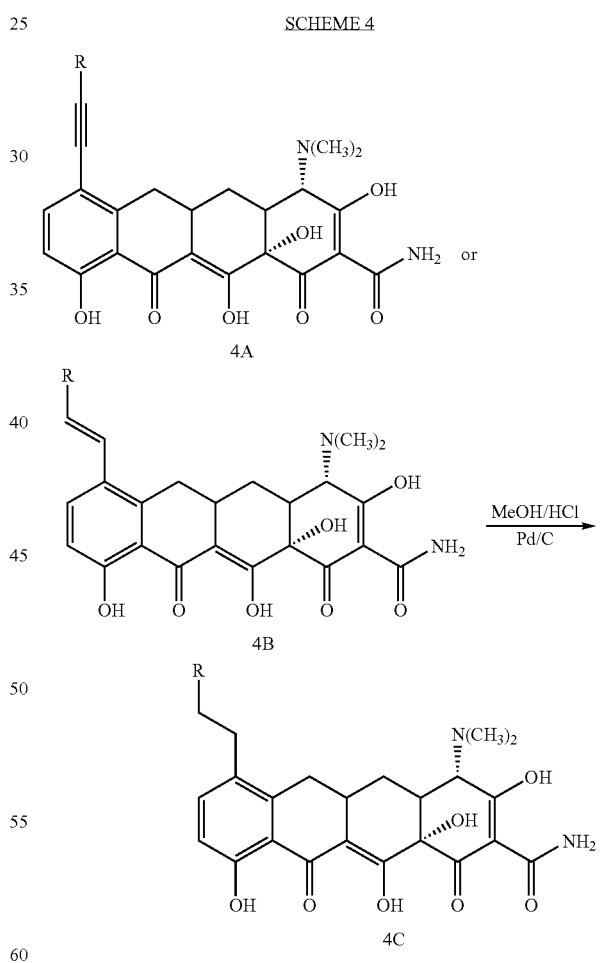

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions.

The reaction is quenched, and the resulting 7-iodo sancycline (5B) can then be purified using standard techniques known in the art. To form the aryl derivative, 7-iodo sancycline (5B) is treated with an aqueous base (e.g., $Na_2CO_3$) and an appropriate boronic acid (5C) and under an inert atmosphere. The reaction is catalyzed with a palladium catalyst (e.g., $Pd(OAc)_2$). The product (5D) can be purified by methods known in the art (such as HPLC). Other 7-aryl, alkenyl, and alkynyl tetracycline compounds can be synthesized using similar protocols

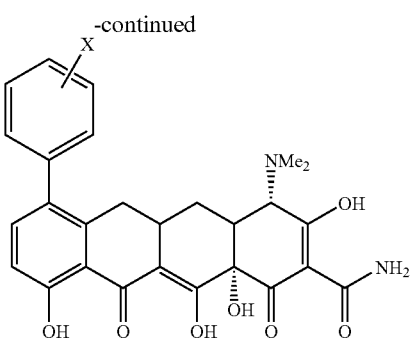

5D

The 7-substituted tetracycline compounds of the invention can also be synthesized using Stille cross couplings. Stille cross couplings can be performed using an appropriate tin reagent (e.g., R—$SnBu_3$) and a halogenated tetracycline compound, (e.g., 7-iodosancycline). The tin reagent and the iodosancycline compound can be treated with a palladium catalyst (e.g., $Pd(PPh_3)_2Cl_2$ or $Pd(AsPh_3)_2Cl_2$) and, optionally, with an additional copper salt, e.g., CuI. The resulting compound can then be purified using techniques known in the art.

The compounds of the invention can also be synthesized using Heck-type cross coupling reactions. As shown in Scheme 6, Heck-type cross-couplings can be performed by suspending a halogenated tetracycline compound (e.g., 7-iodosancycline, 6A) and an appropriate palladium or other transition metal catalyst (e.g., $Pd(OAc)_2$ and CuI) in an appropriate solvent (e.g., degassed acetonitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E) tetracycline compound can then be purified using techniques known in the art.

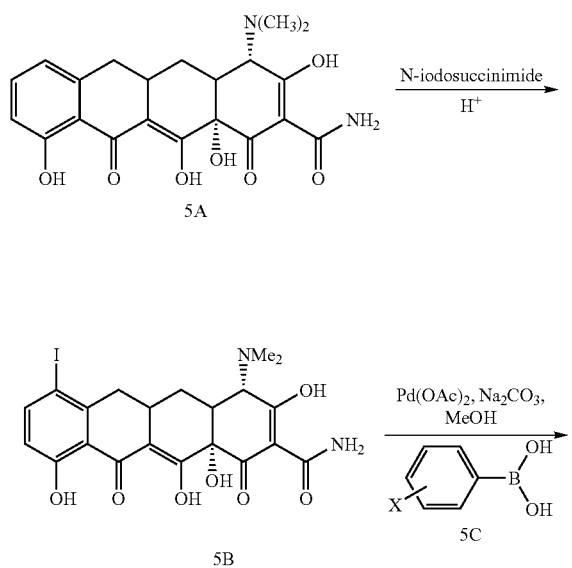

SCHEME 6

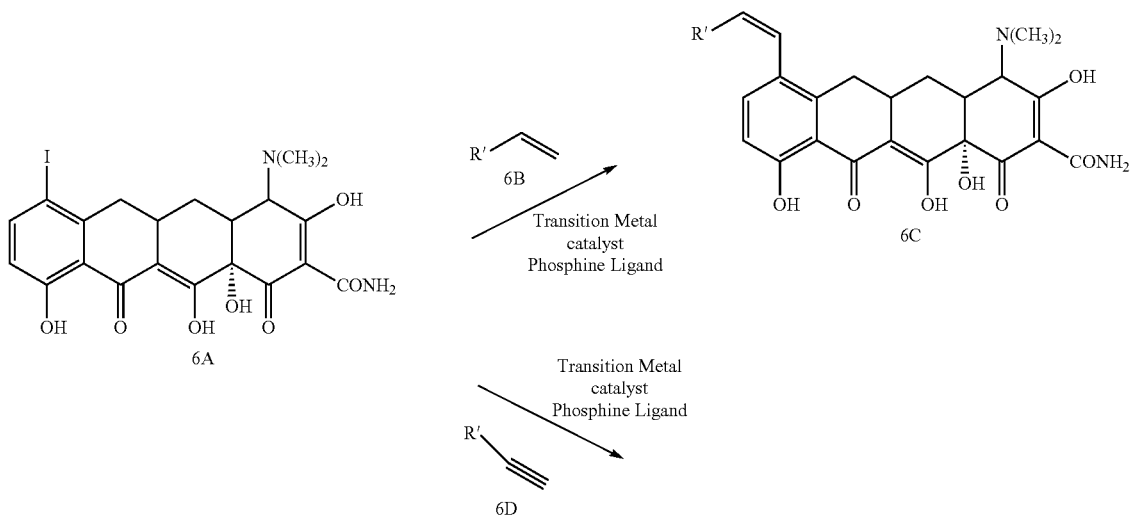

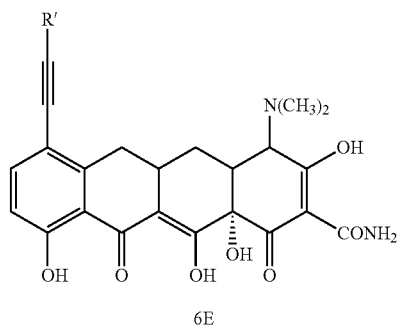

6E

To prepare 7-(2'-Chloro-alkenyl)-tetracycline compounds, the appropriate 7-(alkynyl)-sancycline (7A) is dissolved in saturated methanol and hydrochloric acid and stirred. The solvent is then removed to yield the product (7B).

tuted compounds (8A) in strong acid (e.g. HF, methanesulphonic acid, and trifluoromethanesulfonic acid) and adding the appropriate carboxylic acid to yield the corresponding esters (8B).

SCHEME 7

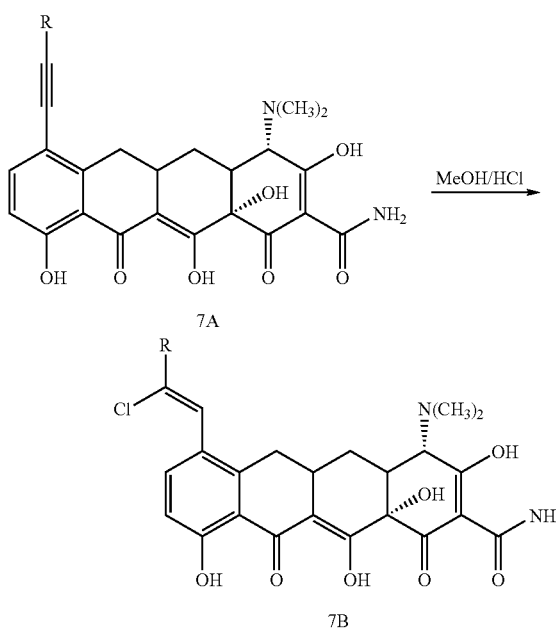

SCHEME 8

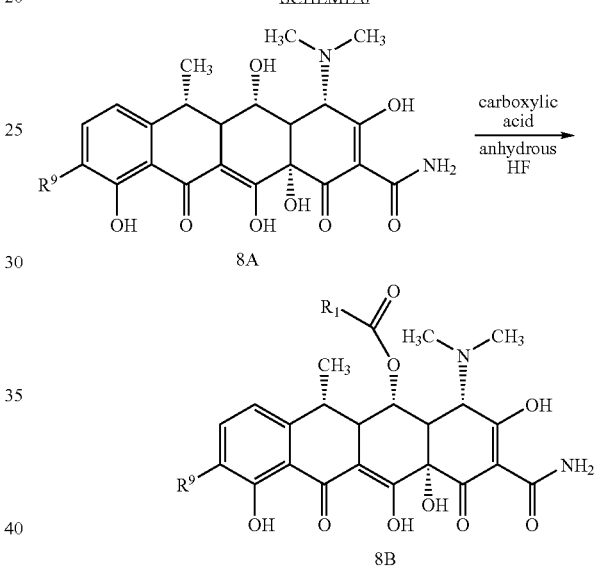

As depicted in Scheme 8, 5-esters of 9-substituted tetracycline compounds can be formed by dissolving the 9-substi- As shown in Scheme 9 below, 7 and 9-aminomethyl tetracyclines may be synthesized using reagents such as hydroxymethyl-carbamic acid benzyl ester.

SCHEME 9

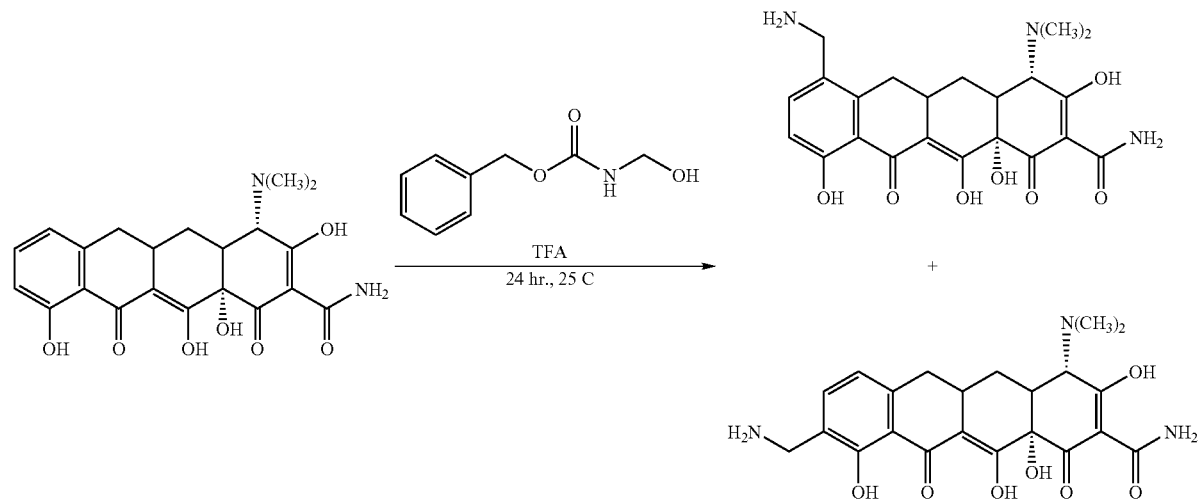

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO-$) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alklthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Methods for Treating Tetracycline Responsive States

The invention also pertains to methods for treating a tetracycline responsive states in subjects, by administering to a subject an effective amount of a tetracycline compound of the invention (e.g., a compound of Formula I, II, III, IV, V, VI, VII, VIII, IX, X, XI, XII, XIII, XIV, XV, XVI or XVII or otherwise described herein), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention. Tetracycline compound responsive states include bacterial, viral, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.,* 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml (as measured by assays known in the art and/or the assay given in Example 2).

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by abberrant amounts of MMPs or MMP activity. These are also include as tetracycline compound responsive states which may be treated using compounds of the invention.

Examples of matrix metalloproteinase associated states ("MMPAS's") include, but are not limited to, arteriosclerosis, corneal ulceration, emphysema, osteoarthritis, multiple sclerosis (Liedtke et al., *Ann. Neurol.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et al., *Biochim. Biophys. Acta* 1987, 907:191-217; Li et al., *Mol. Carcinog.* 1998, 22:84-89)), metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8; 238-247). Other MMPAS include those described in U.S. Pat. Nos. 5,459,135; 5,321,017; 5,308,839; 5,258,371; 4,935,412; 4,704,383, 4,666,897, and U.S. Pat. No. RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amylotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

Other examples of tetracycline compound responsive states are described in WO 03/005971A2 and U.S. Patent Application Publication No. 20040214800, each of which is incorporated herein by reference.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of an IPAS. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843,925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited to, asthma, cystic fibrosis, and emphesema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,8391 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

Pharmaceutical Compositions of the Invention

The invention also pertains to pharmaceutical compositions comprising a therapeutically effective amount of a tetracycline compound (e.g., a compound of Formula I, II, III, IV, V, VI, VII, VIII, IX, X, XI, XII, XIII, XIV, XV, XVI or XVII or any other compound described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays (e.g., aerosols, etc.), creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The compositions of the invention may be formulated such that the tetracycline compositions are released over a period of time after administration.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, II, III, IV, V, VI, VII, VIII, IX, X, XI, XII, XIII, XIV, XV, XVI or XVII or any other compound described herein, for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Example 1

Preparation of 7-(1,2,3,6-tetrahydro-pyridin-4-yl)-sancycline

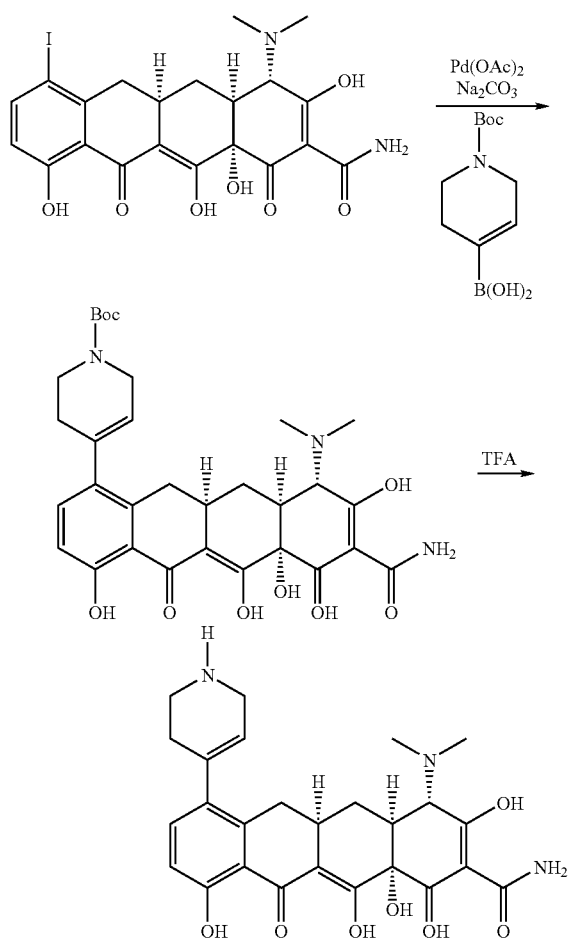

In a 500 mL two-neck round bottom flask, 7-iodo-sancycline TFA salt (654 mg, 1 mmol) and Pd(OAc)$_2$ (22 mg, 0.1 mmol) were taken in 100 mL of MeOH. The reaction mixture was then heated to 70° C. under argon. After 5 minutes, Na$_2$CO$_3$ (420 mg, 4 mmol, a saturated solution in 10 mL of water) was added. A yellow precipitate was obtained which was further heated at 70° C. for 10 minutes. To this solution, 4-N,N-dimethylamino-3-pyridinyl-boronic acid (248 mg, 1.5 mmol, dissolved in 10 mL of DMF) was added and the reaction mixture was heated for another 2 hours. Progress of the reaction was monitored by HPLC and LC/MS. The reaction was completed in 2 hours. Reaction mixture was filtered through celite to remove the catalyst. Solvent was then evaporated to dryness and the crude material was precipitated using MeOH/diethyl ether (20/200 mL). Brown-yellow precipitate was filtered and dried under vacuum. The solid obtained was taken in 20 mL of TFA and stirred at room temperature for 5 minutes. TFA was removed and purification was done on a C-18 Luna column using a 5-25% organic gradient (CH$_3$CN/ 0.1% TFA and Water/0.1% TFA). Fractions collected were dried in vacuo and the solid obtained was converted to its HCl salt using a saturated solution of methanol-HCl (20 mL). Compound was dried overnight over P$_2$O$_5$ to yield the product as a yellow powder. MS: (m/z) 496.2391. $^1$H NMR (300 MHz, CD$_3$OD): δ 7.32 (d, 1H), 6.75 (d, 1H), 5.51 (s, 1H), 3.95 (s, 1H), 3.71 (s, 2H), 3.35 (m, 2H), 2.94-2.76 (m, 8H), 2.52-2.39 (m, 1H), 2.36-2.31 (m, 1H), 2.05 (m, 1H), 1.48-1.47 (m, 1H).

Example 2

Preparation of 7-(1-isobutyl-1,2,3,6-tetrahydro-pyridin-4-yl)-sancycline

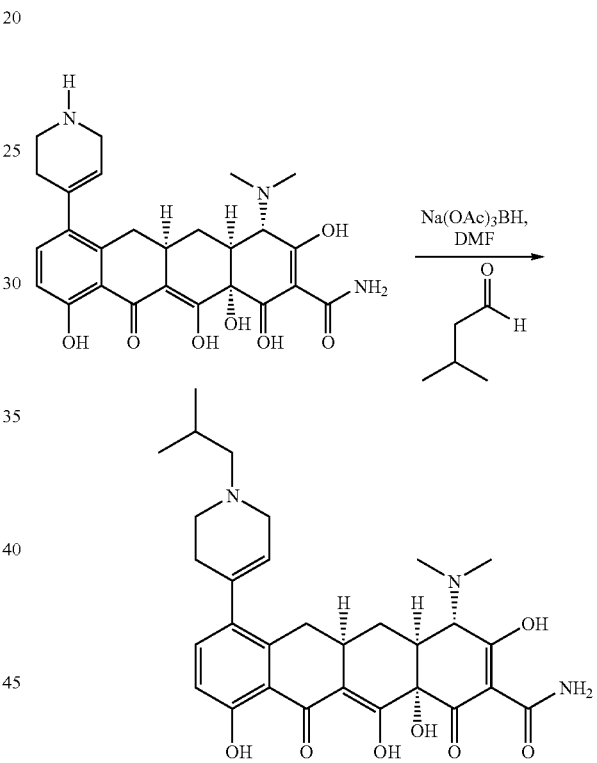

In 40 mL glass vial, 7-(1,2,3,6-tetrahydro-pyridin-4 yl)-sancycline (495 mg, 1 mmol) and InCl$_3$ (11 mg, 0.1 mmol) were taken in DMF (20 mL) under an argon atmosphere. Isobutyraldehyde (144 μL, 2 mmol) was added to the reaction mixture and it was further stirred at room temperature for 20 minutes. To this sodium cyanoborohydride (186 mg, 3 mmol) was added, and the reaction solution was stirred at room temperature for another 4 hours. Completion of the reaction was confirmed by HPLC and LC-MS. Solvent was then evaporated to dryness, redissolved in water/0.1% TFA and purified using a C-18 Luna column using a 7-35% organic gradient (CH$_3$CN/0.1% TFA and water/0.1% TFA). The Fractions collected were dried in vacuo and the solid obtained was converted to its HCl salt using a saturated solution of Methanol-HCl (20 mL). The compound was then dried overnight over P$_2$O$_5$ to yield the product as a yellow powder. MS: (m/z) 552.3212. $^1$H NMR (300 MHz, CD$_3$OD): δ 7.26-7.23 (m, 1H), 6.74-6.72 (m, 1H), 5.50-5.46 (m, 1H), 4.02 (s, 1H), 3.92-3.88 (m, 1H), 3.65-3.60 (m, 2H), 3.03-2.76 (m, 1H), 2.33-2.28 (m, 1H), 2.20-2.15 (m, 3H), 1.18-1.04 (m, 1H), 1.04-0.99 (m, 6H).

Example 3

Preparation of 7-imidazo-[1,2-a]-pyrimidin-2-yl-sancycline

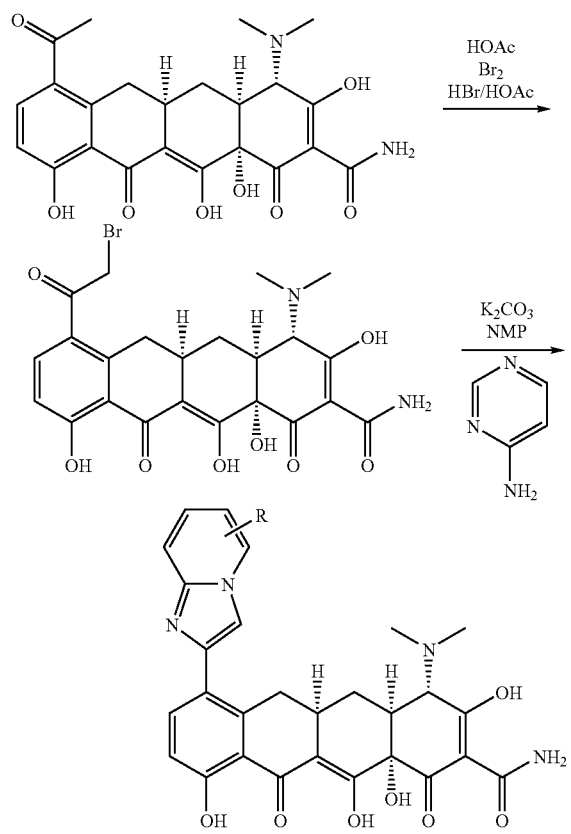

In a 40 mL glass vial, 7-acetyl sancycline (1 g, 2.19 mmol) and $Na_2SO_3$ (200 mg, to prevent oxidation of products) were taken in acetic acid (4 mL) and water (1 mL). The reaction mixture was stirred until contents dissolved (5 minutes) under argon atmosphere. To this solution, HBr (33 wt % solution in HOAc, 3 mL, 0.02 mmol) was slowly added. Dropwise addition of bromine (0.15 mL, 1.21 mmol) gave an exothermic reaction. The reaction was monitored by HPLC and LC-MS and completion of the reaction was observed within 15 minutes. HPLC/LC-MS indicates the formation of mono and bis-bromo-substituted products. An amount of 200 mL of diethyl ether was added to the reaction mixture to form a precipitate. The ether was decanted, and 200 mL fresh ether added, and decanted once again. The yellow precipitate was filtered and dried under vacuum for 5 minutes and was used for the next step without any purification. Crude 2'-bromo-7-acetyl-sancycline was dissolved in NMP (10 mL) and $Na_2SO_3$ (200 mg) was added to prevent oxidation of products. $K_2CO_3$ (1 g, 7.25 mmol) was added to the reaction solution, followed by addition of 2-amino-pyrimidine (1 g, 10.52 mmol). The reaction was monitored by HPLC and LC-MS. Starting material was consumed after 30 minutes. Crude material was precipitated in diethyl ether (200 mL); the precipitate was filtered through a sintered glass funnel, and washed with fresh ether. A dark yellow solid of crude material (0.95 g) remained. The crude material was purified on a C-18 Luna column using a 10-30% organic gradient ($CH_3CN$ with 0.1% TFA and Water with 0.1% TFA). The purified compound was dried in vacuo and redissolved in methanol (20 mL) saturated with HCl to exchange the salt. The compound was dried overnight over $P_2O_5$ to yield the product as a yellow powder. MS: (m/z) 532.2317. $^1$H NMR (300 MHz, $CD_3OD$): δ 9.22 (d, 1H), 9.03 (d, 1H), 8.24 (s, 1H), 7.72-7.62 (m, 2H), 7.04 (d, 1H), 4.13 (s, 1H), 3.18-2.94 (m, 9H), 2.18 (t, 1H), 1.59 (d, 1H), 1.26 (q, 1H).

Example 4

Preparation of 7-{3'-[(ethyl-methyl-amino)-methyl]-phenyl}-sancycline

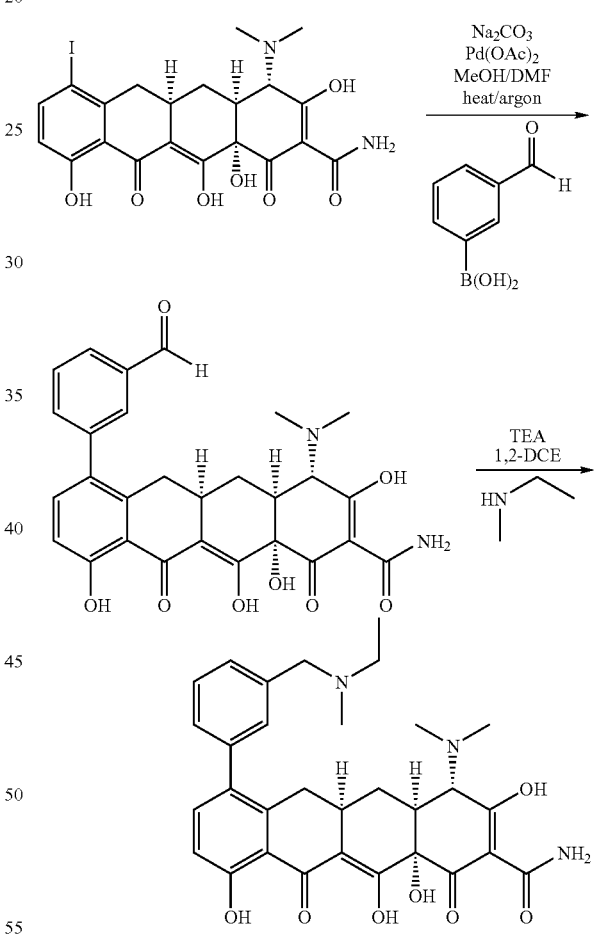

A mixture of 7-(3'-formyl-phenyl)-sancycline (389 mg, 0.75 mmol), N-methyl-N-ethylamine (644 μL, 7.5 mmol) and triethylamine in 1,2-dichloroethane was stirred overnight. Sodium triacetoxyborohydride (477 mg, 2.25 mmol) was added and stirred for 5 hours. Excess sodium triacetoxyborohydride (318 mg, 1.5 mmol) was added and stirred for additional 2.5 hours. The solvent was evaporated and purified by prep-HPLC (10-40% acetonitrile in water). This was converted to hydrochloride salt to give a yellow solid: MS (Mz+ 1=562); $^1$H NMR (300 MHz, $CD_3OD$) δ7.56-7.38 (5H), 6.90 (m, 1H), 4.46 (m, 1H), 4.25 (m, 1H), 4.03 (d, J=1.0 Hz), 3.31

(m, 1H), 3.19-2.72 (13H), 2.51 (m, 1H), 2.00 (m, 1H), 1.50 (m, 1H), 1.37 (t, 3H, J=7.3 Hz).

Example 5

Preparation of 7-{[3'-(2-methoxy-ethylamino)-methyl]-furan-2'-yl-methyl}-sanscycline

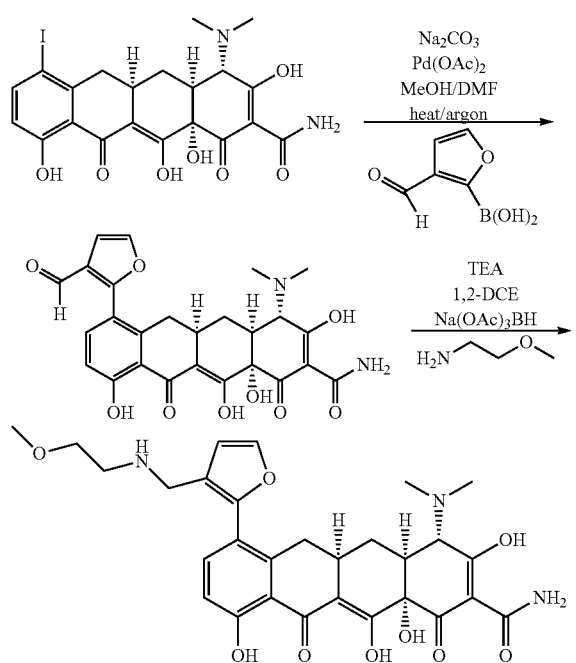

A mixture of 7-(3'-formyl-furan-2'yl)-sancycline (1.02 g, 2 mmol) and 2-methoxyethylamine (348 µL, 4 mmol) in 1,2-dichloroethane (60 mL) was stirred for 1 hour. Sodium triacetoxyborohydride (1.272 g, 6 mmol) was added and stirred for 7 hours. The solvent was evaporated and purified by prep-HPLC to give a yellow solid: MS (Mz+1=568); $^1$H NMR (300 MHz, CD$_3$OD) δ 7.67 (m, 1H), 7.50 (m, 1H), 6.96 (m, 1H), 7.77 (m, 1H), 4.09-3.98 (3H), 3.59 (m, 2H), 3.33 (s, 3H), 3.16-2.93 (m, 10H), 2.69 (m, 1H), 2.46 (m, 1H), 2.14 (m, 1H), 1.55 (m, 1H).

Example 6

Preparation of 7-(5'-dimethylaminomethyl-1H-pyrrol-2-yl)-sancycline

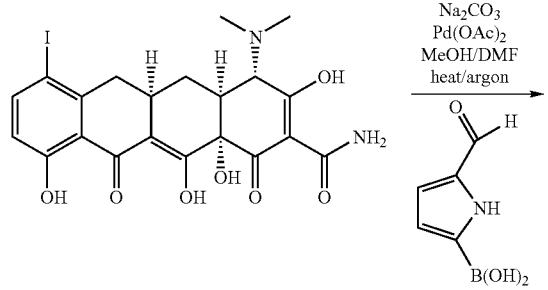

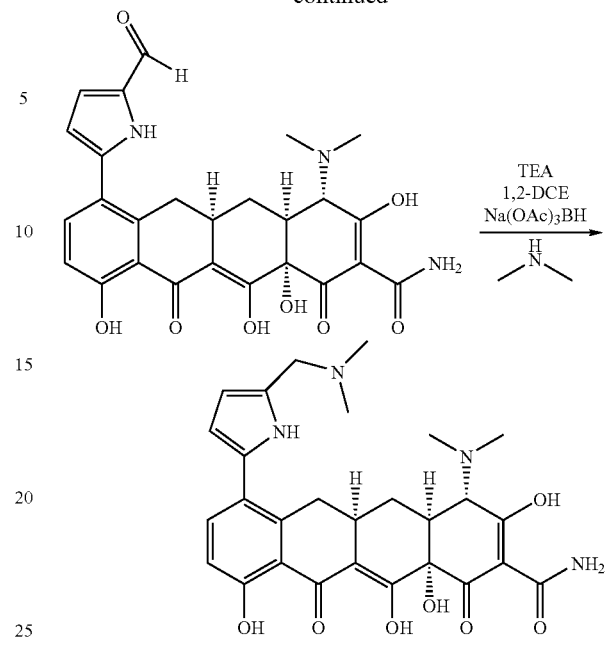

A mixture of 7-(1'-Boc-5'-formyl-pyrrol-2'-yl)-sancycline (262.2 mg, 0.36 mmol), dimethylamine hydrochloride (148 mg, 1.8 mmol), and triethylamine (254 µL, 1.8 mmol) in 1,2-dichloroethane (17 mL) was stirred for 1 hour. Sodium triacetoxyborohydride was added and stirred overnight, after which LC-MS showed the completion of the reaction. The solvent was evaporated and purified by prep-HPLC (12-40% acetonitrile in buffer). The resulting residue (85 mg) was stirred in 5 mL trifluoroacetic acid for 2 hour. Trifluoroacetic acid was evaporated and purified by prep-HPLC (10-40% acetonitrile in water). The solvent was evaporated to give a yellow solid: MS (Mz+1=537); $^1$H NMR (300 MHz, CD$_3$OD) δ 10.89 (s, 1H), 7.50 (m, 1H), 6.87 (m, 1H), 6.39 (brt, 1H), 6.14 (brd, 1H), 4.27 (s, 2H), 4.00 (s, 1H), 3.13-2.84 (9H), 2.81 (s, 6H), 2.49 (m, 1H), 2.00 (m, 1H), 1.55 (m, 1H).

Example 7

Preparation of 7-[2-(4-methyl-piperidin-1-yl)-acetyl]-sancycline

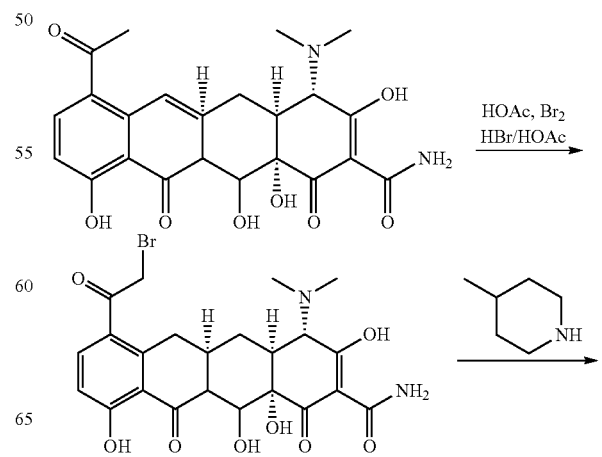

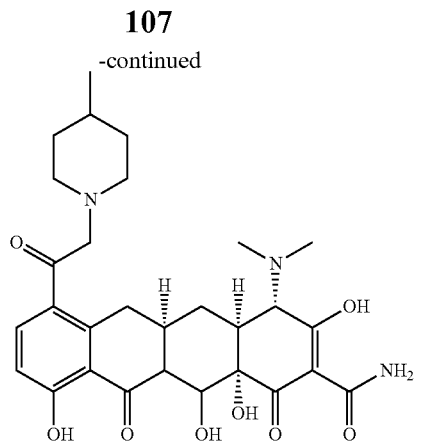

7-acetyl sancycline (1 g, 2.19 mmol) was combined with acetic acid (4 mL), water (1 mL) and HBr (33 wt % solution in AcOH, 2 mL, 0.01 mmol) in a 40 mL glass vial. The reaction mixture was stirred under argon until the contents were dissolved (5 minutes). Bromine (0.15 mL, 1.21 mmol) was added dropwise to the solution (an exothermic reaction). Reaction was monitored by HPLC and LC-MS, and the starting material was consumed within 15 minutes. Mono and bis-substituted bromine products were both detected. An amount of 400 mL of diethylether was added to the reaction solution and a bright yellow solid precipitate was formed. The ether was decanted, 400 mL fresh ether was added, and then decanted once again. Acetonitrile (300 mL) was added to the resulting yellow precipitate and the mixture was filtered through filter paper. The filtrate was dried in vacuo to yield a dark yellow solid. The crude bromo acetyl sancycline was dissolved in DMF (20 mL) in a 100 mL round bottom flask. Argon line was attached to the reaction. TEA (1 mL, 7.19 mmol) was added, followed by 4-methylpiperidine (1 mL, 8.1 mmol). The reaction was monitored by HPLC and LC-MS and the starting material was consumed after 30 minutes. Methanol (50 mL) was added to quench the reaction, and the solvent was dried in vacuo. The crude material was purified on a C-18 Luna column using a 10-30% organic gradient ($CH_3CN$ with 0.1% TFA and water with 0.1% TFA). The purified compound was dried in vacuo and redissolved in HCl saturated methanol to exchange the salt. The compound was dried overnight over $P_2O_5$ to yield the product as a yellow powder. MS: (m/z) 553. $^1H$ NMR (300 MHz, $CD_3OD$) δ 7.99 (m, 1H), 6.93 (m, 1H), 4.89 (m, 1H), 4.61 (m, 1H), 4.07 (s, 1H), 3.68 (m, 1H), 3.56 (m, 1H), 3.30 (m, 1H), 3.11 (m, 2H), 3.01 (m, 7H), 2.47 (m, 1H), 2.15 (m, 1H), 1.89 (m, 2H), 1.55 (m, 4H), 0.96 (d, J=9 Hz, 3H).

Example 8

Preparation of 7-[2-(1-methyl-1H-pyrrole-2-yl methyl amino)-acetyl]-sancycline

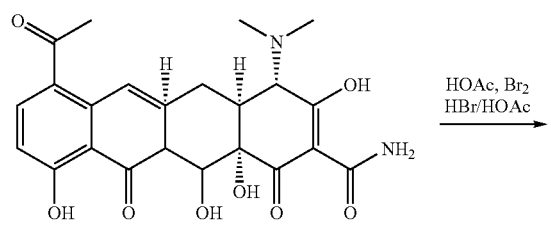

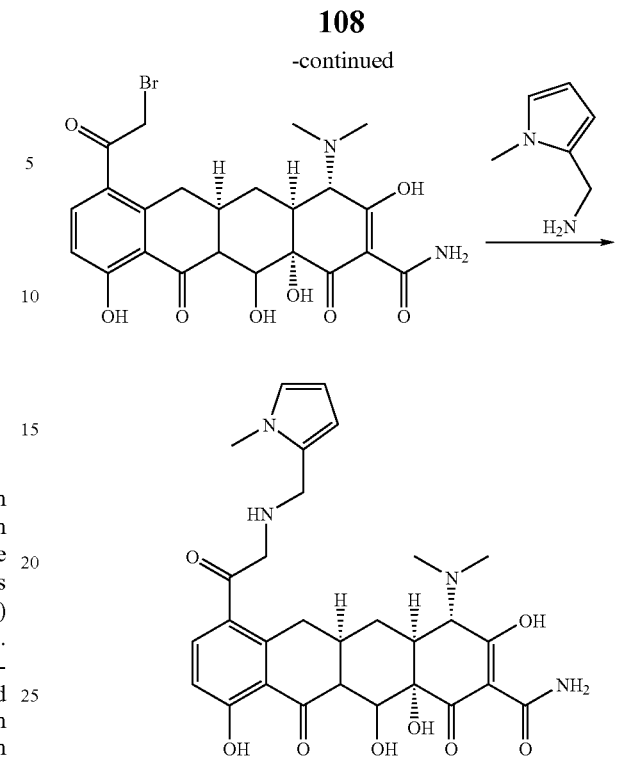

7-acetyl sancycline (1 g, 2.19 mmol) was combined with acetic acid (4 mL), water (1 mL) and HBr (33 wt % solution in AcOH, 3 mL, 0.02 mmol) in a 40 mL glass vial. $Na_2SO_3$ (200 mg) was added to prevent oxidation of products. The reaction mixture was stirred under argon until contents were dissolved (5 minutes). Bromine (0.15 mL, 1.21 mmol) was added dropwise to the reaction solution (an exothermic reaction). The reaction was monitored by HPLC and LC-MS, and the starting material was consumed within 15 minutes. Mono and bis-substituted bromine products were both detected. An amount of 400 mL of diethylether was added to the reaction solution and a bright yellow solid precipitate was formed. The ether was decanted, 400 mL fresh ether added, and then decanted once again. Acetonitrile (300 mL) was added to the yellow precipitate, and the mixture was filtered through filter paper. The filtrate was dried in vacuo to yield a dark yellow solid. The crude bromo acetyl sancycline was dissolved in NMP (12 mL). $Na_2SO_3$ (200 mg) was added to prevent oxidation of products. $K_2CO_3$ (1 g, 7.25 mmol) was added to the reaction solution, followed by (1-methyl-1H-pyrrole-2-yl)-methylamine (1 mL, 7.25 mmol). The reaction was monitored by HPLC and LC-MS and the starting material was consumed after 30 minutes. The crude material was precipitated in diethyl ether (500 mL), filtered through a sintered glass funnel, and washed with fresh ether. A dark yellow solid of crude material remained. The crude material was purified on a C-18 Luna column using a 10-30% organic gradient ($CH_3CN$ with 0.1% TFA and water with 0.1% TFA). Purified compound was dried in vacuo and redissolved in HCl saturated methanol to exchange the salt. The compound was dried overnight over $P_2O_5$ to yield the product as a yellow powder. MS: (m/z) 564. $^1H$ NMR (300 MHz, $CD_3OD$) δ 7.93 (m, 1H), 6.91 (m, 1H), 6.74 (m, 1H), 6.27 (m, 1H), 5.99 (m, 1H), 4.71 (m, 1H), 4.44 (m, 1H), 4.27 (m, 2H), 4.07 (s, 1H), 3.71 (s, 3H), 3.58 (m, 1H), 3.28 (s, 1H), 3.15 (s, 1H), 2.95 (m, 7H), 2.38 (m, 1H), 2.11 (m, 1H), 1.55 (m, 1H).

Example 9

Preparation of 7-(3'-dimethylamino-propenyl)-sancycline

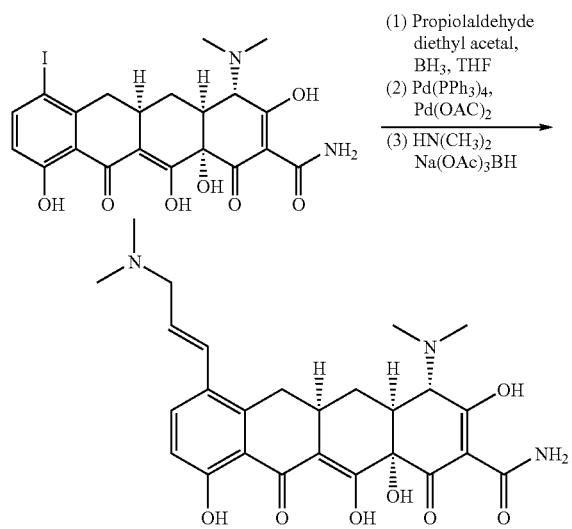

A solution of propionaldehyde diethyl acetal I (12.9 mL, 90 mmol) in 60 mL THF was cooled in an ice-bath and BH$_3$/THF was added dropwise and stirred. A mixture of 7-iodosancycline trifluoroacetate (5.889 g, 9 mmol), Pd(PPh$_3$)$_4$, and Palladium (II) acetate in methanol (160 mL) was purged with argon. A solution of sodium carbonate (3.82 g, 36 mmol) in water (40 mL) was added and purged for additional 5 minutes. To this mixture was added DMF (40 mL) and reaction mixture I and further purged with argon. The reaction mixture was heated to 44° C. and stirred at this temperature for 3 hour. This intermediate (MS, Mz+1=469) was purified by short DVB column followed by prep-HPLC. To a stirred solution of the intermediate (250 mg, 0.43 mmol), dimethylamine hydrochloride (70 mg, 0.86 mmol), and triethylamine (120 μL, 0.86 mmol) in 1,2-dichloroethane (25 mL) was added sodium triacetoxyborohydride (182 mg, 0.86 mmol) and the reaction mixture was stirred for 1 hour. The solvent and excess reagent was evaporated. The product was purified by prep-HPLC (5-25% acetonitrile in water) to give a yellow solid: MS (Mz+1=562); $^1$H NMR (300 MHz, CD$_3$OD) δ7.79 (d, J=8.8 Hz, 1H), 7.43 (d, J=15.5 Hz, 1H), 6.91 (d, J=8.8 Hz, 1H), 6.14 (dt, J=15.5 Hz, 7.7 Hz, 1H), 4.10 (s, 1H), 3.94 (d, J=7.4 Hz, 2H), 3.28-2.89 (15H), 2.42 (m, 1H), 2.20 (m, 1H), 1.67 (m, 1H).

Example 10

Preparation of 7-(4-methyl-piperidin-1-yl methyl)-sancycline

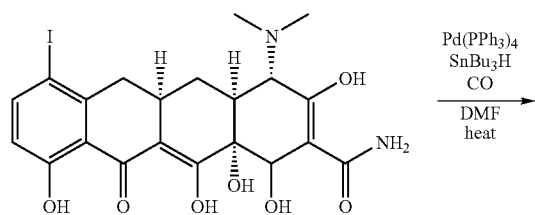

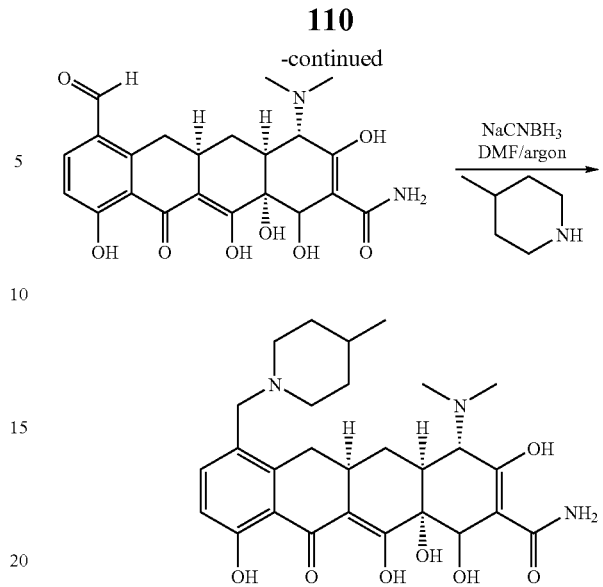

7-iodo sancycline (6 g, 9.17 mmol) was combined with NaOAc (0.75 g, 9.17 mmol) and DMF (100 mL) in an oven-dried 500 mL 2-neck round bottom flask. The reaction mixture was stirred at ambient temperature for 1 hour under argon. An amount of Pd(PPh$_3$)$_4$ (1.06 g, 0.917 mmol) was added, and the reaction mixture was purged with CO for 20 minutes. The reaction mixture was placed in a 70° C. preheated oil bath, and stirred under CO atmosphere for 1 hour. An amount SnBu$_3$H (3.2 g, 1.1 mmol) was added via syringe pump over 2 hours. The reaction was monitored by HPLC and LC-MS, and the starting material was consumed 2 hours post tin addition. The reaction was quenched with CH$_3$CN (50 mL), and the solvent was evacuated in vacuo. Water (1 L with 0.1% TFA) was added, and a heterogeneous mixture was formed. After filtration through celite to remove unwanted precipitate, the aqueous layer was loaded onto a prepared DVB column. The product was eluted with 30% organic gradient (CH$_3$CN with 0.1% TFA and water with 0.1% TFA). The solvent was evaporated to yield 7-formyl sancycline product as a yellow solid. The 7-formyl sancycline (0.5 g, 1.13 mmol) was combined with InCl$_3$ (0.025 g, 0.13 mmol), 4-methylpiperidine (0.267 mL, 2.26 mmol) and DMF (10 mL) in a glass vial. The reaction mixture was stirred at ambient temperature for 30 minutes under argon. An amount of NaCNBH$_3$ (0.1 g, 1.58 mmol) was added to the reaction mixture, and the progress of the reaction was monitored by HPLC and LC-MS. After stirring overnight at ambient temperature, the starting material was consumed. Methanol (10 mL) was added to quench the reaction and the solvent was evacuated in vacuo. The crude material was purified on a C-18 Luna column using a 10-30% organic gradient (CH$_3$CN with 0.1% TFA and water with 0.1% TFA). The purified material was concentrated, and redissolved in HCl saturated methanol (20 mL) to exchange the salt. After drying overnight under high vacuum the product was obtained as a yellow powder. MS: (m/z) 525. $^1$H NMR (300 MHz, CD$_3$OD) δ 7.54 (m, 1H), 6.86 (m, 1H), 4.22 (m, 2H), 4.03 (s, 1H), 3.44 (m, 1H), 3.27 (m, 1H), 3.15 (m, 1H), 2.94 (m, 9H), 2.31 (m, 2H), 1.61 (m, 6H), 0.90 (d, J=7 Hz, 3H).

Example 11

Preparation of 7-(4-dimethylamino-pyridin-3-yl)-sancycline

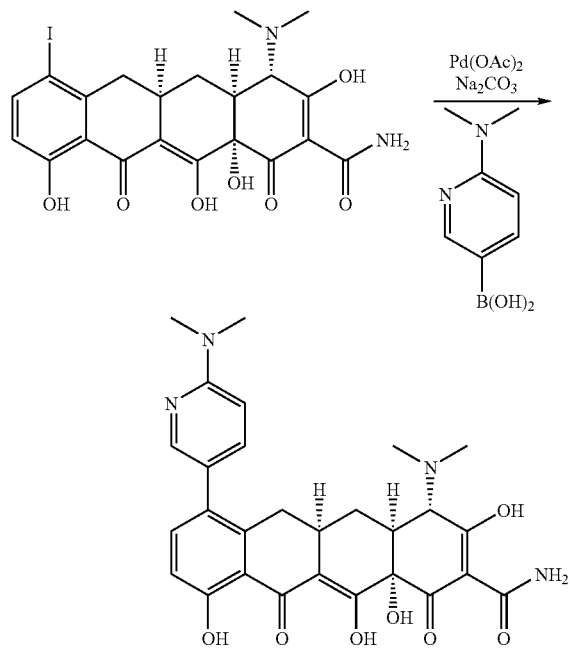

In a 500 mL two-neck round bottom flask, 7-iodo-sancycline TFA salt (654 mg, 1 mmol) and Pd(OAc)$_2$ (22 mg, 0.1 mmol) were taken in 100 mL of MeOH. The reaction mixture was then heated to 70° C. while purging with argon. After 5 minutes, Na$_2$CO$_3$ (420 mg, 4 mmol, a saturated solution in 10 mL of water) was added to the reaction mixture. A yellow precipitate was obtained which was further heated at 70° C. for 10 minutes. To this, 4-dimethylamino-pyridin-3-yl-boronic acid (248 mg, 1.5 mmol, dissolved in 10 mL of DMF) was added and the reaction was continued for another 3 hours. The progress of the reaction was monitored by HPLC and LC/MS. The reaction was completed in 3 hours. It was then filtered through celite to remove the catalyst. The solvent was evaporated to dryness and the crude material obtained was purified using preparative HPLC using a C-18 Luna column with a 10-40% organic gradient (CH$_3$CN/0.1% TFA and Water/0.1% TFA). The fractions collected were dried in vacuo and the solid obtained was converted to its HCl salt using a saturated solution of methanol-HCl (20 mL). The compound was dried overnight over P$_2$O$_5$ to yield the product as a yellow powder. MS: (m/z) 535.2242. $^1$H NMR (300 MHz, CD$_3$OD): δ 8.10 (d, 1H), 7.85 (s, 1H), 7.36 (d, 1H), 7.22 (d, 1H), 6.86 (d, 1H), 3.98 (s, 1H), 3.20 (s, 6H), 3.08-2.82 (m, 8H), 2.49 (m, 1H), 2.45 (t, 1H), 1.84-1.47 (m, 1H), 1.44-1.19 (m, 1H).

Example 12

Preparation of 7-(4'-hydroxy-phenyl)-sancycline

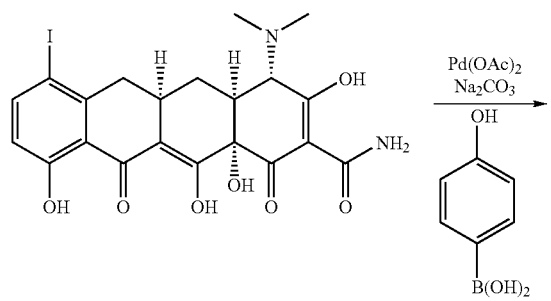

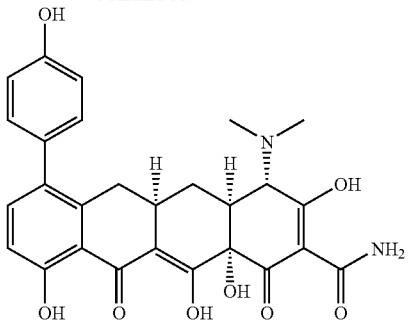

A solution of 7-iodosancycline trifluoroacetate (654.43 mg, 1 mmol), Pd(PPh$_3$)$_4$ (115.6 mg, 0.1 mmol), and palladium (II) acetate (22.5, 0.1 mmol) in 20 mL methanol was purged with argon for 10 minutes. A solution of sodium carbonate (424 mg, 4 mmol) in 5 mL water was added and the mixture was purged for additional 5 minutes. A solution of 4-hydroxyphenyl boronic acid pinacol ester in DMF (5 mL) was purged with argon and added to the mixture. The reaction mixture was heated to 65° C. and stirred at the same temperature for 3 h. The reaction mixture was cooled and filtered through celite pad. The filtrate was taken, solvent evaporated and the crude product was precipitated from ether. It was further purified by prep-HPLC (20-40% acetonitrile in water) to give a yellow solid: MS (Mz+1, 507); $^1$H NMR (300 MHz, CD$_3$OD) δ 7.39 (d, J=8.6 Hz, 1H), 7.08 (d, J=8.5 Hz, 1H), 6.84 (m, 1H), 2.85 (9H), 2.44 (m, 1H), 2.05 (m, 1H), 1.55 (m, 1H).

Example 13

Preparation of minocycline-2-acetyl amide

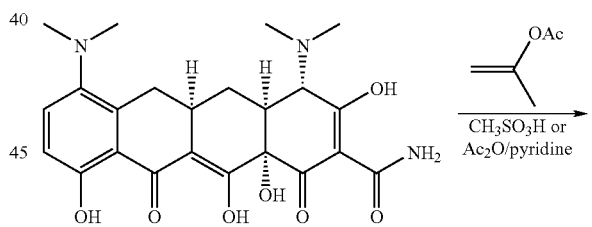

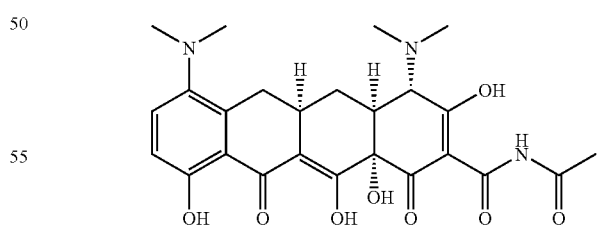

To a suspension of minocycline (0.1 g, 0.19 mmol) in pyridine was added acetic anhydride with stirring. The suspension became a clear solution. The reaction mixture was stirred at room temperature overnight. The product was obtained after HPLC purification as a yellow powder. MS: (M+1=500); $^1$H NMR (300 MHz, CD$_3$OD) δ 7.87 (d, J=8.8 Hz, 1H), 7.14 (d, J=9 Hz, 1H), 4.83 (d, J=3 Hz, 1H), 3.98 (m, 1H), 3.49-3.10 (15H), 2.60 (m, 1H), 2.40 (s, 3H), 19 (m, 1H).

Example 14

Preparation of 7-(3,4,5-trifluorophenyl)-9-aminomethyl minocycline

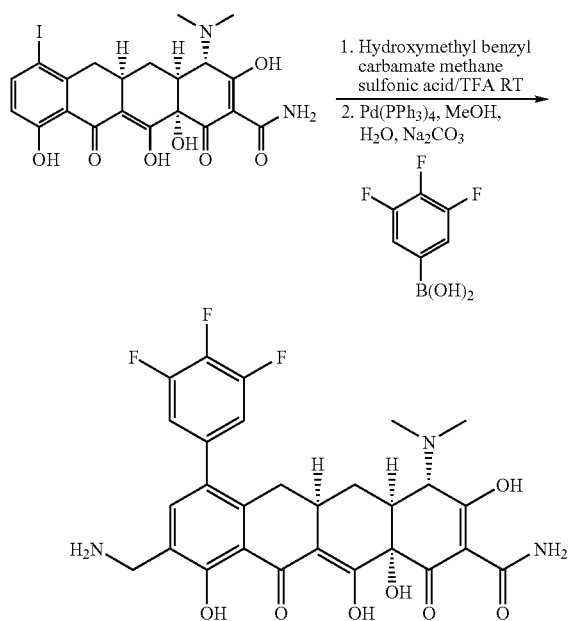

7-iodo sancycline in methanesulfonic acid/TFA was treated with excess hydroxymethylbenzyl carbamate (~5 equivalents). The resulting reaction mixture was stirred for several hours. The solvent was evaporated and to the residue was added to methanol/water. The insoluble material was filtered and the filtrate was dried to yield the crude product. The desired intermediate was obtained by preparative HPLC. To a solution of 7-iodo-9-aminomethylsanscycline trifluoroacetate in methanol was added 0.2 equiv of tetrakis(triphenylphosphine)Palladium (0) and the resulting solution was stirred under argon for 5 minutes. An amount of 3 equivalents of sodium carbonate in water was added followed by substituted phenylboronic acid. The resulting solution was heated at 70° C. for several hours. The catalyst was filtered through celite, and the filtrate was dried to yield the crude reaction product. The desired material was isolated via reverse-phase preparative HPLC as a yellow solid. MS: M+1=574; $^1$H NMR (300 MHz, CD$_3$OD), δ d 7.54 (s, 1H), 7.15 (t, 2H), 4.2 (s, 2H), 4.08 (s, 1H), 2.98-2.50(m, 10H), 2.1 (bd, 1H), 1.6 (m, 1H).

Example 15

Preparation of 9-[(2-dimethylamino-acetylamino) methyl]-doxycycline

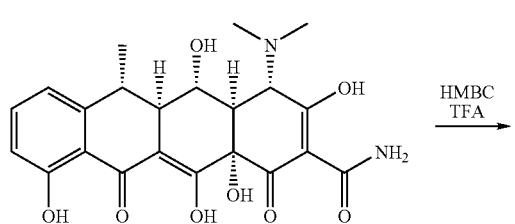

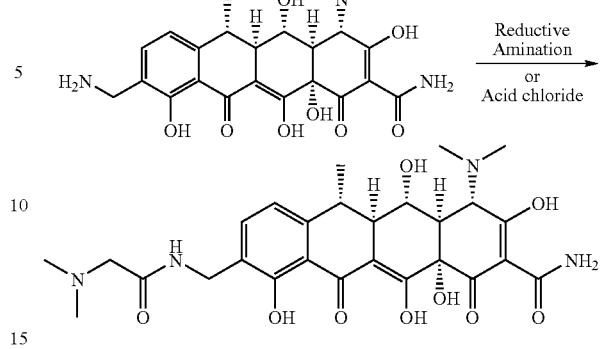

An amount of 5 g of doxycycline in 50 ml of TFA was treated with excess hydroxymethylbenzyl carbamate (HMBC) (~5 equivalents). Several drops of sulfuric acid were then added and the resulting reaction mixture was stirred for several hours. The solvent was evaporated and to the residue was added methanol/water. The insoluble material was filtered and the filtrate was dried to yield the crude product. The intermediate (9-aminomethyl doxycycline) was obtained by preparative HPLC.

An amount of 800 mg of 9-aminomethyl-doxycycline was reacted with 3 equivalents of N,N-dimethylglycinyl chloride in the presence of diisopropylethylamine (3 equivaltents) in DMF. The reaction mixture was stirred at room temperature for several hours. The product was obtained by preparative HPLC as a yellow solid. MS: M+1=559; $^1$HNMR (300 MHz, CD$_3$OD) δ d 7.54 (d, 1H), 6.96(d, 1H), 4.47(s, 2H), 4.44(s, 1H), 3.98(s, 2H), 3.56(q, 1H), 3.34(s, 1H), 2.99-2.75(m, 14H), 2.59(q, 1H), 1.55 (d, 3H).

Example 16

Preparation of 7-hydroxy-9-[(2,2-dimethyl propylamino)-methyl]-sancycline

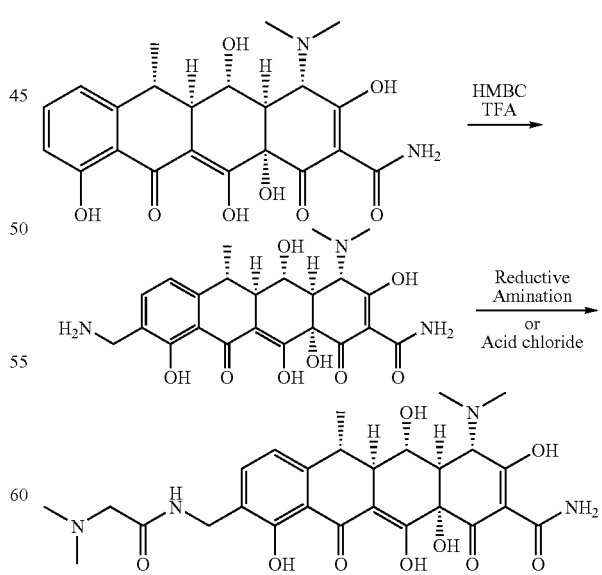

An amount of 9-[(2,2-dimethyl propylamino)-methyl]-minocycline (2.0 g, 3.5 mmol) was added to DDI water (40 mL) and pH adjusted to pH 11 using a 1.0 N solution of sodium hydroxide. Subsequently, sodium metaperiodate (700 mg, 3.29 mmol) was added to the above solution and allowed to stir at room temp for 40 seconds. Subsequently, a pre-dissolved aqueous solution of ascorbic acid (5.0 g, 28 mmol) in DDI water (80 mL) was added to quench the above reaction. The reaction was added to DDI water (1.0 L) and the pH was lowered to pH 2 using trifluoroacetic acid. The solution was then filtered and concentrated onto a plug of divinyl benzene (DVB) resin, eluted from the resin with acetonitrile and concentrated via rotary evaporation to 800 mg crude product. The crude product was purified by HPLC using a C-18 column, triethanolamine (0.002 M) pH 7.4 aqueous buffer and acetonitrile as the organic phase. The fractions containing the desired compound were loaded onto a DVB plug, washed with aqueous 0.05 N HCl (1.0 L) and eluted with acetonitrile to give the HCl salt of the product as a yellow powder. MS: M+1=530; $^1$H-NMR (300 MHz, CD$_3$OD) δ 7.1-7.3 (s, 1H), 4.2-4.3 (s, 2H), 4.0-4.1 (s, 1H), 2.9-3.2 (m, 8H), 2.8-2.9 (m, 2H), 2.1-2.3 (m, 2H), 1.6-1.9 (m, 1H), 1.0-1.1 (s, 9H).

Example 17

Preparation of 9-methyl minocycline

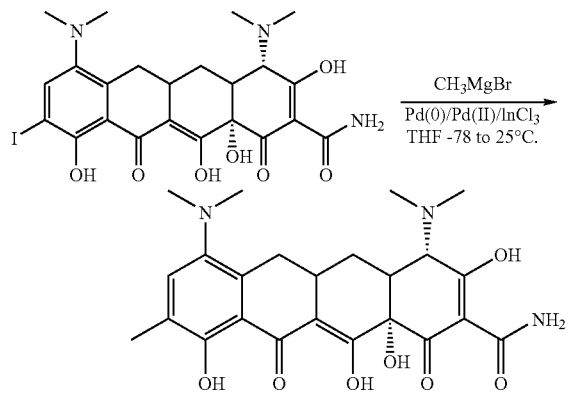

A 1000 mL 2 or 3 neck round-bottomed flask with reflux condenser was charged with anhydrous InCl$_3$ (12.1 g, 40.5 mmol) and dried under vacuum with a heat gun. After flask was cooled to ambient temperature and flushed with argon, anhydrous THF (240 mL) was added. The solution was cooled to −78° C. and methyl MgBr(Cl) (122 mmol) as solution in THF was added. After 15 minutes, the solution was allowed to slowly warm to room temperature to form a clear heterogeneous solution. To the reaction flask was added 9-iodominocycline (21.0 g, 36 mmol) and Pd(t-Bu$_3$P)$_2$ (0.920 g, 1.80 mmol). The solution was heated to reflux under argon until the reaction was complete. After cooling to ambient temperature, the solution was quenched with MeOH (1 mL) and poured into a stirring cold solution of 1M HCl (3 L). After 1 h, the solution was filtered through a pad of celite rinsing with water. The water solution was loaded onto a large fritted funnel containing a bed of prepared DVB resin. At first, cold water (500 mL) was eluted then a gradient of cold acetonitrile/water was eluted in (500 mL) fractions. The fractions containing product were concentrated under reduced pressure and then dried under high vacuum overnight to afford desired product as a dark yellow solid. MS: M+1=472; $^1$H NMR (300 MHz, CD$_3$OD) δ 7.26 (s, 1H), 4.22 (s, 1H), 3.41-3.35 (m, 1H), 2.90-2.52 (m, 15H), 2.21-2.00 (m, 4H), 1.68-1.55 (m, 1H).

Example 18

Preparation 9-(4-pyrazol)-minocycline

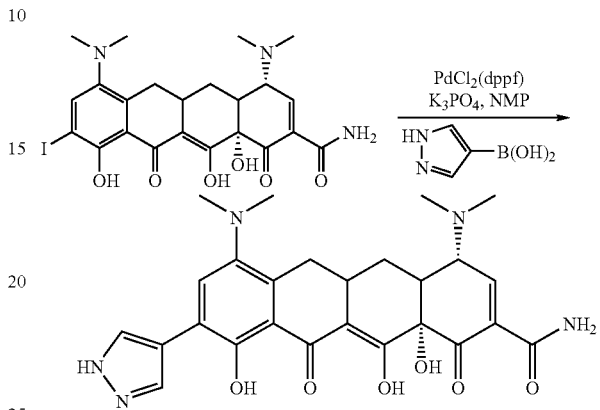

To a solution of anhydrous 9-iodominocycline freebase (2.04 g, 3.5 mmol), pyrazolyl boronic acid (4.38 mmol) and Cl$_2$Pd(dppf) (0.143 g, 0.175 mmol) in NMP (10 mL) was added (10 mL) of 2M K$_3$PO$_4$ in a 20 mL Biotage microwave vial. The secured vial was placed into a Biotage microwave reactor with a temperature setting of 100° C. for 10 minutes. The reaction was cooled to rt and poured into a solution of 1% TFA/H$_2$O (150 mL). The solution was loaded onto a previously prepared funnel of DVB resin (3×10 cm packed DVB column). After loading, water (100 mL) was eluted and finally 1% TFA/CH$_3$CN to elute the desired product. The yellow solution was concentrated under reduced pressure and further purified by preparatory chromatography. The product was obtained as a brown solid. MS: M+1=524; $^1$H NMR (300 MHz, CD$_3$OD) δ 8.69 (s, 1H), 8.32 (s, 1H), 4.18 (s, 1H), 3.41-2.94 (m, 15H), 2.60-2.49 (m, 1H), 2.35-2.29 (m, 1H), 1.73-1.61 (m, 1H).

Example 19

Preparation of 9-(thiazol-2-ylyminocycline

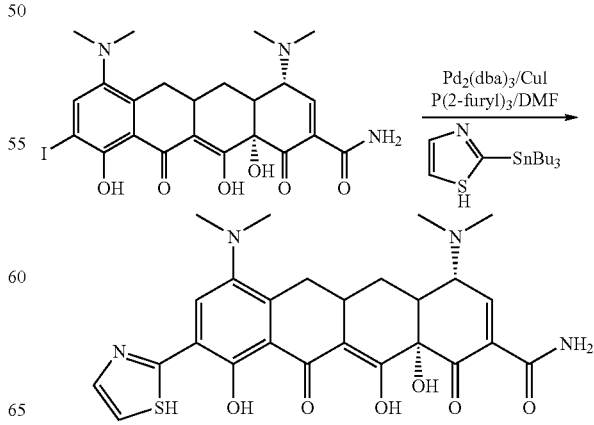

To a solution of anhydrous 9-iodominocycline freebase (2.04 g, 3.5 mmol), thiazol-2-yl stannane (4.38 mmol), CuI (0.067 g, 0.350 mmol), P(2-furyl)$_3$ (0.163 g, 0.700 mmol) and Pd$_2$(dba)$_3$ (0.081 g, 0.088 mmol) in DMF (20 mL) in a 20 mL Biotage microwave vial. The secured vial was placed into a Biotage microwave reactor with a temperature setting of 100° C. for 10 minutes. The reaction was poured into a solution of 1% TFA/H$_2$O (150 mL). The solution was filtered through a plug of Celite rinsing with 1% TFA water solution. The solution was loaded onto a previously prepared funnel of DVB resin (3×10 cm packed DVB column). After loading, water (100 mL) was eluted and finally CH$_3$CN to elute the desired product. The yellow solution was concentrated under reduced pressure and further purified by preparatory chromatography. The product was obtained as an orange-yellow solid. MS: M+1=541; $^1$H NMR (300 MHz, CD$_3$OD) δ 8.88 (s, 1H), 8.12 (d, J=3 Hz, 1H), 7.98 (d, J=3 Hz, 1H), 4.19 (s, 1H), 3.50-2.92 (m, 15H), 2.65-2.53 (m, 1H), 2.40-2.22 (m, 1H), 1.76-1.61 (m, 1H).

Example 20

Preparation of 9-(3-methoxy-pro-1-ynyl)-minocycline

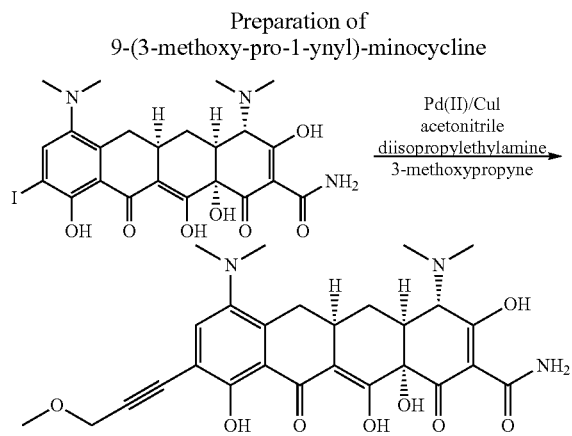

An amount of 9-iodo-minocycline (free-base) (5.00 g, 8.57 mmol), trans-dichlorobis-(triphenylphosphine)palladium(II) (152 mg, 0.22 mmol), palladium(II)acetate (55 mg, 0.24 mmol), copper(I)iodide (92 mg, 0.48 mmol) were loaded in anhydrous acetonitrile (86 mL) in a flame-dried 100 mL round bottom flask equipped with a magnetic stirring bar. The mixture was degassed by bubbling argon through for 10 minutes, and diisopropylethylamine (4.5 mL, 25.83 mmol) was added, followed by 3-methoxy-propyne (1.5 mL, 17.76 mmol). The reaction mixture was then stirred at room temperature for 18 hours while being monitored by LC/MS. After filtration through a pad of celite, the solution was poured into a 1% TFA in water solution (1 L) and purified on a DVB column by eluting with a gradient of 1% TFA in water solution and a 50/50 mixture of methanol and acetonitrile. The major peak was isolated, and all solvents were evaporated. The residue was then purified by preparative HPLC (C18 Lumina). A salt exchange with a 0.2N HCl solution on a DVB column followed by evaporation to dryness then yielded the desired product as a yellow solid. MS: M+1=526. $^1$H-NMR (300 MHz, CD$_3$OD):□8.03 (s, 1H), 4.38 (s, 2H), 4.15 (d, 1H), 3.45 (s, 3H), 3.33-3.36 (m, 1H), 3.24 (s, 6H), 3.06-3.24 (m, 1H), 2.94-3.04 (m, 7H), 2.54 (m, 1H), 2.31 (m, 1H), 1.68 (m, 1H).

Example 21

Preparation of 9-cyano minocycline

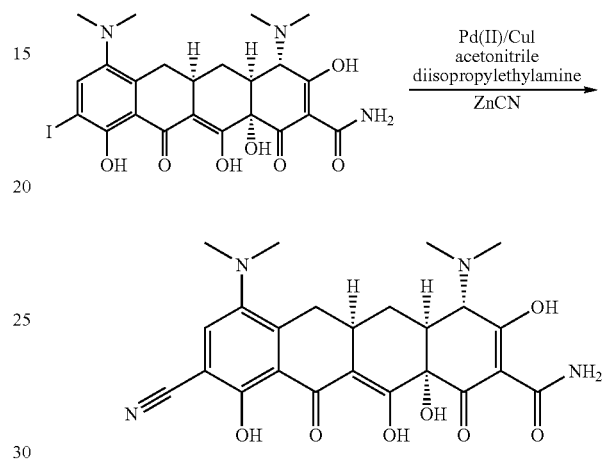

An amount of 9-iodo-minocycline (2.00 g, 3.43 mmol), tetrakis(triphenylphosphine) palladium (0) (97 mg, 0.34 mmol), zinc cyanide (500 mg, 4.17 mmol) were loaded in anhydrous DMF (20 mL) in a dry 20 mL microwave reaction vessel equipped with a magnetic stirring bar.

Argon was bubbled through for 10 minutes, and the vessel was sealed. The reaction mixture was then subjected to the microwave irradiation for 10 minutes at 100° C. with the "heating while cooling" feature and is monitored by LC/MS. The reaction mixture was poured into a 0.1M solution of sodium acetate. The mixture was then filtered through a pad of celite, and washed several times with the 0.1M sodium acetate solution. The resulting aqueous solution was purified on a DVB column (gradient of water and acetonitrile). After evaporation of the organic solvent, the resulting residue is then purified by preparative HPLC (C18 Lumina). A salt exchange with a 0.2N HCl solution on a DVB column followed by evaporation to dryness then yielded the desired product as a yellow solid. MS: M+1=483. $^1$H-NMR (300 MHz, CD$_3$OD): □8.13 (s, 1H), 4.13 (s, 1H), 3.40 (m, 1H), 2.90-3.16 (m, 14H), 2.52 (m, 1H), 2.28 (m, 1H), 1.65 (m, 1H).

Example 22

Preparation of 9-[5-(2-methoxy-ethylamino)-methyl furan-2-yl]-minocycline

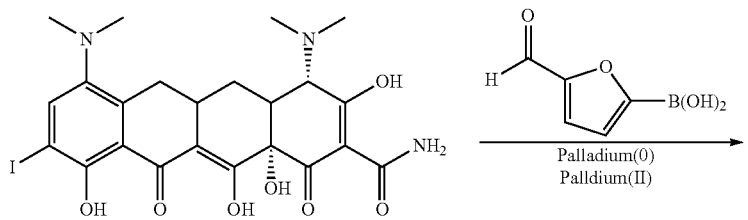

-continued

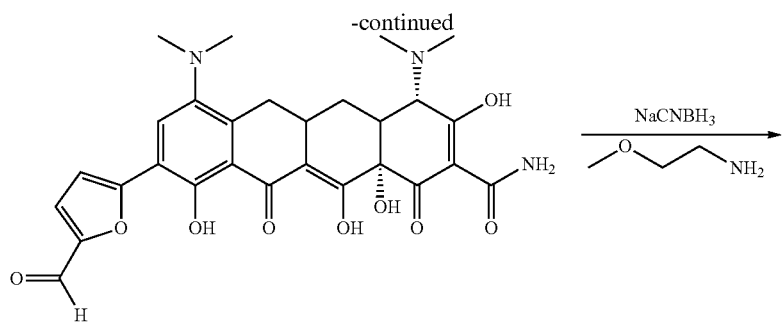

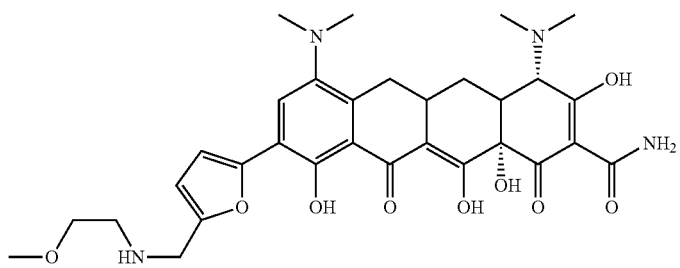

An amount of 9-2-formyl-furany-2-yl minocycline (0.5 g, 0.91 mmol) was combined with 2-methoxyethylamine (0.157 mL, 1.81 mmol) and 1,2-DCE (20 mL) in a glass vial. The reaction mixture was stirred at ambient temperature for 10 minutes under argon. NaCNBH$_3$ (0.086 g, 1.36 mmol) was added to the reaction mixture, and was stirred for 1 hour. Reaction was monitored by HPLC and LC-MS, and the starting material was consumed after 1 hour. Methanol (50 mL) was added to quench the reaction, and the solvent was evacuated in vacuo. The crude material was purified on a C-18 Luna column using a 5-30% organic gradient (CH$_3$CN with 0.1% TFA and water with 0.1% TFA). Solvent was evacuated and, the product was redissolved in HCl saturated methanol (20 mL) to exchange the salt. After drying overnight under high vacuum the product was obtained as a yellow powder. MS: (m/z) 610. $^1$H NMR (300 MHz, CD$_3$OD) δ 8.49 (s, 1H), 7.16 (d, J=3 Hz, 1H), 6.75 (d, J=3 Hz, 1H), 4.37 (s, 2H), 4.12 (s, 1H), 3.67 (m, 2H), 3.37 (s, 4H), 3.31 (m, 7H), 2.98 (m, 7H), 2.51 (m, 1H), 2.32 (m, 1H), 1.67 (m, 1H).

Example 23

Preparation of
9-[(4-methylphenyl)-thiocarboxylacyl]-minocycline

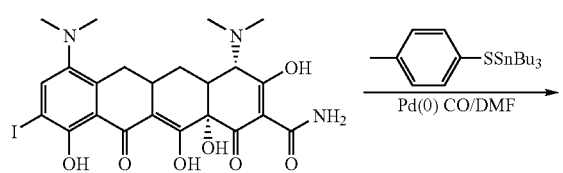

-continued

To solution of 4-methylbenzenethiol sodium salt (20.0 g, 137 mmol) in anhydrous DMF (500 mL) under argon was added Bu$_3$SnCl (36.9 mL, 137 mmol) drop wise. After 12 hours, the solution was poured into a 1:1 solution of hexane/water (1000 mL), and then the layers were separated. The water layer was back extracted with hexane (250 mL). The combined organic layers were dried over anhydrous MgSO$_4$, filtered rinsing with hexane, and then concentrated under reduced pressure to afford 4-methylbenzenethil tributyltin (56.5 g) as colorless oil in 99% yield. To a solution of anhydrous 9-iodominocycline freebase (20.4 g, 35.0 mmol), 4-methylphenylthiotributyltin (15.9 g, 38.5 mmol) and Pd(PPh$_3$)$_4$ (2.02 g, 1.75 mmol) in anhydrous DMF (175 mL) was bubbled CO for 15 minutes, then heated to 70° C. with a large balloon of CO affixed to the flask to maintain a positive pressure of CO. After 12 hours, the reaction was cooled to room temperature and poured into a cold 1:1 solution of 1% TFA/H$_2$O (500 mL) and MTBE (500 mL). After separating layers, the organic layer was back extracted with 1% TFA/H$_2$O (500 mL). The combined water layers were loaded onto a previously prepared funnel of DVB resin (7×15 cm packed DVB column). After loading, a cold solution of 1M NaOAc was eluted until the eluent became basic (approx. 300 mL), then water (400 mL) and finally 1:1 CH$_3$CN/THF to elute the desired product. The yellow solution was concentrated under reduced pressure and further dried under high vacuum overnight to afford 18.5 g as an orange-yellow solid in 87% yield. MS: M+1=608; $^1$H NMR (300 MHz, CD$_3$OD) δ 8.00 (s, 1H), 7.38-7.26 (m, 1H), 4.07 (s, 1H), 3.42-2.76 (m, 15H), 2.37 (s, 3H), 2.32-2.67 (m, 1H), 2.25-2.06 (m, 1H), 1.72-1.60 (m, 1H).

Example 24

Preparation of 9-propionyl minocycline

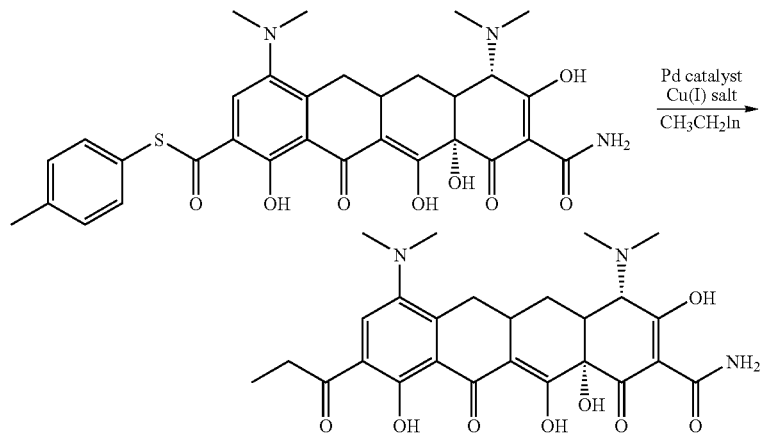

A 1000 mL 2 neck round-bottomed flask with reflux condenser was charged with anhydrous $InCl_3$ (12.1 g, 40.5 mmol) and dried under vacuum with a heat gun. After flask was cooled to ambient temperature and flushed with argon, anhydrous THF (240 mL) was added. The solution was cooled to −78° C. and $CH_3CH_2MgBr(Cl)$ (122 mL, 122 mmol) as a solution in THF was added. After 15 minutes, the solution was allowed to slowly warm to room temperature to form $(CH_3CH_2)_3In$ as a clear heterogeneous solution. To a solution of 9-[(4-methylphenyl)-thiocarboxyl acyl]-minocycline (1.70 g, 2.80 mmol), Cu(I)-thiophenecarboxylate (0.801 g, 4.20 mmol), $Pd_2(dba)_3$ (0.064 g, 0.070 mmol) and $P(2-furyl)_3$ (0.130 g, 0.560 mmol) in anhydrous THF (5 mL) under argon was added a 0.1M solution of previously prepared $(CH_3CH_2)_3In$ (56.0 mL, 5.60 mmol), then the solution was heated to reflux until reaction was complete. After cooling to room temperature, the solution was poured into cold 0.1M HCl (mL) and stirred for 1 hour. The solution was added to celite and then filtered through a large plug of Celite rinsing with cold water. The cold solution was loaded onto a prepared column of DVB resin (3×10 cm packed DVB column). When the loading was complete, water (300 mL) was eluted, and then $CH_3CN$ was eluted until the eluent became colorless. The yellow solution was concentrated under reduced pressure, the further purified by preparatory chromatography. The product was obtained as a yellow solid. MS: M+1=514; $^1$H NMR (300 MHz, $CD_3OD$) δ 8.28 (s, 1H), 4.13 (s, 1H), 3.42-2.91 (m, 17H), 2.63-2.47 (m, 1H), 2.32-2.15 (m, 1H), 1.70-1.54 (m, 1H), 1.14 (t, J=7 Hz, 3H).

Example 25

Preparation of 9-{1-[(E)-methoxyimino]-ethyl}-minocycline

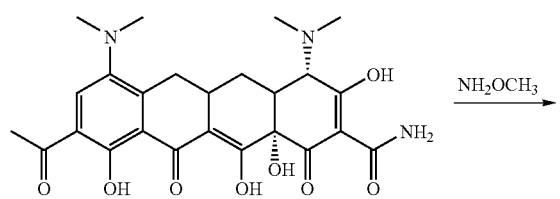

9-acetyl-minocycline (3.00 g, 5.24 mmol) was dissolved in methanol (50 mL) at room temperature in a dry 100 mL round bottom flask equipped with a magnetic stirring bar. Methoxylamine hydrochloride (2.23 g, 26.17 mmol) was then loaded in one portion, and the mixture was stirred at room temperature for 3 hours while being monitored by LC/MS. The solvent was evaporated to dryness, and a 1% TFA in water solution was added in order to purify the product on a DVB column. The product was eluted with a gradient of 1% TFA in water solution and a 50/50 mixture of methanol and acetonitrile. All solvents were evaporated and the residue was purified by preparative HPLC (C18 Lumina). After evaporating the volatiles, the aqueous solution was then loaded on a DVB column and washed with water to yield the product (a free base) as a yellow solid. MS: M+1=529. $^1$H-NMR (300 MHz, $CD_3OD$): ☐ 7.35 (s, 1H), 3.94 (s, 3H), 3.76 (t, 1H), 3.39 (dd, 1H), 2.89 (m, 1H), 2.73 (s, br, 6H), 2.66 (m, 1H), 2.61 (s, 6H), 2.22 (m, 1H), 2.21 (s, 3H), 2.12 (m, 1H), 1.65 (m, 1H).

Example 26

Preparation of 9-methoxyethylester minocycline

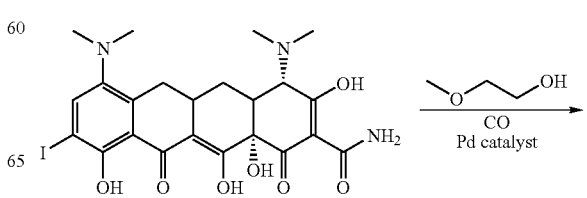

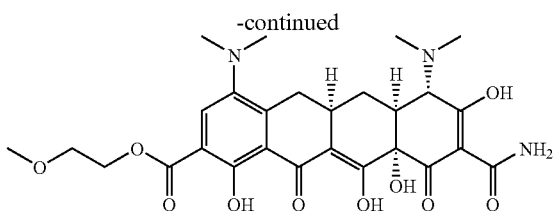

To a bomb was added 9-iodominocycline free base (4.00 g, 6.86 mmol), 2-methoxy ethanol (50 mL), tetrakis(triphenylphosphine)palladium(0) (1.5 g, 1.29 mmol), triethylamine (1.5 mL, 2.7 g, 20 mmol). The bomb was closed and charged with carbon monoxide (500 psi), heated to 70° C. and allowed to stir for 3 hours. The reaction was added to water (1.0 L) and the pH was lowered to 2 using trifluoroacetic acid. The solution was then filtered through celite to remove the catalyst, concentrated onto a plug of divinyl benzene (DVB) resin, eluted from the resin with acetonitrile and concentrated via rotary evaporation to give the crude product (4.5 g). The crude product was purified by HPLC using a C-18 column, triethanolamine (0.002 M) pH 7.4 aqueous buffer and acetonitrile as the organic phase. The fractions containing the desired compound were loaded onto a DVB plug, washed with aqueous 0.05 NaOAc (1.0 L) and eluted with acetonitrile to give the free base of 9-methoxyethylester minocycline as a dark red solid. MS: M+1=560; $^1$H-NMR (300 MHz, CD$_3$OD) δ 8.7-7.9 (m, 1H), 4.3-4.5 (m, 3H), 3.7-3.8 (m, 2H), 3.4-3.6 (m, 3H), 2.9-3.0 (m, 3H), 2.5-2.8 (m, 12H), 2.2-2.4 (m, 1H), 2.0-2.2 (m, 1H), 1.6-1.9 (m, 1H).

Example 27

Preparation of 9-carboxylic acid minocycline

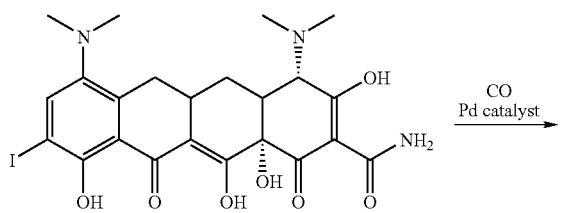

To a 1.0 L round bottom flask was added 9-iodo minocycline free base (30.0 g, 51.6 mmol), [1,1'-Bis(diphenylphosphino)-ferrocene]dichloropalladium(II) complex with dichloro methane 1:1 (5.0 g, 6.13 mmol), DMF (500 mL) and carbon monoxide (1 atm) was heated to 60° C. for 1 hour. Subsequently, a 1:1 solution of aqueous saturated sodium bicarbonate and DMF (300 mL) was slowly added to the reaction. The reaction was allowed to stir overnight then reduced to half the volume using rotory evaporation (5 mm Hg, 60° C.). The reaction was added to water (4.0 L) and the pH was lowered to 3 using trifluoroacetic acid. The solution was then filtered through celite to remove the catalyst, concentrated onto a plug of divinyl benzene (DVB) resin, eluted from the resin using a 5-25% gradient of acetonitrile in water buffered with an overall concentration of 0.1% TFA. The fractions containing compound were concentrated via rotary evaporation to 11.0 g crude product. Some of the crude product (1.0 g) was purified using HPLC using a C-18 column, triethanolamine (0.002 M) pH 7.4 aqueous buffer and acetonitrile as the organic phase. The fractions containing the desired compound were loaded onto a DVB plug, washed with aqueous 0.05 N HCl (1.0 L) and eluted with acetonitrile to give the HCl salt of the 9-carboxy minocycline as a dark yellow solid. MS: M+1=502; $^1$H-NMR (300 MHz, CD$_3$OD) δ 8.5 (s 1H), 4.2 (s, 1H), 3.4-3.6 (m, 6H), 2.9-3.2 (m, 8H), 2.5-2.7 (m, 1H), 2.3-2.5 (m, 1H), 1.6-1.9 (m, 1H).

Example 28

Preparation of 9-(alpha-keto acid)-minocycline

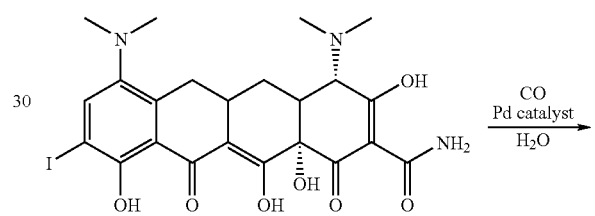

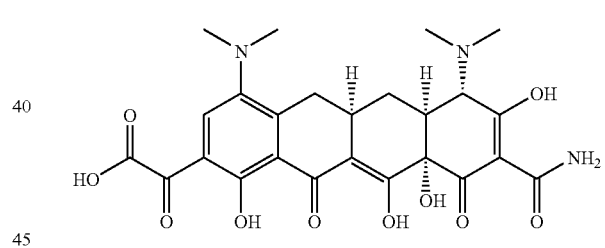

To a bomb was added 9-iodo minocycline free base (4.00 g, 6.86 mmol), DMF (50 mL), Pd(0) (1.59 g, 1.37 mmol), triethylamine (2.0 mL, 2.8 g, 2.7 mmol) and piperidine (7.88 g, 6.78 mL, 6.8 mmol). The bomb was closed and charged with carbon monoxide (400 psi), heated to 70° C. and allowed to stir for 3 h until the 9-piperidine amide dicarbonyl minocycline intermediate was seen (M+1=597). The intermediate was then hydrolyzed to the product by adding the reaction to water (1.0 L). The pH was lowered to 2 using trifluoroacetic acid and the solution was then filtered through celite to remove the catalyst, concentrated onto a plug of divinyl benzene (DVB) resin, eluted from the resin with acetonitrile and concentrated via rotary evaporation to 4 g crude product. The crude product was purified by HPLC using a C-18 column, triethanolamine (0.002 M) pH 7.4 aqueous buffer and acetonitrile as the organic. The fractions containing the desired compound were loaded onto DVB plug, washed with aqueous 0.05 HCl (1.0 L) and eluted with acetonitrile to give the free base of 9-alpha-keto acid minocycline as a yellow solid. MS: M+1=530; $^1$H-NMR (300 MHz, CD$_3$OD) δ 8.1-8.3 (m 1H), 4.1 (s, 1H), 3.4-3.6 (m, 9H), 2.9-3.2 (m, 11H), 2.5-2.8 (m, 1H), 2.3-2.5 (m, 1H), 1.6-1.9 (m, 1H).

Example 29

Preparation of 9-carboxylic acid amide minocycline

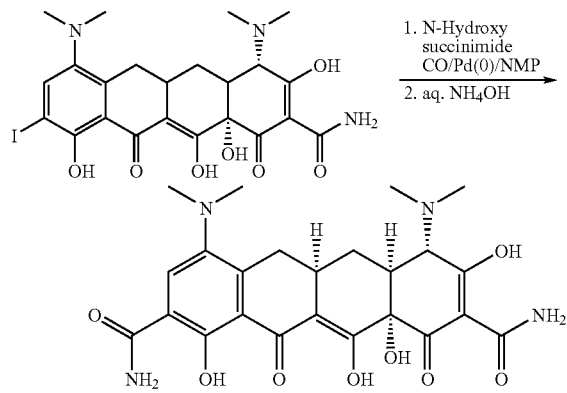

To 2 L flask was added (2.50 g, 4.30 mmol) 9-iodo minocycline free base, NMP (16.5 mL), N-hydroxysuccinimide (2.50 g, 221 mmol). To remove residual water from the above reactants toluene was added (500 mL), the flask was placed on the rotary evaporator (35 mm Hg, 45° C.) until all the toluene was evaporated. The flask was backfilled with argon and the contents were then transferred via cannula to a dry 50 mL flask. To the 50 mL flask was added tetrakis-(triphenylphosphine)palladium(0) (0.50 g, 0.40 m mol) and DIEA (3.0 mL, 174 m mol). The flask was placed under vacuum (20 mm Hg) and purged with carbon monoxide three times. The flask was then heated to 60° C. under 1.0 ATM of carbon monoxide and let stir for 3 h until all 9-iodo minocycline was consumed and a peak for the corresponding N-hydroxysuccinimide-ester intermediate (M+1=599) was formed as determined via LC/MS. Subsequently, 37% aqueous ammonia hydroxide (3.0 mL) was added and the reaction was allowed to stir for 5 min. The reaction was added to water (1.0 L) and the pH was lowered to 2 using trifluoroacetic acid. The solution was then filtered through celite to remove the catalyst, concentrated onto a plug of divinyl benzene (DVB) resin, eluted from the resin with acetonitrile and concentrated via rotary evaporation to 800 mg crude product. The crude product was purified by HPLC using a C-18 column, triethanolamine (0.002 M) pH 7.4 aqueous buffer and acetonitrile as the organic phase. The fractions containing the desired compound were loaded onto DVB plug, washed with aqueous 0.05 N HCl (1.0 L) and eluted with acetonitrile to give the HCl salt of 9-carboxamide minocycline as a beige colored solid. MS: M+1=501; $^1$H-NMR (300 MHz, CD$_3$OD) δ 8.4 (s 1H), 4.5 (s, 1H), 2.9-3.5 (m, 15H), 2.5-2.7 (m, 1H), 2.2-2.4 (m, 1H), 1.6-1.9 (m, 1H).

Example 30

In Vitro Minimum Inhibitory Concentration (MIC) Assay

The following assay is used to determine the efficacy of the tetracycline compounds against common bacteria. 2 mg of each compound is dissolved in 100 μl of DMSO. The solution is then added to cation-adjusted Mueller Hinton broth (CAMHB), which results in a final compound concentration of 200 μg per ml. The tetracycline compound solutions are diluted to 50 μL volumes, with a test compound concentration of 0.098 μg/ml. Optical density (OD) determinations are made from fresh log-phase broth cultures of the test strains. Dilutions are made to achieve a final cell density of 1×10$^6$ CFU/ml. At OD=1, cell densities for different genera should be approximately:

| | |
|---|---|
| E. coli | 1 × 10$^9$ CFU/ml |
| S. aureus | 5 × 10$^8$ CFU/ml |
| Enterococcus sp. | 2.5 × 10$^9$ CFU/ml |
| S. pseumoniae | 3 × 10$^8$ CFU/mL |

50 μl of the cell suspensions are added to each well of microtiter plates. The final cell density should be approximately 5×10$^5$ CFU/ml. These plates are incubated at 35° C. in an ambient air incubator for approximately 18 hour. The plates are read with a microplate reader and are visually inspected when necessary. The MIC is defined as the lowest concentration of the tetracycline compound that inhibits growth.

The compounds shown in Table 2 below were determined to have no measurable antibacterial activity.

Table 3 gives the MIC (μg/mL) of selected substituted tetracycline compounds against S. aureus, S. pseuimoniae, and E. coli. Compounds which showed superior inhibition of S. aureus, S. pseumoniae and E. coli are indicated by "*," and compounds which showed very good or good inhibition of S. aureus, S. pseumoniae and E. coli are indicated by "" or "*" respectively. The designation "ND" indicates that no value was obtained.

TABLE 2

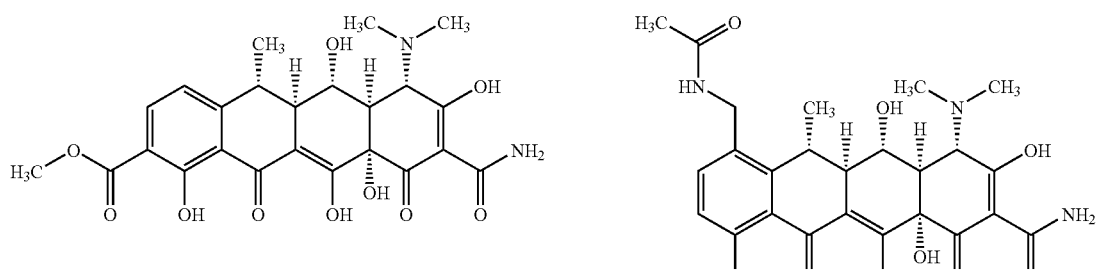

TABLE 2-continued
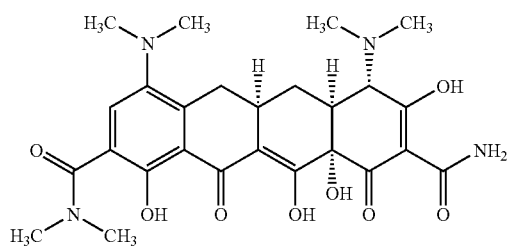 [SMILES: CN(C)C(=O)c1cc(N(C)C)c2c(c1O)C(=O)C1=C(O)[C@]3(O)C(=O)C(C(N)=O)=C(O)[C@@H](N(C)C)[C@@H]3C[C@@H]1C2]
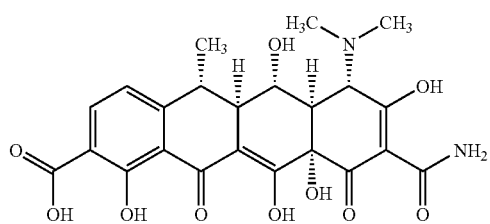 [SMILES: C[C@H]1c2ccc(C(=O)O)c(O)c2C(=O)C2=C(O)[C@]3(O)C(=O)C(C(N)=O)=C(O)[C@@H](N(C)C)[C@@H]3[C@@H](O)[C@@H]21]
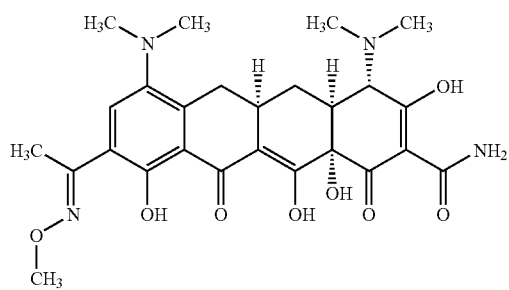 [SMILES: CO/N=C(\C)c1cc(N(C)C)c2c(c1O)C(=O)C1=C(O)[C@]3(O)C(=O)C(C(N)=O)=C(O)[C@@H](N(C)C)[C@@H]3C[C@@H]1C2]
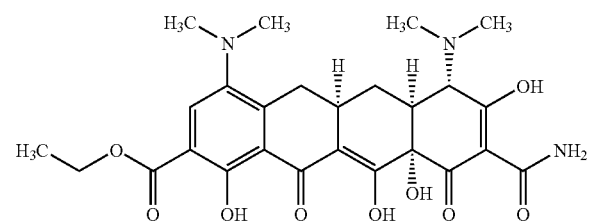 [SMILES: CCOC(=O)c1cc(N(C)C)c2c(c1O)C(=O)C1=C(O)[C@]3(O)C(=O)C(C(N)=O)=C(O)[C@@H](N(C)C)[C@@H]3C[C@@H]1C2]
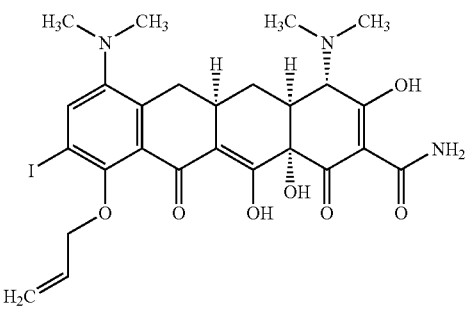 [SMILES: C=CCOc1c(I)cc(N(C)C)c2c1C(=O)C1=C(O)[C@]3(O)C(=O)C(C(N)=O)=C(O)[C@@H](N(C)C)[C@@H]3C[C@@H]1C2]
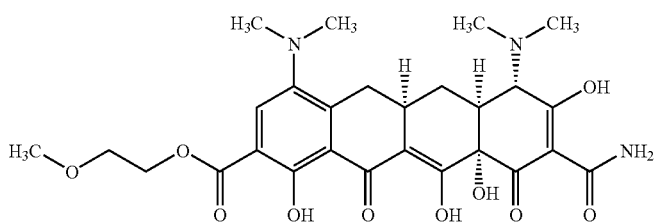 [SMILES: COCCOC(=O)c1cc(N(C)C)c2c(c1O)C(=O)C1=C(O)[C@]3(O)C(=O)C(C(N)=O)=C(O)[C@@H](N(C)C)[C@@H]3C[C@@H]1C2]
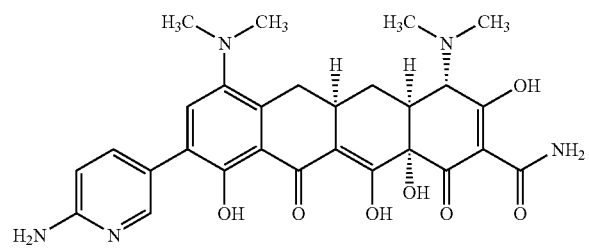 [SMILES: CN(C)c1cc(-c2ccc(N)nc2)c(O)c2c1C[C@H]1C[C@H]3[C@H](N(C)C)C(O)=C(C(N)=O)C(=O)[C@@]3(O)C(O)=C1C2=O]
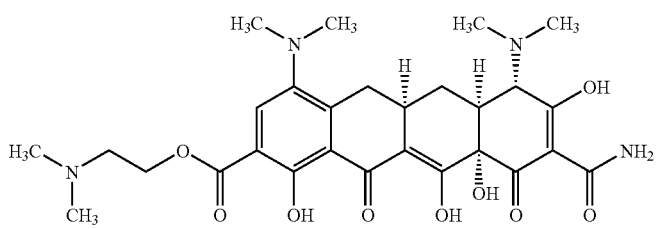 [SMILES: CN(C)CCOC(=O)c1cc(N(C)C)c2c(c1O)C(=O)C1=C(O)[C@]3(O)C(=O)C(C(N)=O)=C(O)[C@@H](N(C)C)[C@@H]3C[C@@H]1C2]

TABLE 2-continued
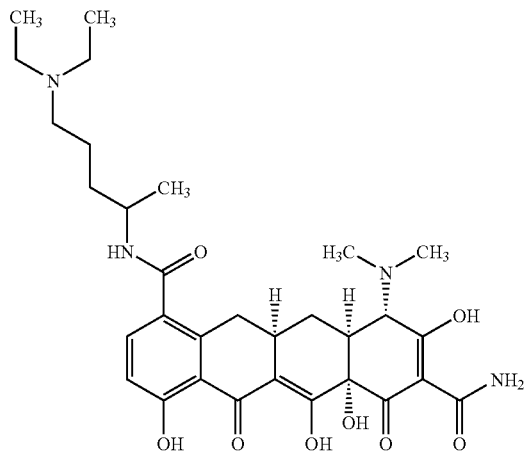 [SMILES: CCN(CC)CCCC(C)NC(=O)c1ccc(O)c2c1C[C@H]1C[C@H]3[C@H](N(C)C)C(O)=C(C(N)=O)C(=O)[C@@]3(O)C(O)=C1C2=O]
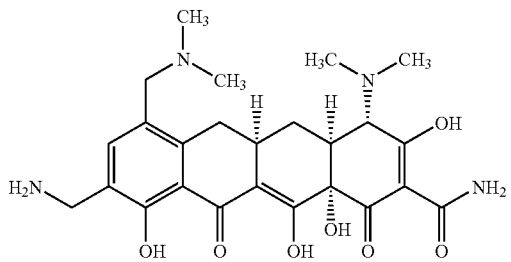 [SMILES: CN(C)Cc1cc(CN)c(O)c2c1C[C@H]1C[C@H]3[C@H](N(C)C)C(O)=C(C(N)=O)C(=O)[C@@]3(O)C(O)=C1C2=O]
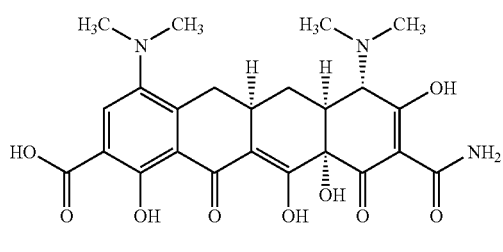 [SMILES: CN(C)c1cc(C(=O)O)c(O)c2c1C[C@H]1C[C@H]3[C@H](N(C)C)C(O)=C(C(N)=O)C(=O)[C@@]3(O)C(O)=C1C2=O]
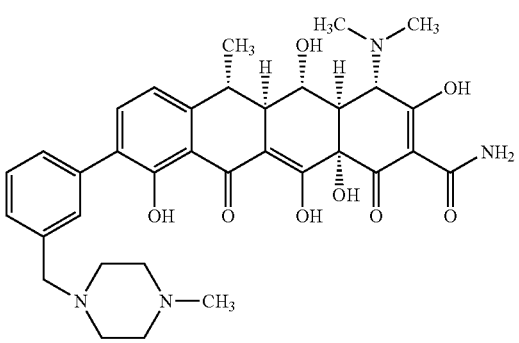 [SMILES: C[C@H]1c2ccc(-c3cccc(CN4CCN(C)CC4)c3)c(O)c2C(=O)C2=C(O)[C@]3(O)C(=O)C(C(N)=O)=C(O)[C@@H](N(C)C)[C@@H]3[C@@H](O)[C@@H]21]
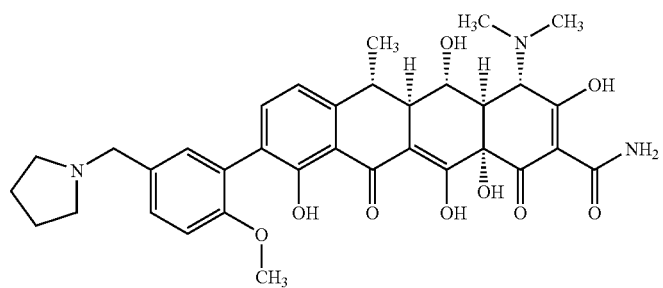 [SMILES: COc1ccc(CN2CCCC2)cc1-c1ccc2c(c1O)C(=O)C1=C(O)[C@]3(O)C(=O)C(C(N)=O)=C(O)[C@@H](N(C)C)[C@@H]3[C@@H](O)[C@@H]1[C@H]2C]
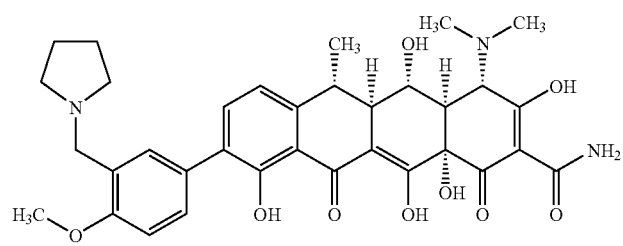 [SMILES: COc1ccc(-c2ccc3c(c2O)C(=O)C2=C(O)[C@]4(O)C(=O)C(C(N)=O)=C(O)[C@@H](N(C)C)[C@@H]4[C@@H](O)[C@@H]2[C@H]3C)cc1CN1CCCC1]

TABLE 2-continued

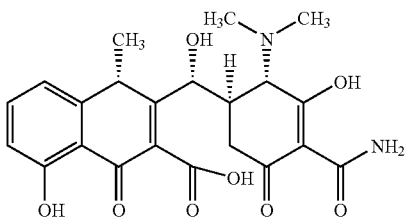 [SMILES: C[C@@H]1C([C@H](O)[C@@H]2CC(=O)C(C(N)=O)=C(O)[C@H]2N(C)C)=C(C(=O)O)C(=O)c2c(O)cccc21] 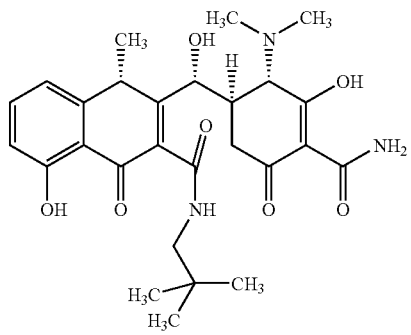 [SMILES: C[C@@H]1C([C@H](O)[C@@H]2CC(=O)C(C(N)=O)=C(O)[C@H]2N(C)C)=C(C(=O)NCC(C)(C)C)C(=O)c2c(O)cccc21]

Example 31

Assessment of Antimalarial Activity In Vivo

The assessment is performed with *P. vinckei*, a murine parasite that consistently causes a rapidly fatal malaria, and is an excellent model for drug efficacy. However, other murine parasites which are available (e.g. *P. berghei*) can also be studied using similar methodology.

20 gm Swiss Webster mice are inoculated intraperitoneally with $10^6$ *P. vinckei*-infected erythrocytes obtained from another infected mouse. Twelve hours after infection, treatment is initiated by the intraperitoneal injection of test compounds. Treatment is continued twice-a-day (BID) for four days. The progress of malaria infections in experimental and control (injected with diluent only) mice is followed by daily examinations of blood smears obtained from tail veins. The pharmacological endpoint is parasitemia >50%. Uninfected animals are followed for 6 weeks, and the animals that remain uninfected through this period are considered long-term cures.

The test compounds are injected into the stomach of the test mice by gavage. A number of variations of standard in vivo protocol may be utilized for specific purposes. For example, dosing intervals may be altered based on the known pharmacokinetics or observed initial efficacy data for a compound. Protocols may also be altered to more closely mimic true treatment (with delay of therapy after inoculation of parasites) or chemoprophylaxis (with treatment before the inoculation of parasites) conditions.

For all in vivo experiments, the mice are monitored daily, for at least the first two weeks of an experiment, with blood smears. Counts per 1000 erythrocytes provide parasitemias, and the parasitemias are then plotted over time, and results for control and experimental animals are compared.

Example 32

Mammalian Cytotoxicity Assay

COS-1 and CHO-K1 cell suspensions were prepared, seeded into 96-well tissue culture treated black-walled microtiter plates (density determined by cell line), and incubated overnight at 37° C., in 5% $CO_2$ and approximately 95% humidity. The following day, serial dilutions of drug were prepared under sterile conditions and transferred to cell plates. Cell/Drug plates were incubated under the above conditions for 24 hours. Following the incubation period, media/drug was aspirated and 50 µL of Resazurin (0.042 mg/ml in PBS w/Ca and Mg) was added. The plates were then incubated under the above conditions for 2 hours and then in the dark at room temperature for an additional 30 minutes. Fluorescence measurements were taken (excitation 535 nm, emission 590 nm). The $IC_{50}$ (concentration of drug causing 50% growth inhibition) was then calculated. The cytotoxicity of both unsubstituted minocycline and doxycycline were found to be greater than 25. Table 3 shows the results of this assay. Compounds which showed superior cytotoxicity are indicated by "*," and compounds which showed very good or good cytotoxicity are indicated by "" or "*" respectively. The designation "ND" indicates that no value was obtained.

TABLE 3

| MOLECULAR STRUCTURE | Median MIC for S. aureus RN450 (mg/mL) | Median MIC for S. pneumoniae 157E (mg/mL) | Median MIC for E. coli MG 1655 (mg/mL) | Cytotoxicity COS Tox50 (mL) | Cytotoxicity CHO Tox50 (mL) |
|---|---|---|---|---|---|
| 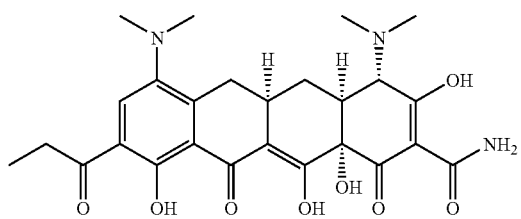 [SMILES: CCC(=O)c1cc(N(C)C)c2c(c1O)C(=O)C1=C(O)[C@]3(O)C(=O)C(C(N)=O)=C(O)[C@@H](N(C)C)[C@@H]3C[C@@H]1C2] | * | * | * |  |  |

TABLE 3-continued
| MOLECULAR STRUCTURE | Median MIC for S. aureus RN450 (mg/mL) | Median MIC for S. pneumoniae 157E (mg/mL) | Median MIC for E. coli MG 1655 (mg/mL) | Cytotoxicity COS Tox50 (mL) | Cytotoxicity CHO Tox50 (mL) |
|---|---|---|---|---|---|
| 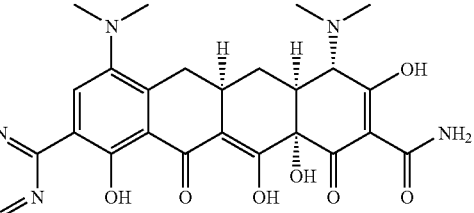 | * |  | * |  |  |
| 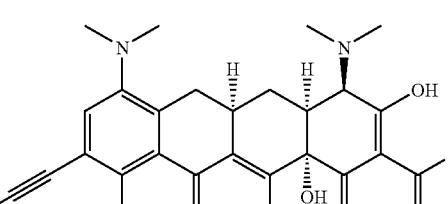 | * | * | * | * | * |
| 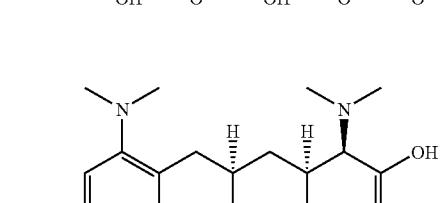 | * | * | * | * | * |
| 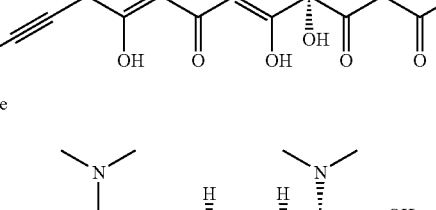 |  |  | * |  |  |
| 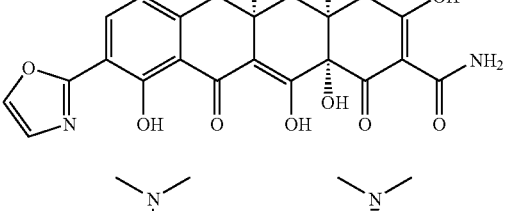 | * | * | * | * | * |
| 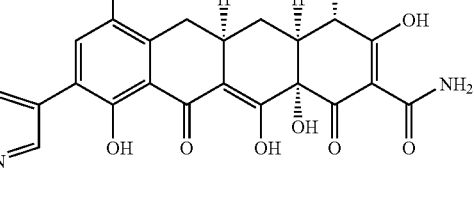 | * | * | * | * | * |

TABLE 3-continued

| MOLECULAR STRUCTURE | Median MIC for S. aureus RN450 (mg/mL) | Median MIC for S. pneumoniae 157E (mg/mL) | Median MIC for E. coli MG 1655 (mg/mL) | Cytotoxicity COS Tox50 (mL) | Cytotoxicity CHO Tox50 (mL) |
|---|---|---|---|---|---|
| [structure: 7-(3-methoxyprop-1-ynyl) minocycline analog] | *** | *** | * | ** | ** |
| [structure: 7-(N-methylcarbamoyl) minocycline analog] | * | * | * | * | * |
| [structure: 7-(pyridin-3-yl) minocycline analog] | ** | ** | * | * | * |
| [structure: 7-(pyridin-2-yl) minocycline analog] | *** | *** | * | * | * |
| [structure: 7-(thiazol-2-yl) minocycline analog] | *** | ** | * | * | * |
| [structure: 7-(pyridin-4-yl) minocycline analog] | *** | *** | * | * | * |

TABLE 3-continued

| MOLECULAR STRUCTURE | Median MIC for S. aureus RN450 (mg/mL) | Median MIC for S. pneumoniae 157E (mg/mL) | Median MIC for E. coli MG 1655 (mg/mL) | Cytotoxicity COS Tox50 (mL) | Cytotoxicity CHO Tox50 (mL) |
|---|---|---|---|---|---|
| (structure) | *** | *** | ** | ** | ** |
| (structure) | *** | *** | * | * | * |
| (structure) | * | * | * | * | * |
| (structure) | * | * | * | * | * |
| (structure) | * | * | * | * | * |
| (structure) | * | * | * |  |  |

TABLE 3-continued

| MOLECULAR STRUCTURE | Median MIC for *S. aureus* RN450 (mg/mL) | Median MIC for *S. pneumoniae* 157E (mg/mL) | Median MIC for *E. coli* MG 1655 (mg/mL) | Cytotoxicity COS Tox50 (mL) | Cytotoxicity CHO Tox50 (mL) |
|---|---|---|---|---|---|
| [structure] | * | * | * | * | * |
| [structure] | * | * | * | * | * |
| [structure] | * | * | * | * | * |
| [structure] | *** | *** | * | ** | ** |
| [structure] | *** | ** | * | * | * |
| [structure] | *** | *** | * | * | * |

TABLE 3-continued

| MOLECULAR STRUCTURE | Median MIC for S. aureus RN450 (mg/mL) | Median MIC for S. pneumoniae 157E (mg/mL) | Median MIC for E. coli MG 1655 (mg/mL) | Cytotoxicity COS Tox50 (mL) | Cytotoxicity CHO Tox50 (mL) |
|---|---|---|---|---|---|
| [structure with pyrazole substituent] | *** | ** | * | *** | *** |
| [structure with hydroxamic acid substituent] | * | * | * | ** | ** |
| [structure with methoxy-hydroxamic acid substituent] | * | * | * | * | * |
| [structure with 4-(dimethylamino)phenyl substituent] | *** | *** | * | *** | *** |
| [structure with pyrrolidine amide substituent] | * | * | * | * | * |
| [structure with propylamide substituent] | * | * | * | * | * |

TABLE 3-continued

| MOLECULAR STRUCTURE | Median MIC for *S. aureus* RN450 (mg/mL) | Median MIC for *S. pneumoniae* 157E (mg/mL) | Median MIC for *E. coli* MG 1655 (mg/mL) | Cytotoxicity COS Tox50 (mL) | Cytotoxicity CHO Tox50 (mL) |
|---|---|---|---|---|---|
| | ** | * | * | * | * |
| | ** | * | * | * | * |
| | * | * | * | * | * |
| | * | * | * | * | * |
| | * | * | * | * | * |
| | * | * | * | * | * |

TABLE 3-continued

| MOLECULAR STRUCTURE | Median MIC for S. aureus RN450 (mg/mL) | Median MIC for S. pneumoniae 157E (mg/mL) | Median MIC for E. coli MG 1655 (mg/mL) | Cytotoxicity COS Tox50 (mL) | Cytotoxicity CHO Tox50 (mL) |
|---|---|---|---|---|---|
| [structure] | * | * | * | * | * |
| [structure] | * | * | * | * | * |
| [structure] | * | *** | * | * | * |
| [structure] | * | *** | * | * | * |
| [structure] | * | * | * | * | * |
| [structure] | * | * | * | * | * |

TABLE 3-continued

| MOLECULAR STRUCTURE | Median MIC for *S. aureus* RN450 (mg/mL) | Median MIC for *S. pneumoniae* 157E (mg/mL) | Median MIC for *E. coli* MG 1655 (mg/mL) | Cytotoxicity COS Tox50 (mL) | Cytotoxicity CHO Tox50 (mL) |
|---|---|---|---|---|---|
| [structure] | * | ** | * | *** | *** |
| [structure] | ** | ** | * | * | * |
| [structure] | * | * | * | * | * |
| [structure] | *** | ** | * | ** | ** |
| [structure] | * | * | * | * | * |

TABLE 3-continued

| MOLECULAR STRUCTURE | Median MIC for *S. aureus* RN450 (mg/mL) | Median MIC for *S. pneumoniae* 157E (mg/mL) | Median MIC for *E. coli* MG 1655 (mg/mL) | Cytotoxicity COS Tox50 (mL) | Cytotoxicity CHO Tox50 (mL) |
|---|---|---|---|---|---|
| (structure) | * | * | * | * | * |
| (structure) | * | * | * |  |  |

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:
1. A compound of Formula (III):

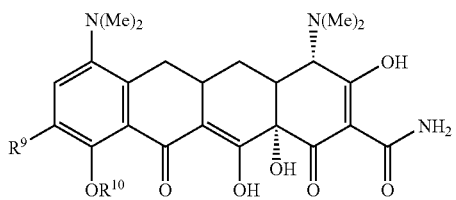

(III)

wherein
$R^9$ is $R^{9a}R^{9b}NC(=O)$ or cyclopropyl;
$R^{10}$ is hydrogen or alkenyl;
$R^{9a}$ is hydrogen or alkyl; and
$R^{9b}$ is hydrogen, alkyl, hydroxyl, alkoxy, hydroxyalkyl, alkoxyalkyl, alkylcarbonylaminoalkyl, alkoxycarbonylalkyl, aryl, cycloalkyl or aminoalkyl;
or a pharmaceutically acceptable salt, ester or prodrug thereof.

2. The compound of claim 1, wherein $R^{10}$ is alkenyl.
3. The compound of claim 1, wherein $R^{10}$ is hydrogen.
4. The compound of claim 3, wherein $R^9$ is $R^{9a}R^{9b}NC(=O)$—.
5. The compound of claim 4, wherein $R^{9a}$ and $R^{9b}$ are each methyl or ethyl.
6. The compound of claim 4, wherein $R^{9a}$ is alkyl.
7. The compound of claim 4, wherein $R^{9b}$ is alkoxyalkyl.
8. The compound of claim 4, wherein $R^{9a}$ is hydrogen.
9. The compound of claim 8, wherein $R^{9b}$ is hydrogen, hydroxy, alkoxy, hydroxyalkyl, alkyl, cycbalkyl, alkylcarbonylaminoalkyl, alkoxycarbonylalkyl, aryl or aminoalkyl.
10. The compound of claim 1, which is selected from the group consisting of:

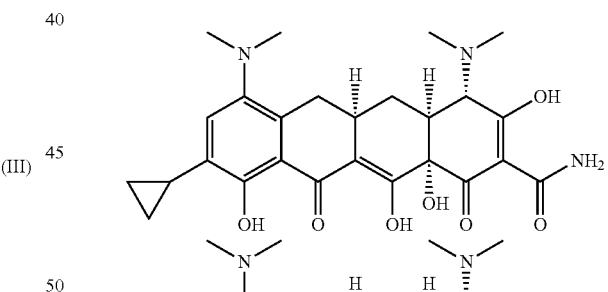

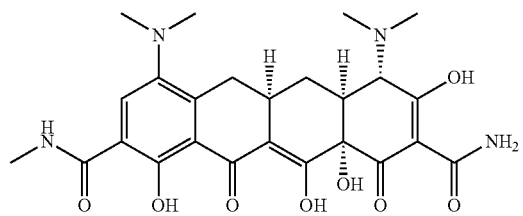 [SMILES: CNC(=O)c1cc(N(C)C)c2c(c1O)C(=O)C1=C(O)[C@]3(O)C(=O)C(C(N)=O)=C(O)[C@@H](N(C)C)[C@@H]3C[C@@H]1C2]

151
-continued
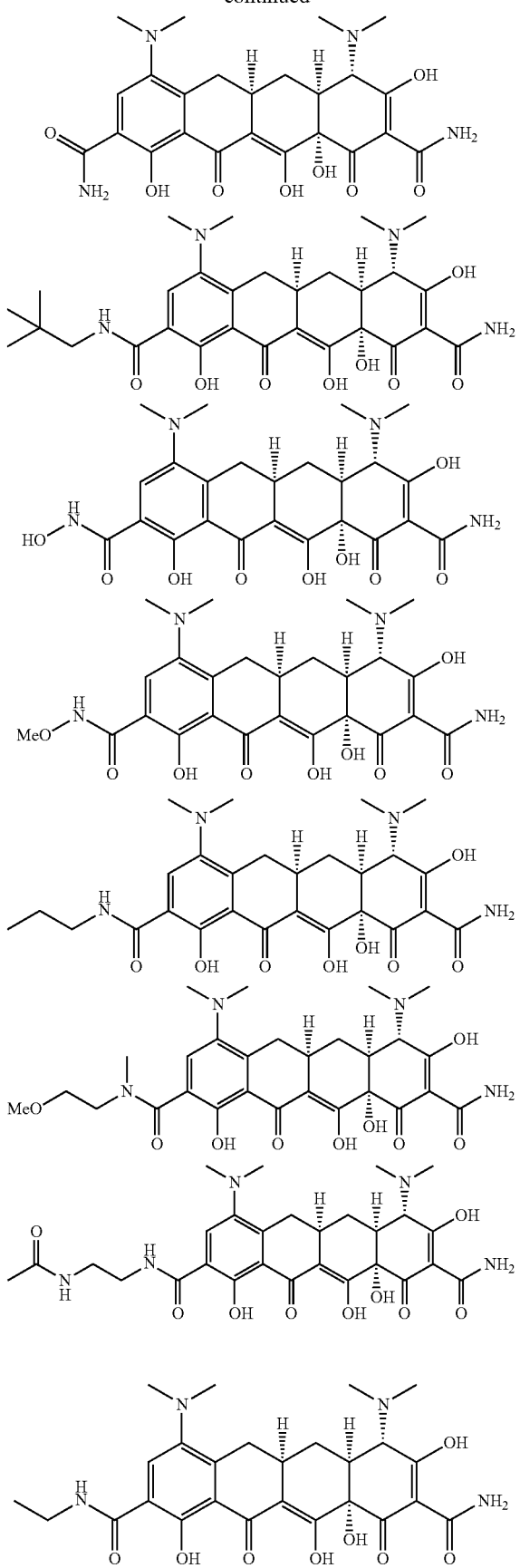
152
-continued
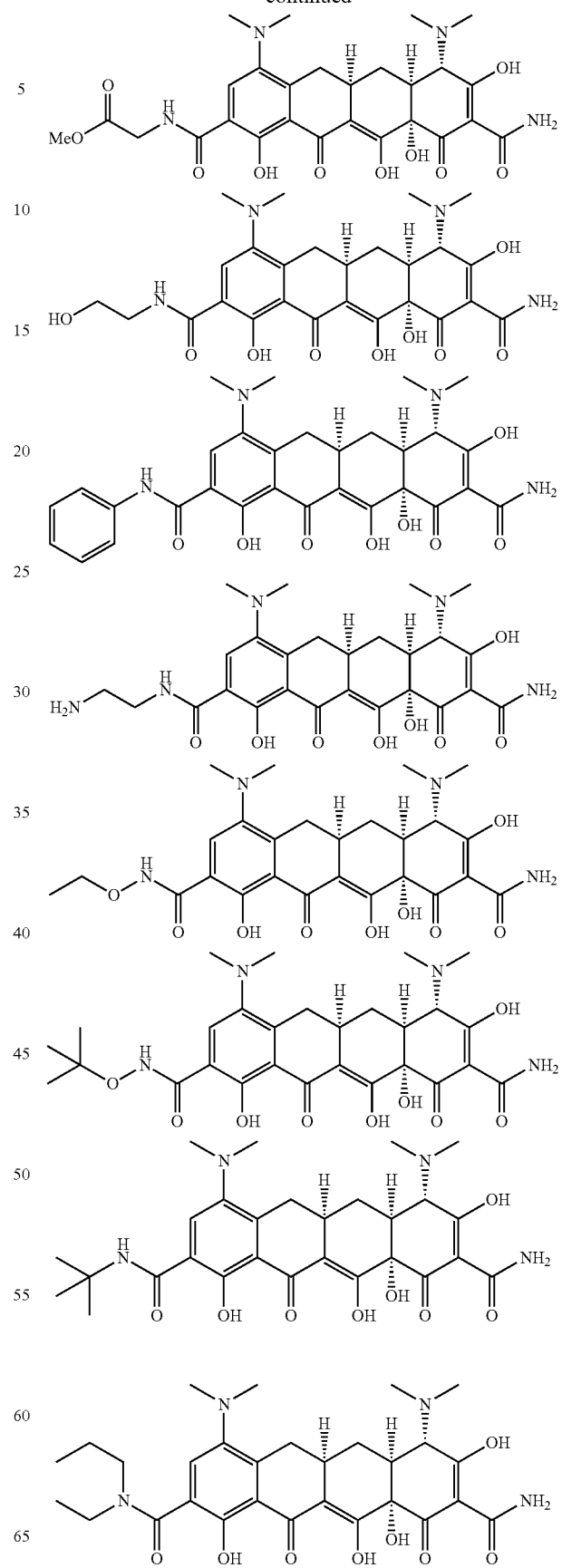

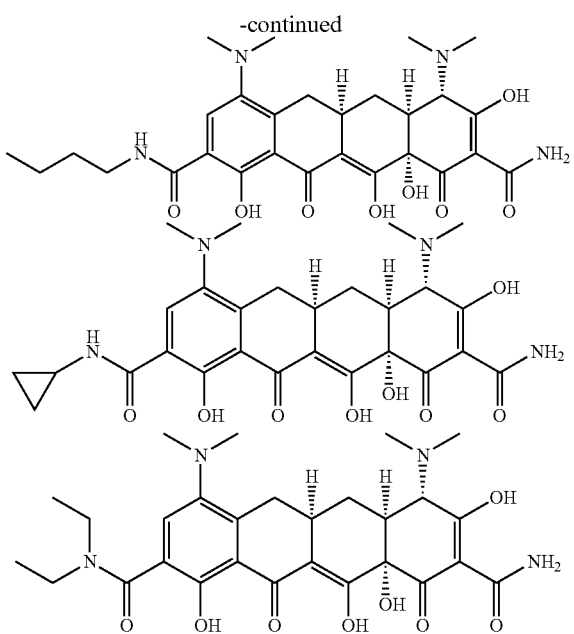

and pharmaceutically acceptable salts, esters and prodrugs thereof.

11. The compound of claim 10, wherein said compound is

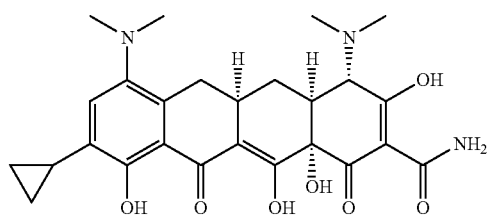 [SMILES: CN(C)c1cc(C2CC2)c(O)c2c1C[C@H]1C[C@H]3[C@H](N(C)C)C(O)=C(C(N)=O)C(=O)[C@@]3(O)C(O)=C1C2=O]

or a pharmaceutically acceptable salt thereof.

12. A compound, which is:

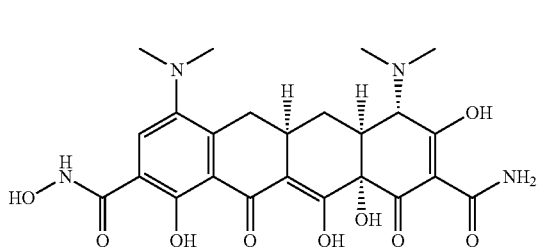 [SMILES: CN(C)c1cc(C(=O)NO)c(O)c2c1C[C@H]1C[C@H]3[C@H](N(C)C)C(O)=C(C(N)=O)C(=O)[C@@]3(O)C(O)=C1C2=O]

or a pharmaceutically acceptable salt thereof.

13. A compound, which is:

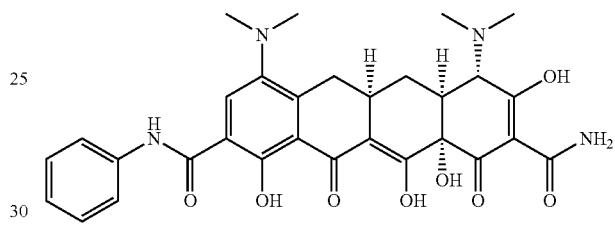

or a pharmaceutically acceptable salt thereof.

14. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,466,132 B2 | Page 1 of 1 |
| APPLICATION NO. | : 11/258622 | |
| DATED | : June 18, 2013 | |
| INVENTOR(S) | : Abato et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1336 days.

Signed and Sealed this
Eleventh Day of November, 2014

Michelle K. Lee
*Deputy Director of the United States Patent and Trademark Office*